(12) United States Patent
Gu et al.

(10) Patent No.: US 11,110,168 B2
(45) Date of Patent: Sep. 7, 2021

(54) NANOPARTICLES, CONTROLLED-RELEASE DOSAGE FORMS, AND METHODS FOR DELIVERING AN IMMUNOTHERAPEUTIC AGENT

(71) Applicant: NORTH CAROLINA STATE UNIVERSITY, Ralegih, NC (US)

(72) Inventors: Zhen Gu, Raleigh, NC (US); Chao Wang, Raleigh, NC (US); Yanqi Ye, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 59 days.

(21) Appl. No.: 16/085,015

(22) PCT Filed: Mar. 15, 2017

(86) PCT No.: PCT/US2017/022568
§ 371 (c)(1),
(2) Date: Sep. 14, 2018

(87) PCT Pub. No.: WO2017/161032
PCT Pub. Date: Sep. 21, 2017

(65) Prior Publication Data
US 2019/0054166 A1    Feb. 21, 2019

Related U.S. Application Data

(60) Provisional application No. 62/308,513, filed on Mar. 15, 2016, provisional application No. 62/380,711, filed on Aug. 29, 2016.

(51) Int. Cl.
| | |
|---|---|
| *A61K 39/395* | (2006.01) |
| *A61K 39/39* | (2006.01) |
| *C07K 16/28* | (2006.01) |
| *A61K 9/00* | (2006.01) |
| *A61K 9/51* | (2006.01) |
| *A61K 47/55* | (2017.01) |
| *A61K 47/69* | (2017.01) |
| *A61K 39/00* | (2006.01) |

(52) U.S. Cl.
CPC .......... *A61K 39/39* (2013.01); *A61K 9/0021* (2013.01); *A61K 9/513* (2013.01); *A61K 39/39541* (2013.01); *A61K 47/55* (2017.08); *A61K 47/6949* (2017.08); *C07K 16/2818* (2013.01); *A61K 2039/505* (2013.01); *A61K 2039/55561* (2013.01); *C07K 2317/76* (2013.01)

(58) Field of Classification Search
None
See application file for complete search history.

(56) References Cited

U.S. PATENT DOCUMENTS

| | | |
|---|---|---|
| 8,217,149 B2 | 7/2012 | Irving et al. |
| 2009/0182306 A1 | 7/2009 | Lee |
| 2010/0311168 A1 | 12/2010 | Samule et al. |
| 2011/0195030 A1 | 8/2011 | Mumper et al. |
| 2013/0210896 A1 | 8/2013 | Badie et al. |
| 2013/0280334 A1 | 10/2013 | Karp et al. |
| 2016/0058784 A1 | 3/2016 | Primiano, II et al. |
| 2016/0067358 A1 | 3/2016 | Mukherjee et al. |

FOREIGN PATENT DOCUMENTS

| | | |
|---|---|---|
| WO | 2011066389 | 6/2011 |
| WO | 2015153975 | 10/2015 |
| WO | 2016010788 A1 | 1/2016 |

OTHER PUBLICATIONS

Albain, K.; Swann, R.; Rusch, V.; Turrisi, A.; Shepherd, F.; Smith, C.; Gandara, D.; Johnson, D.; Green, M.; Miller, R. In ASCO Annual Meeting Proceedings 2005; vol. 23, p. 7014.

Ali, M. M.; et al., "Rolling circle amplification: a versatile tool for chemical biology, materials science and medicine", Chem. Soc. Rev. 2014, 43, 3324.

Antonio, N.; et al., "The wound inflammatory response exacerbates growth of pre-neoplastic cells and progression to cancer", EMBO J. 2015, 34, 2219.

Armstrong, D. G.; Jude, E. B., "The role of matrix metalloproteinases in wound healing", J. Am. Podiatr. Med. Assoc. 2002, 92, 12.

Awuah, S. G.; et al., "A Pt(IV) Pro-drug Preferentially Targets Indoleamine-2,3-dioxygenase, Providing Enhanced Ovarian Cancer Immuno-Chemotherapy." J. Am. Chem. Soc. 2015, 137 (47), 14854-14857.

Baker, D.; et al., "The influence of the surgical wound on local tumor recurrence", Surgery 1989, 106, 525.

Buchbinder, E. I.; Hodi, F. S., Melanoma in 2015: Immune-checkpoint blockade—durable cancer control. Nat. Rev. Clin. Oncol. 2016, 13 (2), 77-78.

Ceelen, W.; et al., "Surgery, wound healing, and metastasis: recent insights and clinical implications", Crit. Rev. Oncol. Hematol. 2014, 89, 16-26.

Cheung, A. S.; Mooney, D. J., "Engineered materials for cancer immunotherapy." Nano Today 2015, 10 (4), 511-531.

Coffey, J. C.; et al., "Excisional surgery for cancer cure: therapy at a cost", Lancet Oncol. 2003, 4, 760.

(Continued)

*Primary Examiner* — Yunsoo Kim

(74) *Attorney, Agent, or Firm* — Meunier Carlin & Curfman LLC

(57) ABSTRACT

The present disclosure relates to nanoparticles, controlled-release dosage forms, and methods for the administration of an immunotherapeutic agent.

7 Claims, 50 Drawing Sheets

Specification includes a Sequence Listing.

(56) References Cited

OTHER PUBLICATIONS

Curran, M. A.; et al., "PD-1 and CTLA-4 combination blockade expands infiltrating T cells and reduces regulatory T and myeloid cells within B16 melanoma tumors", Proc. Natl. Acad. Sci. U. S. A. 2010, 107, 4275.
Demicheli, R.; et al., "The effects of surgery on tumor growth: a century of investigations", Ann. Oncol. 2008, mdn386.
DeMuth, P. C.; et al., "Vaccine delivery with microneedle skin patches in nonhuman primates." Nat. Biotechnol. 2013, 31 (12), 1082-1085.
DeMuth, P. C.; et al., "Implantable Silk Composite Microneedles for Programmable Vaccine Release Kinetics and Enhanced Immunogenicity in Transcutaneous Immunization." Adv. Healthcare Mater. 2014, 3 (1), 47-58.
DeMuth, P. C.; et al., "Releasable Layer-by-Layer Assembly of Stabilized Lipid Nanocapsules on Microneedles for Enhanced Transcutaneous Vaccine Delivery." ACS Nano 2012, 6 (9), 8041-8051.
DeMuth, P. C.; et al., "Nano-Layered Microneedles for Transcutaneous Delivery of Polymer Nanoparticles and Plasmid DNA." Adv. Mater. 2010, 22 (43), 4851-4856.
Fadel, T. R.; et al., "A carbon nanotube—polymer composite for T-cell therapy", Nat. Nanotechnol. 2014, 9, 639.
Gajanayake, T.; et al., "A single localized dose of enzyme-responsive hydrogel improves long-term survival of a vascularized composite allograft", Sci. Transl. Med. 2014, 6, 249ra110.
Goldberg, M. S. "Immunoengineering: how nanotechnology can enhance cancer immunotherapy", Cell 2015, 161, 201.
Grivennikov, S. I.; et al., "Immunity, inflammation, and cancer", Cell 2010, 140, 883.
Gubin, M. M.; et al., "Checkpoint blockade cancer immunotherapy targets tumour-specific mutant antigen", Nature 2014, 515, 577.
Hamid, O.; et al., "Safety and tumor responses with lambrolizumab (anti-PD-1) in melanoma", N. Engl. J. Med. 2013, 369, 134.
Hervé, C.; et al., "Determination of tryptophan and its kynurenine pathway metabolites in human serum by high-performance liquid chromatography with simultaneous ultraviolet and fluorimetric detection." J. Chromatogr. B Biomed. Sci. Appl. 1996, 675 (1), 157-161.
Hu, Q.; et al., "Tumor Microenvironment-Mediated Construction and Deconstruction of Extracellular Drug-Delivery Depots." Nano Lett. 2016, 16 (2), 1118-1126.
Huang, B. N.; et al., "Active targeting of chemotherapy to disseminated tumors using nanoparticle-carrying T cells", Sci. Transl. Med. 2015, 7, 291ra94.
Hwang, S. L.; et al., "Indoleamine 2, 3-dioxygenase (IDO) is essential for dendritic cell activation and chemotactic responsiveness to chemokines." Cell Res. 2005, 15 (3), 167-175.
Irvine, D. J.; et al., "Synthetic nanoparticles for vaccines and immunotherapy", Chem. Rev. 2015, 115, 11109.
Jeanbart, L.; Swartz, M. A., "Engineering opportunities in cancer immunotherapy." Proc. Natl. Acad. Sci. 20 15, 112 (47), 14467-14472.
Jones, M. R.; et al., "Programmable materials and the nature of the DNA bond", Science 2015, 347, 1260901.
Kim, J.; et al., "Injectable, spontaneously assembling, inorganic scaffolds modulate immune cells in vivo and increase vaccine efficacy", Nat. Biotechnol. 2015, 33, 64.
Kim, Y.-C.; et al., "Microneedles for drug and vaccine delivery." Adv. Drug Delivery Rev. 2012, 64 (14), 1547-1568.
Koshy, S. T.; Mooney, D. J., "Biomaterials for enhancing anti-cancer immunity." Curr. Opin. Biotechnol. 2016, 40, 1-8.
Krieg, A. M. "Toll-like receptor 9 (TLR9) agonists in the treatment of cancer", Oncogene 2008, 27, 161.
Kwon, E. D.; et al., "Elimination of residual metastatic prostate cancer after surgery and adjunctive cytotoxic T lymphocyte-associated antigen 4 (CTLA-4) blockade immunotherapy", Proc. Natl. Acad. Sci. U. S. A. 1999, 96, 15074.

Larkin, J.; et al., "Combined Nivolumab and Ipilimumab or Monotherapy in Untreated Melanoma." N. Engl. J. Med. 2015, 373 (1), 23-34.
Le, D. T.; et al., "PD-1 Blockade in Tumors with Mismatch-Repair Deficiency." N. Engl. J. Med. 2015, 372 (26), 2509-2520.
Li, W. A.; Mooney, D. J., "Materials based tumor immunotherapy vaccines." Curr. Opin. Immunol. 2013, 25 (2), 238-245.
Liu, Q.; et al., "Abrogation of local cancer recurrence after radiofrequency ablation by dendritic cell-based hyperthermic tumor vaccine", Molecular Therapy 2009, 17, 2049.
Lu, Y.; et al., "Stimuli-responsive nanomaterials for therapeutic protein delivery." J. Controlled Release 2014, 194, 1-19.
Lu, Y.; et al., "Transformable liquid-metal nanomedicine." Nat. Commun. 2015, 6, 10066.
Lv, Y.; et al., "Preparation and biomedical applications of programmable and multifunctional DNA nanoflowers", Nature protocols 2015, 10, 1508.
Mai, Y.; Eisenberg, A., "Self-assembly of block copolymers." Chem. Soc. Rev. 2012, 41 (18), 5969.
Marabelle, A.; et al., "Depleting tumor-specific Tregs at a single site eradicates disseminated tumors" J. Clin. Invest. 2013, 123, 2447.
Mellati, M.; et al., "Anti-PD-1 and anti-PDL-1 monoclonal antibodies causing type 1 diabetes", Diabetes Care 2015, 38, e137.
Mellor, A. L.; Munn, D. H., "IDO expression by dendritic cells: tolerance and tryptophan catabolism." Nat. Rev. Immunol. 2004, 4 (10), 762-774.
Mitragotri, S.; et al., "Accelerating the Translation of Nanomaterials in Biomedicine." ACS Nano 2015, 9 (7), 6644-6654.
Mitragotri, S.; et al., "Overcoming the challenges in administering biopharmaceuticals: formulation and delivery strategies", Nat. Rev. Drug Discovery 2014, 13, 655.
Moon, J. J.; et al., "Engineering Nano- and Microparticles to Tune Immunity." Adv. Mater. 2012, 24 (28), 3724-3746.
Moon, Y. W.; et al., "Targeting the indoleamine 2,3-dioxygenase pathway in cancer." J. Immunother. Cancer. 2015, 3 (1).
Muller, A. J.; et al., "Inhibition of indoleamine 2,3-dioxygenase, an immunoregulatory target of the cancer suppression gene Bin1, potentiates cancer chemotherapy." Nat. Med. 2005, 11 (3), 312-319.
Mura, S.; et al., "Stimuli-responsive nanocarriers for drug delivery", Nat. Mater. 2013, 12, 991.
Naidoo, J.; et al., "Toxicities of the anti-PD-1 and anti-PD-L1 immune checkpoint antibodies", Ann. Oncol. 2015, mdv383.
Nochi, T.; et al., "Nanogel antigenic protein-delivery system for adjuvant-free intranasal vaccines", Nat. Mater. 2010, 9, 572.
Paik, S.; et al., "A multigene assay to predict recurrence of tamoxifen-treated, node-negative breast cancer.", New England Journal of Medicine 2004, 351, 2817.
Pardoll, D. M., "The blockade of immune checkpoints in cancer immunotherapy", Nat. Rev. Cancer 2012, 12, 252.
Park, J.; et al., "Combination delivery of TGF-β inhibitor and IL-2 by nanoscale liposomal polymeric gels enhances tumour immunotherapy", Nat. Mater. 2012, 11, 895.
Patnaik, a.; et al., "Phase I study of MK-3475 (anti-PD-1 monoclonal antibody) in patients with advanced solid tumors.", In ASCO Annual Meeting Proceedings 2012; vol. 30, p. 2512.
Peer, D.; et al., "Nanocarriers as an emerging platform for cancer therapy." Nat. Nanotechnol. 2007, 2 (12), 751-760.
Pilotte, L.; et al., "Reversal of tumoral immune resistance by inhibition of tryptophan 2,3-dioxygenase." Proc. Natl. Acad. Sci. 2012, 109 (7), 2497-2502.
Postow, M. A.; et al., "Nivolumab and ipilimumab versus ipilimumab in untreated melanoma." N. Engl. J. Med. 2015, 372 (21), 2006-17.
Prausnitz, M. R.; Langer, R., "Transdermal drug delivery." Nat. Biotechnol. 2008, 26 (11), 1261-1268.
Ribas, A. N., "Releasing the brakes on cancer immunotherapy", N Engl. J. Med. 2015, 373, 1490.
Robert, C., et al., "Pembrolizumab versus ipilimumab in advanced melanoma." New England Journal of Medicine 2015, 372(26), 2521-2532.
Roh, Y. H.; et al., "Layer-by-Layer Assembled Antisense DNA Microsponge Particles for Efficient Delivery of Cancer Therapeutics", ACS Nano 2014, 8, 9767.

(56) References Cited

OTHER PUBLICATIONS

Rosenberg, J. E.; et al., "Atezolizumab in patients with locally advanced and metastatic urothelial carcinoma who have progressed following treatment with platinum-based chemotherapy: a single-arm, multicentre, phase 2 trial." The Lancet 2016, 387 (10031), 1909-1920.
Sabado, R. L.; Bhardwaj, N., "Cancer immunotherapy: dendritic-cell vaccines on the move", Nature 2015, 519, 300.
Segatto, I.; et al., "Surgery-induced wound response promotes stem-like and tumor-initiating features of breast cancer cells, via STAT3 signaling", Oncotarget 2014, 5, 6267.
Sharma, P., & Allison, J. P. "The future of immune checkpoint therapy." Science 2015, 348(6230), 56-61.
Sharma, P.; Allison, James P., "Immune Checkpoint Targeting in Cancer Therapy: Toward Combination Strategies with Curative Potential." Cell 2015, 161 (2), 205-214.
Sinclair RD, et al., "Proteolytic enzymes in wound healing: the role of enzymatic debridement.", J. Dermatol. 1994, 35, 35-41.
Spranger, S.; "Up-Regulation of PD-L1, IDO, and Tregs in the Melanoma Tumor Microenvironment Is Driven by CD8+ T Cells." Sci. Transl. Med. 2013, 5 (200), 200ra116-200ra116.
Stephan, M. T.; et al., "Therapeutic cell engineering with surface-conjugated synthetic nanoparticles", Nat. Med. 2010, 16, 1035.
Stephan, S. B.; et al., "Biopolymer implants enhance the efficacy of adoptive T-cell therapy.", Nat. Biotechnol. 2015, 33, 97.
Sullivan, R. J.; Flaherty, K. T., "Immunotherapy: Anti-PD-1 therapies—a new first-line option in advanced melanoma." Nat. Rev. Clin. Oncol. 2015, 12 (11), 625-626.
Sullivan, S. P.; et al., "Dissolving polymer microneedle patches for influenza vaccination." Nat. Med. 2010, 16 (8), 915-920.
Sun, W.; et al., "Cocoon-like self-degradable DNA nanoclew for anticancer drug deliver", J. Am. Chem. Soc. 2014, 136, 14722.
Sun, W.; et al., "Efficient Delivery of CRISPR-Cas9 for Genome Editing via SelfAssembled DNA Nanoclews", Angew. Chem. Int. Ed. 2015, 54, 12029.
Tai, W.; et al., "Bio-Inspired Synthetic Nanovesicles for Glucose-Responsive Release of Insulin." Biomacromolecules 2014, 15 (10), 3495-3502.
Topalian, S. L.; et al., "Safety, activity, and immune correlates of anti-PD-1 antibody in cancer", N. Engl. J. Med. 2012, 366, 2443.
Topalian, S. L.; et al., "Survival, durable tumor remission, and long-term safety in patients with advanced melanoma receiving nivolumab", Journal of Clinical Oncology 2014, 32, 1020.
Topalian, Suzanne L.; et al., "Immune Checkpoint Blockade: A Common Denominator Approach to Cancer Therapy." Cancer Cell 2015, 27 (4), 450-461.
Uyttenhove, C.; et al., "Evidence for a tumoral immune resistance mechanism based on tryptophan degradation by indoleamine 2,3-dioxygenase." Nat. Med. 2003, 9 (10), 1269-1274.
Vakkila, J.; et al., Inflammation and necrosis promote tumour growth, Nat. Rev. Immunol. 2004, 4, 641.
Wang, C.; et al., "Enhanced Cancer Immunotherapy by Microneedle Patch-Assisted Delivery of Anti-PD1 Antibody." Nano Lett. 2016, 16 (4), 2334-2340.
Wang, C.; et al., "Immunological responses triggered by photothermal therapy with carbon nanotubes in combination with anti-CTLA-4 therapy to inhibit cancer metastasis", Adv. Mater. 2014, 26, 8154.
Wang, C.; et al., "Inflammation-Triggered Cancer Immunotherapy by Programmed Delivery of CpG and Anti-PD1 Antibody." Adv. Mater. 2016, 8912.
Yu, J.; et al., "Microneedle-array patches loaded with hypoxia-sensitive vesicles provide fast glucose-responsive insulin delivery." Proc. Natl. Acad. Sci. 2015, 112(27), 8260-8265.
Zou, W.; et al., "PD-L1 (B7-H1) and PD-1 pathway blockade for cancer therapy: Mechanisms, response biomarkers, and combinations.", Sci. Transl. Med. 2016, 8 (328), 328rv4-328rv4.
International Search Report and Written Opinion issued for Application No. PTC/US2017/022568, dated Jun. 5, 2017, 17 pages.
International Preliminary Report on Patentability issued for Application No. PTC/US2017/022568, dated Sep. 27, 2018.
Supplementary Partial European Search Report in corresponding Application No. EP 17767464.5, dated Aug. 28, 2019, 10 pages.
Extended European Search Report, issued in corresponding application No. EP17767464.5, dated Dec. 12, 2019, 9 pages.
Office Action issued in corresponding Chinese Application No. 201780025213.1, dated Jul. 2, 2020, 14 pages.
Mohri et al, "DNA nanotechnology-based development of delivery systems for bioactive compounds", European Journal of Pharmaceutical Sciences, vol. 58, 2014.
Ilvesaro, Joanna M. et al, "Toll-Like Receptor 9 Mediates CpG Oligonucleotide-Induced Cellular Invasion," Mol Cancer Res 2008;6(10). Oct. 2008.
Jones, Matthew R. et al., "Programmable materials and the nature of the DNA bond," Science 347, 1260901 (2015), DOI: 10.1126/science.1260901.
Communication pursuant to Article 94(3) EPC, issued in corresponding application No. EP17767464.5, dated Dec. 9, 2020, 5 pages.

| CpG | + | − | + | − |
| Cutting site | − | + | − | + |
| HhaI | − | − | + | + |

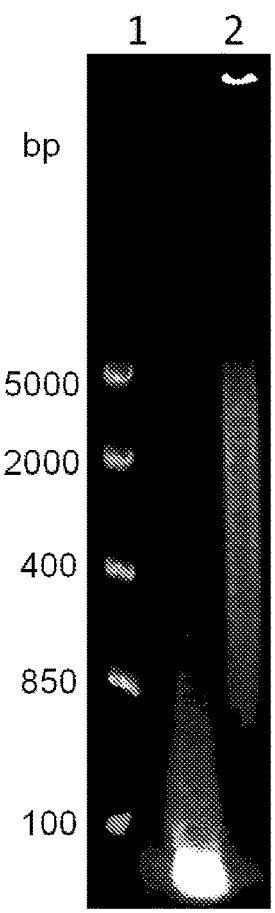
FIG. 10
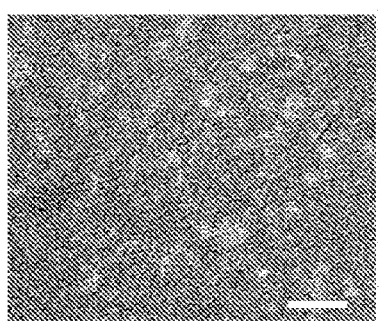 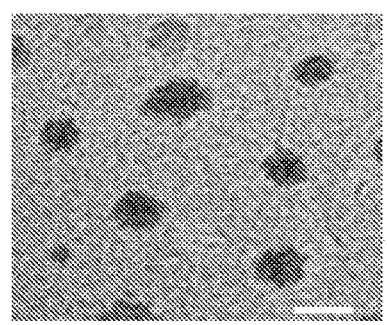 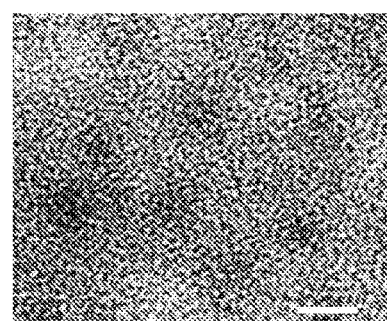
FIG. 11A   FIG. 11B   FIG. 11C

SEQUENCE LISTING

<160> NUMBER OF SEQ ID NOS: 3

<210> SEQ ID NO 1
<211> LENGTH: 72
<212> TYPE: DNA
<213> ORGANISM: Artificial Sequence
<220> FEATURE:
<223> OTHER INFORMATION: synthetic construct

<400> SEQUENCE: 1
gcgcgtcgtc gttcgaacga cgttgcgcgt cgtcgttcga acgacgttgc gcgtcgtcgt    60
tcgaacgacg tt    72

```
<210> SEQ ID NO 2
<211> LENGTH: 72
<212> TYPE: DNA
<213> ORGANISM: Artificial Sequence
<220> FEATURE:
<223> OTHER INFORMATION: synthetic construct

<400> SEQUENCE: 2
atatgtcgtc gttcgaacga cgttatataa cgtcgttcga acgacgttat atgtcgtcgt    60
tcgaacgacg tt                                                        72

<210> SEQ ID NO 3
<211> LENGTH: 72
<212> TYPE: DNA
<213> ORGANISM: Artificial Sequence
<220> FEATURE:
<223> OTHER INFORMATION: synthetic construct

<400> SEQUENCE: 3
gcgcgtatta tttcgaaata atttgcgcgt attatttata aataatttgc gcgtattatt    60
tataaataat tt                                                        72
```

NANOPARTICLES, CONTROLLED-RELEASE DOSAGE FORMS, AND METHODS FOR DELIVERING AN IMMUNOTHERAPEUTIC AGENT

CROSS REFERENCE TO RELATED APPLICATIONS

This application is a national stage application filed under 35 U.S.C. § 371 of PCT/US2017/022568 filed Mar. 15, 2017, which claims the benefit of U.S. Provisional Patent Application Ser. No. 62/308,513 filed Mar. 15, 2016, and 62/380,711 filed Aug. 29, 2016, the disclosures of which are expressly incorporated herein by reference.

FIELD

The present disclosure relates to nanoparticles, controlled-release dosage forms, and methods for the administration of an immunotherapeutic agent.

BACKGROUND

Surgical treatment is usually the most effective therapeutic method for solid tumors. However, many patients develop recurrent disease post-surgery, which can lead to significant morbidity as well as mortality for cancer patients (Paik, S. et al. New England Journal of Medicine 2004, 351, 2817). There is also a suggestion that the inflammatory processes during wound healing following tumor resection may promote cancer progression (Vakkila, J.; Lotze, M. T. Nat. Rev. Immunol. 2004, 4, 641; Coffey, J. C. et al. Lancet Oncol. 2003, 4, 760; Demicheli, R. et al. Ann. Oncol. 2008, mdn386; Grivennikov, S. I. et al. Cell 2010, 140, 883). Increasing amounts of evidence indicate that the perioperative inflammation induced by trauma may pose a high risk for the development of tumor reoccurrence, acceleration of local remaining tumor relapse as well as the promotion of tumor invasion and metastasis (Vakkila, J.; Lotze, M. T. Nat. Rev. Immunol. 2004, 4, 641; Ceelen, W. et al. Crit. Rev. Oncol. Hematol. 2014, 89, 16; Segatto, I. et al. Oncotarget 2014, 5, 6267; Antonio, N. et al. EMBO J. 2015, 34, 2219; Baker, D. et al. Surgery 1989, 106, 525).

There has been strong interest in the development of strategies to prevent cancer recurrence after surgery. Current approaches rely on established treatments including systemic chemotherapy and radiotherapy, which carry high toxicity profiles (Albain, K. et al. In ASCO Annual Meeting Proceedings 2005; Vol. 23, p 7014). Recent successes of cancer immunotherapy suggest that it can be utilized to prevent cancer recurrence (Stephan, S. B. et al. Nat. Biotechnol. 2015, 33, 97; Liu, Q. et al. Molecular Therapy 2009, 17, 2049). Immune regulatory checkpoint inhibitors, including anti-CTLA-4 and anti-PD-1, have shown significant results in treating various types of cancer, such as melanoma (Gubin, M. M. et al. Nature 2014, 515, 577; Pardoll, D. M. Nat. Rev. Cancer 2012, 12, 252; Wang, C. et al. Adv. Mater. 2014, 26, 8154; Curran, M. A. et al. Proc. Natl. Acad. Sci. U.S.A 2010, 107, 4275). Programmed cell death protein 1 (PD-1) is expressed by activated T cells. When activated T cells encounter programmed cell death 1 ligand 1 (PD-L1) up-regulated on cancer cells, T-cell effector functions are diminished (Pardoll, D. M. Nat. Rev. Cancer 2012, 12, 252). Therefore, inhibition of the interaction of PD1 on lymphocytes and PDL1 on tumour cells by anti-PD-1/PD-L1 antibodies can boost the immune response against cancer cells (Pardoll, D. M. Nat. Rev. Cancer 2012, 12, 252; Ribas, A. N. Engl. J. Med. 2015, 373, 1490).

Despite the positive clinical data of anti-PD-1 immunotherapy, it is not without limitations. One mechanism that may account for the limited treatment efficacy of anti-PD-1 antibody is the short circulation time of antibodies when intravenously infused into the body (Mitragotri, S. et al. Nat. Rev. Drug Discovery 2014, 13, 655; Patnaik, A. et al. In ASCO Annual Meeting Proceedings 2012; Vol. 30, p 2512; Topalian, S. L. et al. N. Engl. J. Med. 2012, 366, 2443). Moreover, the limited efficacy may also be secondary to the lack of co-stimulation in the setting where dendritic cells (DCs) encounter the tumor cells and T cells (Sabado, R. L.; Bhardwaj, N. Nature 2015, 519, 300). In addition, due to the amount of inhibitor needed, the cost of treatment is also unsustainably high. Side effects, such as autoimmune disorders from these agents can also be significant (Naidoo, J. et al. Ann. Oncol. 2015, mdv383; Hamid, O. et al. N. Engl. J. Med. 2013, 369, 134; Mellati, M. et al. Diabetes Care 2015, 38, e137). Furthermore, the response rate has significant potential to improve (Topalian, S. L. et al. Journal of Clinical Oncology 2014, 32, 1020). The objective response rate of anti-PD-1 therapy in metastatic melanoma is only 40% (Sharma, P. and J. P. Allison. Science 2015 Apr. 3, 348 (6230):56-61). Furthermore, even combining anti-PD-1 with anti-CTLA-4 produced a response in only ~50% of patients (Robert, C. et al. NEJM 2015, 372(26): 2521-2532). Thus, current methods of checkpoint blockade therapy may limit the beneficial effects of these immunotherapeutics in many patients. Therefore, there is a need for new methods to improve the clinical benefits of these immunomodulatory therapies while avoiding their untoward autoimmune effects.

SUMMARY

Disclosed herein are nanoparticles, controlled-release pharmaceutical dosage forms, and methods for the delivery of an immunotherapeutic agent. In one embodiment, the methods include the prevention of post-surgical tumor relapse.

In one aspect, disclosed herein is a controlled-release pharmaceutical dosage form comprising: a CpG oligodeoxynucleotide nano-cocoon, wherein the nano-cocoon encapsulates an immunotherapeutic agent and inflammation-responsive nanoparticles, wherein the nanoparticles encapsulate a restriction enzyme.

Tumor burden is the lowest after cancer surgery. Moreover, the local pro-inflammatory environment is conducive to immunotherapy. Thus, the inventors have developed an innovative delivery carrier (self-assembling DNA nano-cocoons (DNCs)) for the controlled release of a loaded immunotherapeutic agent and CpG oligodeoxynucleotides (ODNs) in response to inflammation conditions. CpG ODNs, trigger cells that express Toll-like receptor 9, including human plasmacytoid dendritic cells (pDCs), have potent immunostimulatory effects and can enhance the anti-cancer activity of a variety of cancer treatments.

The self-assembling DNA nano-cocoons can be made through an enzymatic rolling circle amplification (RCA) method specifically based on a template of interest. In one embodiment, the DNA nano-cocoon is encoded with a CpG sequence. The carrier (designated as DNA "nano-cocoons", DNCs) can be assembled by a long-chain single-stranded DNA (ssDNA). The DNA contains repeating interval CpG sequences and cutting sites for a restriction enzyme. In one embodiment the restriction enzyme is HhaI, which is capable of digesting DNCs and subsequently generating CpG ODN fragments.

To make the release event bio-responsive, a restriction enzyme (for example, HhaI) can be caged into inflammation-responsive nanoparticles, for example triglycerol monostearate (TGMS) nanoparticles (TGMS NPs), and attached to DNA nano-cocoons (DNCs). TGMS is an amphiphile whose ester linkage enables cleavage by esterases and matrix metalloproteinases (MMPs) that are highly expressed at wound sites for developmental tissue remodeling. Triggered by the inflammatory condition occurring in the wound site of the tumor resection incision, TGMS can be enzymatically cleaved, thereby disassembling the triglycerol monostearate nanoparticle cage and releasing the restriction enzyme, which can further sequentially convert DNA nanococoon (DNC) to CpG oligodeoxynucleotides (ODNs) and release the immunotherapeutic agent (for example, aPD1) as well. The combined action of the controlled-release CpG ODNs and the immunotherapeutic agent can facilitate induction of durable and specific anti-tumor T-cell responses in a melanoma model, while avoiding the toxic peak levels in the body.

In another aspect, disclosed herein is a method of chemoprevention comprising: administering to a host a controlled-release pharmaceutical dosage form in an amount sufficient to prevent the recurrence of a cancer; wherein the controlled-release pharmaceutical dosage form comprises a CpG oligodeoxynucleotide nano-cocoon, wherein the nanococoon encapsulates an immunotherapeutic agent and inflammation-responsive nanoparticles, wherein the nanoparticles encapsulate a restriction enzyme.

In one embodiment, the immunotherapeutic agent is selected from an anti-PD1 antibody, an anti-PDL1 antibody, an anti-CTLA4 antibody, or a combination thereof. In one embodiment, the immunotherapeutic agent is an anti-PD1 antibody. In one embodiment, the anti-PD1 antibody is nivolumab. In one embodiment, the anti-PD1 antibody is pembrolizumab.

In another embodiment, the immunotherapeutic agent is an anti-CTLA4 antibody. In one embodiment, the anti-CTLA4 antibody is ipilimumab. In one embodiment, the immunotherapeutic agent is an anti-PD1 antibody in combination with an anti-CTLA4 antibody.

In a further embodiment, the inflammation-responsive nanoparticles comprise triglycerol monostearate (TGMS). In an additional embodiment, the restriction enzyme is HhaI.

In one embodiment, the method of chemoprevention is used for preventing the recurrence of a cancer, wherein the cancer is a solid tumor. In one embodiment, the cancer is melanoma.

In yet other aspects, immunotherapeutic agents may be delivered in nanoparticles comprising hyaluronic acid covalently conjugated with 1-methyl-DL-tryptophan, which is an inhibitor of IDO.

In another aspect, disclosed herein is a nanoparticle comprising: hyaluronic acid covalently conjugated with 1-methyl-DL-tryptophan, wherein the nanoparticle encapsulates an immunotherapeutic agent.

In another aspect, disclosed herein is a method for treating or preventing a disease in a subject in need thereof, comprising:
providing a microneedle patch to a subject, wherein the microneedle patch comprises:
a plurality of microneedles each having a base end and a tip;
a substrate to which the base ends of the microneedles are attached or integrated;
nanoparticles, wherein the nanoparticles comprise hyaluronic acid covalently conjugated with 1-methyl-DL-tryptophan, and wherein the nanoparticles encapsulate an immunotherapeutic agent;
inserting the microneedles into a biological barrier, wherein the immunotherapeutic is released into the subject in a controlled-release manner.

In one embodiment, the immunotherapeutic agent is selected from an anti-PD1 antibody, an anti-PDL1 antibody, an anti-CTLA4 antibody, or a combination thereof. In one embodiment, the immunotherapeutic agent is an anti-PD1 antibody. In one embodiment, the anti-PD1 antibody is nivolumab. In one embodiment, the the anti-PD1 antibody is pembrolizumab. In one embodiment, the immunotherapeutic agent is an anti-CTLA4 antibody. In one embodiment, the anti-CTLA4 antibody is ipilimumab.

In one embodiment, the disease is a cancer. In one embodiment, the cancer is melanoma. In one embodiment, the biological barrier is skin.

BRIEF DESCRIPTION OF THE FIGURES

The accompanying figures, which are incorporated in and constitute a part of this specification, illustrate several aspects described below.

(FIG. 1A) CpG-sequence containing DNA nano-cocoon (DNC) loaded with anti-PD1 antibody and caged restriction enzyme for inflammation-trigged fragmentation of DNC for releasing both CpG DNA and aPD1. (FIG. 1B) A schematic representation of in vivo tumor immunotherapy after primary tumor resection, local injection and treatment of DNC-based delivery system. (FIG. 1C) Released CpG DNA activates dendritic cells (DCs) to drive T cell response with aPD1 for PD 1 blockade.

(FIG. 2A) TEM imaging of HhaI-TGMS-DNCs-aPD1 nanocomposites (Scale bar=500 nm). Inset: zoom-in image (Scale bar=200 nm). (FIG. 2B) Dynamic light scattering characterization of HhaI-TGMS-DNCs-aPD1 nanocomposites. (FIG. 2C) Schematic of LPS activation of RAW264.7 macrophages for mimicking inflammatory conditions. (FIG. 2D) Gel electrophoresis of HhaI-TGMS-DNCs-aPD1 nanocomposites incubated with cell culture supernatant from the activated and non-activated macrophages at the difference time points (Lane 0, 0 min; Lane 1, 30 min; Lane 2, 1 h; Lane 3, 2 h; Lane 4, 4 h; Lane 5, 6 h; Lane M, DNA ladder). (FIGS. 2E-2F) Percentage of DNA and aPD1 released from TGMS-DNC nanocomposites when incubated with cell culture supernatant from activated and non-activated macrophages at different time points. (FIGS. 2G-2H) AFM images and hydrodynamic size of HhaI-TGMS-DNCs-aPD1 nanocomposites when incubated with cell culture supernatant from non-activated macrophages. (FIGS. 2I-2J) AFM images and hydrodynamic size of HhaI-TGMS-DNCs-aPD1 nanocomposites when incubated with cell culture supernatant from activated macrophages (Scale bar=500 nm). The error bars are based on the standard deviations (SD) of triplicated samples.

(FIG. 3A) In vivo bioluminescence imaging of the B16F10 tumors of the different groups after removal of primary tumor. (G1, PBS control; G2, HhaI-TGMS-DNCs; G3, HhaI-TGMS-cDNCs-aPD1; G4, free aPD1/free CpG nucleotides; G5, HhaI-TGMS-DNCs-aPD1) (FIG. 3B) Quantified tumor signals and (FIG. 3C) mean tumor growth of different groups of mice after various treatments indicated. Pie chart shows percent CR rate (orange) (n=10). The black arrow indicates the surgery time. (FIG. 3D) Representative plots of T cells in relapsed tumors analyzed by the flow cytometry. (Gated on CD3+ T cells). (FIG. 3E) Representative plots of activated CD8 T cells (CD44+CD62L−) in relapsed tumors analyzed by the flow cytometry (gated on CD8+ T cells). (FIG. 3F) Immunofluorescence of relapsed tumors showed CD4+ T cells and CD8+ T cells infiltration (Scale bar=100 µm). (FIG. 3G) Absolute number of the activated CD8 cells present in tumors for the study shown in C&D. (FIG. 3H) Ratios of the tumor-infiltrating CD8+ T cells and effective CD4+ T cells over regulatory T cells in the relapsed tumors upon various treatments. Statistical significance was calculated by 2-way ANOVA using the Tukey post-test. P value: *, $P<0.05$; , $P<0.01$; *$P<0.005$.

(FIG. 4A) In vivo bioluminescence imaging of the B16F10 metastasis of different groups after removing of primary tumors at different time points. (G1, PBS control; G2, HhaI-TGMS-DNCs; G3, HhaI-TGMS-cDNCs-aPD1; G4, free aPD1/free CpG nucleotides; G5, HhaI-TGMS-DNCs-aPD1). (FIG. 4B) Quantified tumor signals according to A. Every line represents one animal and each dot shows the whole animal photon count. (FIG. 4C) Kaplan Meier survival curves for treated and control mice. Shown are ten mice per treatment group. (FIG. 4D) IFN-γ CD8 CTLs T-cell in splenocytes of mice with various treatments indicated in A. (FIG. 4E) Quantified IFN-γ CD8 CTL T-cell in splenocytes from three independent experiments. (FIG. 4F) CTL-mediated immune responses measured by incubating restimulated splenocytes with B16 tumor cells. The error bars are based on the standard error of the mean (SEM) of three mice.

(FIG. 5A) AFM image of DNCs. The scale bar is 500 nm. (FIG. 5B) TEM image of DNCs. The scale bar is 200 nm. (FIG. 5C) Hydrodynamic size of DNC as determined by dynamic light scattering (DLS).

(FIG. 6A) Gel electrophoresis of DNC (1) and after being treated with HhaI (2). (FIG. 6B) Secretion of IL-6 and TNF-α by RAW 264.7 macrophages as determined by ELISA.

FIG. 10. Gel electrophoresis of DNA nano-cocoons (DNCs) treated with (1) HhaI and (2) TGMS@HhaI.

FIGS. 11A-11C. TEM image of free enzyme (FIG. 11A), HhaI@TGMS NPs (FIG. 11B) and HhaI@TGMS NPs after incubation at inflammation condition for 2 h (FIG. 11C). (Scale bar=50 nm)

(FIG. 12A) Gel electrophoresis of HhaI-TGMS-DNCs-aPD1 nanocomposites incubated with MMP9 (200 ng/mL) in PBS at different time points. (FIGS. 12B & FIG. 12C) Percentage of DNA and aPD1 released from TGMS-DNC nanocomposites when incubated with MMP9, lipase or PBS control at different time points.

(FIG. 18A) (Top panel) Schematic illustration of encapsulation and release of IDO inhibitor 1-MT and aPD1 from self-assembled m-HA nanoparticles (NPs) (i) Self-assembly of the m-HA. (ii) Dissociation of the HA-NP by HAase. (Bottom panel) Schematic illustration of the therapeutics delivery using microneedles and the enhanced immune responses at the skin tumor site. (FIG. 18B) The average hydrodynamic sizes (left panel) and TEM imaging (right panel) of the self-assembled HA-NPs. (FIG. 18C) The average hydrodynamic sizes (left panel) and TEM imaging (right panel) of the dissociated HA-NPs (scale bar: 200 nm). (FIG. 18D) Percentage of aPD1 released from NPs with and without addition of HAase. (FIG. 18E) Percentage of 1-MT released from NPs with and without addition of HAase. The error bars were based on the standard deviations (SD) of triplicated samples.

(FIG. 19A) Photograph of a representative MN patch (scale bar: 1 mm). (FIG. 19B) SEM image of the MN patch (scale bar: 400 µm). (FIG. 19C) Fluorescence imaging of a representative MN patch that contained FITC-aPD1 loaded NPs (scale bar: 400 µm). (FIG. 19D) Mouse dorsum skin (the area within the red line) was transcutaneously treated with one MN patch. (FIG. 19E) The image of the trypan blue stained mouse skin showing the penetration of the MN patch into the skin (scale bar: 1 mm). (FIG. 19F) In vivo bioluminescence imaging of the MN-treated melanoma-bearing mice at different time points. The luminescence showed the MN patch loaded with aPD1 and Cy5.5-labeled 1-MT-HA that self-assembled into HA-NP (top panel), or free Cy5.5-labeled 1-MT (bottom panel). (FIG. 19G) The distribution of Cy5.5-labeled 1-MT in major organs three days after the administrations of MNs formulated with aPD1 and 1-MT-HA (top panel), or free 1-MT (bottom panel). (FIG. 19H) Quantitative biodistributions of Cy5.5-labeled 1-MT. Significantly higher (two population t-test, $P<0.01$) amounts of Cy5.5 with longer duration were detected in the tumors treated with 1-MT-HA loaded MNs (top panel) compared to free 1-MT loaded MNs (bottom panel). The error bars were based on the standard deviations (SD) of triplicated samples. (FIG. 19I) Immunofluorescence staining of the tumors three days after the treatments with aPD1/1-MT-HA loaded MNs (top panel) compared to the free aPD1/1-MT loaded MNs (bottom panel) (red: aPD1, blue: nucleus) (scale bar: 100 µm).

(FIG. 20A) In vivo bioluminescence imaging of the B16F10 melanoma of different groups at different time points after the MN treatment. The melanoma-bearing mice were grouped and transcutaneously exposed to different samples by a single administration to the tumor site, blank MN patch (G1), i.v. injection of aPD1 (G2), i.t. injection of aPD1 and 1-MT (G3), aPD1 loaded MN patch (G4), 1-MT loaded MN patch (G5) and NPs-loaded MN patch (G6). (FIG. 20B) Quantified individual tumor sizes of different groups of mice after various treatments were indicated. (FIG. 20C) Average tumor areas for the treated mice. (FIG. 20D) Survival curves for the treated and control mice. (FIG. 20E) Average body weights for the treated and control mice. Shown were eight mice per treatment group. The error bars were based on the standard deviations (SD) of eight samples.

(FIG. 21A) Representative melanoma images from mice immediately before the collection of tumor-infiltrating lymphocytes. The melanoma-bearing mice were grouped and transcutaneously exposed to different samples by a single administration to the tumor site, blank MN patch (G1), i.v. injection of aPD1 (G2), i.t. injection of aPD1 and 1-MT (G3), aPD1 loaded MN patch (G4), 1-MT loaded MN patch (G5) and NPs loaded MN patch (G6) (from bottom to top). (FIG. 21B) Immunofluorescence of the residual tumors showed CD4+ T cells and CD8+ T cells infiltration in G6 (top panel), or G1 (bottom panel) groups (scale bar: 100 µm). (FIG. 21C) H&E staining of representative melanoma at the time of the collection of tumor-infiltrating lymphocytes. (FIG. 21D) Tumor weights, absolute numbers of CD3+ cells per milligram of tumor, absolute numbers of CD8+ cells per milligram of tumor, percentage of CD4+ regulatory T cells, percentage CD8+ T cells of total regulatory T cells and percentage CD8+ T cells of total regulatory T cells. Statistical significance was calculated by one-way ANOVA using the Tukey post-test (* P<0.05;  P<0.01; *P<0.005).

DETAILED DESCRIPTION

Figure 1A:
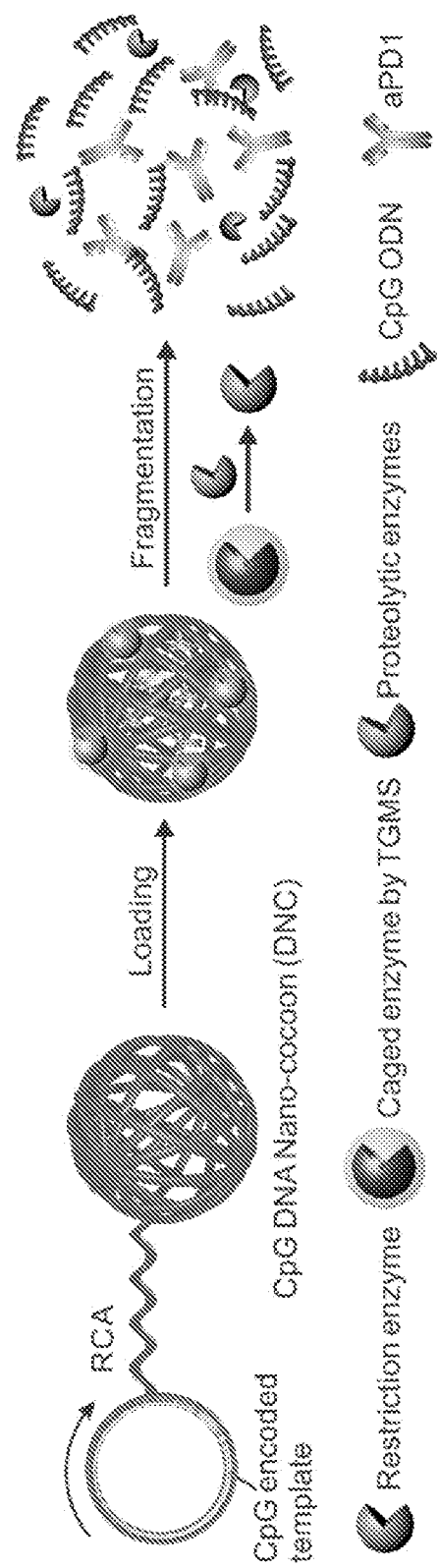
FIGS. 1A-1C. Schematic illustration of delivery of CpG and anti-PD1 antibody (aPD1) by DNA nano-cocoon under an inflammation condition.

Cancer recurrence after surgical resection remains a significant challenge in cancer management. Disclosed herein are controlled-release pharmaceutical dosage forms and methods for the delivery of CpG oligodeoxynucleotides and an immunotherapeutic agent. In one embodiment, the methods include the prevention of post-surgical tumor relapse.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Activities" of a protein, including those relating to "bioactivity," include, for example, transcription, translation, intracellular translocation, secretion, phosphorylation by kinases, cleavage by proteases, and/or homophilic and heterophilic binding to other proteins.

The term "administering" refers to an administration that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. Administering can be performed using transdermal microneedle-array patches. The term "parenteral" includes subcutaneous, intravenous, intramuscular, intra-articular, intra-synovial, intrasternal, intrathecal, intrahepatic, intralesional, and intracranial injections or infusion techniques.

"Biocompatible" generally refers to a material and any metabolites or degradation products thereof that are generally non-toxic to the recipient and do not cause any significant adverse effects to the subject.

A "composition" is intended to include a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

As used herein, "conjugated" refers to a non-reversible binding interaction.

As used herein, "displace" refers to interrupting a molecular or chemical interaction between, for example, a protein domain and a peptide, a protein domain and a chemical, a protein domain and a nucleic acid sequence by a chemical, peptide, or nucleic acid having affinity for that specific protein domain than the peptide, chemical, or nucleic acid being displaced.

A "linker" as used herein refers to a molecule that joins adjacent molecules. Generally a linker has no specific biological activity other than to join the adjacent molecules or to preserve some minimum distance or other spatial relationship between them. In some cases, the linker can be selected to influence or stabilize some property of the adjacent molecules, such as the folding, net charge, or hydrophobicity of the molecule.

The terms "peptide," "protein," and "polypeptide" are used interchangeably to refer to a natural or synthetic molecule comprising two or more amino acids linked by the carboxyl group of one amino acid to the alpha amino group of another.

The term "carrier" or "pharmaceutically acceptable carrier" means a carrier or excipient that is useful in preparing a pharmaceutical or therapeutic composition that is generally safe and non-toxic, and includes a carrier that is acceptable for veterinary and/or human pharmaceutical or therapeutic use. As used herein, the terms "carrier" or "pharmaceutically acceptable carrier" encompasses can include phosphate buffered saline solution, water, emulsions (such as an oil/water or water/oil emulsion) and/or various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers. As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "therapeutically effective amount" or "therapeutically effective dose" refer to the amount of a composition, such as an immunotherapeutic agent, that will elicit the biological or medical response of a tissue, system, animal, or human that is being sought by the researcher, veterinarian, medical doctor or other clinician over a generalized period of time. In some instances, a desired biological or medical response is achieved following administration of multiple dosages of the composition to the subject over a period of days, weeks, or years.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection.

The term "specifically binds," as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "immune checkpoint inhibitor" or "immunotherapeutic" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD 80 and CD6; and PD1 with its ligands PDL1 and PDL2 (Pardon, Nature Reviews Cancer 12: 252-264, 2012). These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "mixture" can include solutions in which the components of the mixture are completely miscible, as well as suspensions and emulsions, in which the components of the mixture are not completely miscible.

As used herein, the term "subject" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

As used herein, the term "controlled-release" or "controlled-release drug delivery" or "sustained-release" refers to release or administration of a drug from a given dosage form in a controlled fashion in order to achieve the desired pharmacokinetic profile in vivo. An aspect of "controlled" drug delivery is the ability to manipulate the formulation and/or dosage form in order to establish the desired kinetics of drug release.

The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

As used herein, the term "nano-cocoon" or "DNA nano-cocoon (DNC)" refers to a nanoparticle made of DNA. The DNA nano-cocoon can be used for the controlled release of a therapeutic agent, for example, an immunotherapeutic agent. In one embodiment, the DNA nano-cocoon is self-assembling and can be made through an enzymatic rolling circle amplification (RCA) method based on a DNA template of interest and is assembled by a long-chain single-stranded DNA (ssDNA).

As used herein, the term "CpG oligodeoxynucleotide" refers to an oligodeoxynucleotide comprising at least one CpG motif. The CpG motif contains unmethylated cytosine-guanine dinucleotide linked by a phosphate bond and the CpG motif activates the immune response.

Delivery of Immunotherapeutic Agents: Controlled-Release Dosage Forms Using DNA Nano-Cocoons The inventors have developed a new cancer immunotherapy agent which can be used for the prevention of post-surgical tumor relapse. Tumor burden is the lowest after cancer surgery. Moreover, the local pro-inflammatory environment is conducive to immunotherapy. Thus, the inventors have developed an innovative delivery carrier for the controlled release of a loaded immunotherapeutic agent and CpG oligodeoxynucleotides (ODNs) in response to inflammation conditions. CpG ODNs, trigger cells that express Toll-like receptor 9, including human plasmacytoid dendritic cells (pDCs), have potent immunostimulatory effects and can enhance the anti-cancer activity of a variety of cancer treatments.

The self-assembling DNA nano-cocoons can be made through an enzymatic rolling circle amplification (RCA) method specifically based on a template of interest. In one embodiment, the DNA nano-cocoon is encoded with a CpG sequence. The carrier (designated as DNA "nano-cocoons", DNCs) is assembled by a long-chain single-stranded DNA (ssDNA). The DNA contains repeating interval CpG sequences and cutting sites for a restriction enzyme. In one embodiment the restriction enzyme is HhaI, which is capable of digesting DNCs and subsequently generating CpG ODN fragments.

To make the release event bio-responsive, the restriction enzyme (for example, HhaI) can be caged into inflammation-responsive nanoparticles, for example triglycerol monostearate (TGMS) nanoparticles (TGMS NPs), and attached to DNCs. TGMS is an amphiphile whose ester linkage enables cleavage by esterases and matrix metalloproteinases (MMPs) that are highly expressed at the wound sites for developmental tissue remodeling. Triggered by the inflammatory condition occurring in the wound site of the tumor resection incision, TGMS can be enzymatically cleaved, thereby disassembling the cage and releasing the restriction enzyme, which can further sequentially convert DNCs to CpG ODNs and release the immunotherapeutic agent (for example, aPD1) as well.

In one aspect, disclosed herein is a controlled-release pharmaceutical dosage form comprising: a CpG oligodeoxynucleotide nano-cocoon, wherein the nano-cocoon encapsulates an immunotherapeutic agent and inflammation-responsive nanoparticles, wherein the nanoparticles encapsulate a restriction enzyme.

In one embodiment, the immunotherapeutic agent is selected from an anti-PD1 antibody, an anti-PDL1 antibody, an anti-CTLA4 antibody, or a combination thereof. In one embodiment, the immunotherapeutic agent is an anti-PD1 antibody. In one embodiment, the anti-PD1 antibody is nivolumab. In one embodiment, the anti-PD1 antibody is pembrolizumab.

In another embodiment, the immunotherapeutic agent is an anti-CTLA4 antibody. In one embodiment, the anti-CTLA4 antibody is ipilimumab. In one embodiment, the immunotherapeutic agent is an anti-PD1 antibody in combination with an anti-CTLA4 antibody. In one embodiment, the restriction enzyme is HhaI. In some embodiments, the restriction enzyme cleaves single-stranded DNA. Examples of restriction enzymes that can cleave single stranded DNA include, but are not limited to, HhaI, HinpII, MnlI, HaeIII, HpaII, MboII. HinfI, HgaI, BstNI, DdeI, and TaqI.

In one embodiment, the inflammation-responsive nanoparticles comprise triglycerol monostearate (TGMS). Additional triglycerol monoalkanoates that can comprise the inflammation-responsive nanoparticles can include, for example, triglycerol monopalmitate, triglycerol monodecanoate, triglycerol monolaurate, triglycerol monostearate, triglycerol monocaprylate, triglycerol monomyristate, triglycerol monooleate, and/or any combination thereof.

Self-assembled DNA nanostructures can be developed with precisely controlled size and architecture. Because of DNA's intrinsic biocompatibility and degradability, DNA nanostructures can be used for drug delivery. Numerous cargoes, for example, small-molecule drugs, small interfering RNA (siRNA), the immunostimulatory oligonucleotide CpG, photosensitizers, and proteins, can be delivered intracellularly by DNA nanocarriers. In addition, DNA-based carriers can be functionalized either by hybridizing a targeting moiety onto the nanostructure or programming a targeting aptamer into the DNA chain for targeted drug delivery.

In one aspect of the invention, disclosed herein is a method of chemoprevention comprising: administering to a host a controlled-release pharmaceutical dosage form in an amount sufficient to prevent the recurrence of a cancer; wherein the controlled-release pharmaceutical dosage form comprises a CpG oligodeoxynucleotide nano-cocoon, wherein the nano-cocoon encapsulates an immunotherapeutic agent and inflammation-responsive nanoparticles, wherein the nanoparticles encapsulate a restriction enzyme.

In one aspect of the invention, disclosed herein is a method of chemoprevention comprising:
providing a microneedle patch to a subject, wherein the microneedle patch comprises:
  a plurality of microneedles each having a base end and a tip;
  a substrate to which the base ends of the microneedles are attached or integrated;
  a CpG oligodeoxynucleotide nano-cocoon, wherein the nano-cocoon encapsulates an immunotherapeutic agent and inflammation-responsive nanoparticles, wherein the nanoparticles encapsulate a restriction enzyme; and
inserting the microneedles into a biological barrier, wherein the immunotherapeutic is released into the subject in a controlled-release manner.

In another aspect, disclosed herein is a method for treating or preventing a disease in a subject in need thereof, comprising:
providing a microneedle patch to a subject, wherein the microneedle patch comprises:
  a plurality of microneedles each having a base end and a tip;
  a substrate to which the base ends of the microneedles are attached or integrated;
  a CpG oligodeoxynucleotide nano-cocoon, wherein the nano-cocoon encapsulates an immunotherapeutic agent and inflammation-responsive nanoparticles, wherein the nanoparticles encapsulate a restriction enzyme; and inserting the microneedles into a biological barrier, wherein the immunotherapeutic is released into the subject in a controlled-release manner.

In one embodiment, the immunotherapeutic agent is selected from an anti-PD1 antibody, an anti-PDL1 antibody, an anti-CTLA4 antibody, or a combination thereof. In one embodiment, the immunotherapeutic agent is an anti-PD1 antibody. In one embodiment, the anti-PD1 antibody is nivolumab. In one embodiment, the anti-PD1 antibody is pembrolizumab.

In another embodiment, the immunotherapeutic agent is an anti-CTLA4 antibody. In one embodiment, the anti-CTLA4 antibody is ipilimumab. In one embodiment, the immunotherapeutic agent is an anti-PD1 antibody in combination with an anti-CTLA4 antibody.

In a further embodiment, the inflammation-responsive nanoparticles comprise triglycerol monostearate (TGMS). In an additional embodiment, the restriction enzyme is HhaI.

In an additional embodiment, disclosed herein is a method of chemoprevention comprising: administering to a host a controlled-release pharmaceutical dosage form in an amount sufficient to inhibit the progression of a precancerous lesion to a cancer; wherein the controlled-release pharmaceutical dosage form comprises a CpG oligodeoxynucleotide nano-cocoon, wherein the nano-cocoon encapsulates an immunotherapeutic agent and inflammation-responsive nanoparticles, wherein the nanoparticles encapsulate a restriction enzyme.

In one embodiment, the method of chemoprevention is used for preventing the recurrence of a cancer. The active compounds and methods described herein are useful for the prevention or recurrence of excised solid tumors. In one embodiment, the cancer recurrence to be prevented is melanoma.

As contemplated herein, the cancer recurrence to be prevented or treated can be a primary tumor. In one aspect, the methods described herein are used to prevent solid tumor recurrence, for example, melanoma, lung cancer (including lung adenocarcinoma, basal cell carcinoma, squamous cell carcinoma, large cell carcinoma, bronchioloalveolar carcinoma, bronchogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas, leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

Delivery of Immunotherapeutic Agents: 1-methyl-DL-tryptophan Nanoparticles

In yet other aspects, immunotherapeutic agents may be delivered in nanoparticles comprising hyaluronic acid covalently conjugated with 1-methyl-DL-tryptophan, which is an inhibitor of indoleamine 2,3-dioxygenase (IDO).

In one aspect, disclosed herein is a nanoparticle comprising: hyaluronic acid covalently conjugated with 1-methyl-DL-tryptophan, wherein the nanoparticle encapsulates an immunotherapeutic agent.

In another aspect, disclosed herein is a method for treating or preventing a disease in a subject in need thereof, comprising:

providing a microneedle patch to a subject, wherein the microneedle patch comprises:
  a plurality of microneedles each having a base end and a tip;
  a substrate to which the base ends of the microneedles are attached or integrated;
  nanoparticles, wherein the nanoparticles comprise hyaluronic acid covalently conjugated with 1-methyl-DL-tryptophan, and wherein the nanoparticles encapsulate an immunotherapeutic agent;

inserting the microneedles into a biological barrier, wherein the immunotherapeutic is released into the subject in a controlled-release manner.

In one aspect of the invention, disclosed herein is a method of chemoprevention comprising:

providing a microneedle patch to a subject, wherein the microneedle patch comprises:
  a plurality of microneedles each having a base end and a tip;
  a substrate to which the base ends of the microneedles are attached or integrated;
  nanoparticles, wherein the nanoparticles comprise hyaluronic acid covalently conjugated with 1-methyl-DL-tryptophan, and wherein the nanoparticles encapsulate an immunotherapeutic agent;

inserting the microneedles into a biological barrier, wherein the immunotherapeutic is released into the subject in a controlled-release manner.

In one embodiment, the immunotherapeutic agent is selected from an anti-PD1 antibody, an anti-PDL1 antibody, an anti-CTLA4 antibody, or a combination thereof. In one embodiment, the immunotherapeutic agent is an anti-PD1 antibody. In one embodiment, the anti-PD1 antibody is nivolumab. In one embodiment, the the anti-PD1 antibody is pembrolizumab. In one embodiment, the immunotherapeutic agent is an anti-CTLA4 antibody. In one embodiment, the anti-CTLA4 antibody is ipilimumab.

In one embodiment, the nanoparticles are administered in a method of treating or preventing a cancer. In one embodiment, the disease is a cancer. In one embodiment, the cancer is melanoma. In one embodiment, the biological barrier is skin.

In one embodiment, the nanoparticles can be administered in a method of chemoprevention and is used for preventing the recurrence of a cancer. The active compounds and methods described herein are useful for the prevention or recurrence of excised solid tumors. In one embodiment, the cancer recurrence to be prevented is melanoma. Additional examples of solid tumors are described above.

Immunotherapeutic Agents (Immune Checkpoint Inhibitors and Immunologic Adjuvants)

There are a number of immunotherapeutic agents that are known to inhibit immune checkpoint proteins (immune checkpoint inhibitors). Known immune checkpoint proteins include CTLA-4, PD1 and its ligands PD-L1 and PD-L2 and in addition LAG-3, BTLA, B7H3, B7H4, 4-1BB (CD137), TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g. Pardon, 2012, Nature Rev Cancer 12:252-264).

An immune checkpoint inhibitor is any compound inhibiting the function of an immune checkpoint protein. Inhibition includes reduction of function and/or full blockade. In one embodiment, the immune checkpoint protein is a human immune checkpoint protein. Thus, the immune checkpoint protein inhibitor can be an inhibitor of a human immune checkpoint protein. Immune checkpoint proteins are described in the art (see for example, Pardoll, 2012. Nature Rev. Cancer 12: 252-264).

Preferred immune checkpoint protein inhibitors are antibodies that specifically recognize immune checkpoint proteins. A number of PD1, PDL-1, PD-L2, CTLA-4, BTLA, B7H4, 4-1BB (CD137), TIM3 and KIR inhibitors are known and in analogy of these known immune checkpoint protein inhibitors may be administered using the devices and methods disclosed herein.

Examples of PD-1 inhibitors include without limitation humanized antibodies blocking human PD-1 such as pembrolizumab (formerly lambrolizumab), or pidilizumab as well as fully human antibodies such as nivolumab (previously known as MDX-1106 or BMS-936558). Ipilimumab is a fully human CTLA-4 blocking antibody presently marketed under the name Yervoy (Bristol-Myers Squibb). A second CTLA-4 inhibitor is tremelimumab. In one embodiment, the immunotherapeutic is nivolumab.

In addition, immune checkpoint inhibitors may include without limitation humanized or fully human antibodies blocking PD-L1 such as MEDI-4736 (disclosed in WO2011066389 A1), MPDL328 OA (disclosed in U.S. Pat. No. 8,217,149 B2) and MIH1 (Affymetrix obtainable via eBioscience (16.5983.82)) and other PD-L1 inhibitors presently under investigation. Additional antibodies to PD-L1 include atezolizumab and durvalumab.

In one embodiment, KIR inhibitors are administered. Lirilumab is a human monoclonal antibody that binds to KIR2DL1/2L3. In one embodiment, inhibitors of 4-1BB (CD137) are administered. Urelumab targets the extracellular domain of CD137.

In one embodiment, an immune checkpoint inhibitor is preferably selected from a CTLA-4, PD-1 or PD-L1 inhibitor, such as selected from the known CTLA-4, PD-1 or PD-L1 inhibitors mentioned above (ipilimumab, tremelimumab, pembrolizumab, nivolumab, pidillizumab, atezolizumab, durvalumab, AMP-244, MEDI-4736, MPDL328 OA, MIH1), or combinations thereof.

The selection of an immune checkpoint inhibitor from PD1 and PD-L1 inhibitors, such as a known PD-1 or PD-L1 inhibitor mentioned above, is more preferred and most preferably a selection is made from a PD-1 inhibitor, such as a known PD1 inhibitor mentioned above. In preferred embodiments, the PD1 inhibitor is nivolumab or pembrolizumab or another antagonist antibody against human PD1.

In one embodiment, the immunotherapeutic agent can be administered in combination with an immunological adjuvant. An immunologic adjuvant is any substance that acts to accelerate, prolong, or enhance immune responses when used in combination with other immunotherapeutic agents (for example, monophosphoryl lipid A (MPLA), aluminum salt (Alum), unmethylated CpG dinucleotide-containing DNA) (e.g. Lim, Y T. Clin Exp Vaccine Res. 2015 January; 4(1): 54-58).

EXAMPLES

The following examples are set forth below to illustrate the compositions, devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Inflammation-Triggered Cancer Immunotherapy by Programmed Delivery of CpG and Anti-PD1 Antibody Cell Lines.

The mouse melanoma cell line B16F10 was purchased from the American Type Culture Collection. For bioluminescent in vivo tumor imaging, B16F10-luc cells were gifts from Dr. Leaf Huang at UNC. The cells were maintained in Dulbecco's Modified Eagle Medium (Gibco, Invitrogen) supplemented with 10% fetal bovine serum (Invitrogen, Carlsbad, Calif.), 100 U/mL penicillin (Invitrogen) and 100 U/mL streptomycin (Invitrogen). RAW 264.7 murine macrophages were purchased from the American Type Culture Collection and maintained in RPMI 1640 Medium (Gibco, Invitrogen) supplemented with 10% fetal bovine serum (Invitrogen, Carlsbad, Calif.), 100 U/mL penicillin (Invitrogen) and 100 m/mL streptomycin (Invitrogen).

Antibodies.

aPD-1 (anti-PD-1 antibody) used in vivo was purchased from Biolegend Inc. Staining antibodies included CD3, CD4, CD8, CD62L, CD44 (Thermo Scientific), intracellular IFN-γ and Foxp3 (eBioscience) for FACS analysis following manufacturers' instructions. Stained cells were analyzed on a Calibur FACS instrument (BD), and analyzed using flowjo software (version 10).

Preparation of Enzyme/TGMS-PD1/DNA Nano-Cocoon Nanocomplex.

For preparation of DNA nano-cocoons, rolling circle amplification (RCA) was used to prepare the DNA nano-cocoon according to previous reports. A 5'-phosphorylated ssDNA template (Integrated DNA Technologies Inc.) was cyclized into a circular ssDNA template with CircLigase II ssDNA ligase (Epicenter) according to manufacture's instructions. Briefly, 10 pmol ssDNA template was added into a 20 µL reaction mixture containing 2.5 mM MnCl2, 1 M betaine and 5 U/µL CircLigase II ssDNA ligase. After incubation at 60° C. for 1 h, the cyclized template was treated with Exonuclease I (1 U/µL) at 37° C. for 45 min and followed by heat inactivation at 80° C. for 15 min. The resultant cyclized ssDNA template was hybridized with 0.5 µM primer in a 1×isothermal amplification buffer (20 mM Tris-HCl pH 8.8, 10 mM (NH4)2SO4, 50 mM KCl, 2 mM MgSO4, 0.1% Tween 20) containing 0.2 mM dNTP at 95° C. for 5 min. After cooling the template-primer hybridized solution to room temperature, Bst 2.0 DNA polymerase (New England BioLabs Inc.) was added to a final concentration of 0.2 U/µL and the RCA was performed at 60° C. for 17 h followed by heat inactivation at 80° C. for 20 min. The obtained DNA nano-cocoon was dialyzed against TE buffer (10 mM Tris pH 8.0, 1 mM EDTA) at room temperature in a dialysis unit (20 K MWCO) (Slide-A-Lyzer, Thermo Scientific) for 48 h. DNA concentration was measured with Nanodrop 2000C spectrometer (Thermo Scientific). Particle size and zeta potential were measured by a Zetasizer (Nano ZS, Malvern).

For preparation of triglycerol monostearate (TGMS) nanoparticles, TGMS (Sigma) at a concentration of 0.5 mg/mL was sonicated in PB (pH 8.0) to make self-assembled TGMS NPs in water. For restriction enzyme (HhaI) loading, TGMS at a concentration of 0.5 mg/mL was sonicated in a solution of enzyme (1000 U) for 1 hour at 4° C. Excess enzyme was removed by centrifugation at 21 000 g for 5 min. HhaI was chosen as the restriction enzyme was due to their capacity to digest ssDNA.

For loading aPD-1 and Enzyme@TGMS NPs to DNA nano-cocoon, aPD-1 and Enzyme@TGMS NPs were mixed with DNA nano-cocoon at ratio of 0.2:1:1 (aPD-1: Enzyme@TGMS NPs: DNA nano-cocoon, wt:wt:wt). After ultrasonication treatment, the mixture was placed in the oscillation shaker in 4° C. overnight. Excess aPD-1 and TGMS NPs was removed by centrifugation (10 000 g) and washing with PBS several times.

Enzyme-Responsive Drug Release.

Release studies were performed at 37° C. with constant agitation in PBS+10% fetal ovine serum. PBS, MMP-9 (500 ng/mL, Sigma) or Lipase (10 000 U, Sigma) were added to samples to study the DNA and antibody release. The DNA disintegration was analyzed by agarose gel electrophoresis using 1% (w/v) agarose gel and the antibody release was determined by IgG total ELISA kit (eBioscience).

Mice and In Vivo Tumor Models.

Female C57B6 mice were purchased from Jackson Lab (USA) and were housed in the North Carolina State University Toxicology Building. All mouse studies were performed in the context of an animal protocol approved by the Institutional Animal Care and Use Committee at North Carolina State University. To measure effects on relapse, 10 d after $1\times10^6$ luciferase-tagged B16F10 tumor cells were transplanted into the back of mice (the tumor reaches ~100 mm$^3$), tumors were resected leaving little residual tissue behind. For the metastasis model, $1\times10^5$ B16F10 tumor cells were intravenously infused into C57BL/6 mice via tail vein one day before surgery. Mice were weighed and randomly divided into different groups. From Day 0, the mice were peritumourally injected with different drug formulations. The tumor growth was monitored by the bioluminescence signal of B16F10 cells. Images were taken on IVIS Lumina imaging system (Caliper, USA). Tumours were also measured by digital caliper. The tumour volume (mm$^3$) was calculated as (long diameter×short diameter$^2$)/2.

Analysis of MMP9 Production In Vivo.

After 1 hour of surgery, wound tissue was collected and cultured at 37° C. for 4 days. Each day 100 µL of medium was removed, frozen at −80° C. and 100 mL fresh medium added. Matrix metalloproteinase 9 (MMP9) concentration was determined by ELISA (ThermoFisher).

In Vivo Bioluminescence and Imaging.

Bioluminescence images were collected with a Xenogen IVIS Spectrum Imaging System. Living Image software (Xenogen) was used to acquire the data 10 min after intraperitoneal injection of d-luciferin (Pierce) in DPBS (15 mg/mL) into animals (10 µL/g of body weight).

Confocal Microscopy.

Tumors were dissected from the mice and snap frozen in optimal cutting medium (O.C.T.). Several micrometer sections were cut using a cryotome and mounted on slides. Sections were fixed in ice-cold acetone for 10 minutes prior to rehydration with PBS. After blocking with BSA (3%), sections were stained with primary antibodies overnight at 4° C. Slides were analyzed using a confocal microscope (Zeiss).

Cytotoxic T Lymphocyte Activity.

Splenocytes harvested from mice were restimulated with irradiated B16F10 cancer cells. Cells were washed three times with PBS and then cultured together with B16F10 target cells in 96-well culture plates at the effective target cell ratio of 500:1. After 24 h of incubation, the suspensions were collected to detect the LDH leakage level with a nonradioactive cytotoxicity assay (Thermo Scientific), which indicated the level of specific lysis of target cells by effective cells. The percentage of specific lysis was calculated according to % specific lysis=((experimental LDH release−effective cell LDH release)/(maximum LDH release−spontaneous LDH release))×100%.

Statistical Analysis.

Statistical analysis was evaluated using GraphPad Prism (5.0). Statistical significances were calculated with the paired Student t test and two-way ANOVA. Comparisons of survival curves were made using the log-rank test. P values of 0.05 or less were considered significant.

Results

Figure 1B:
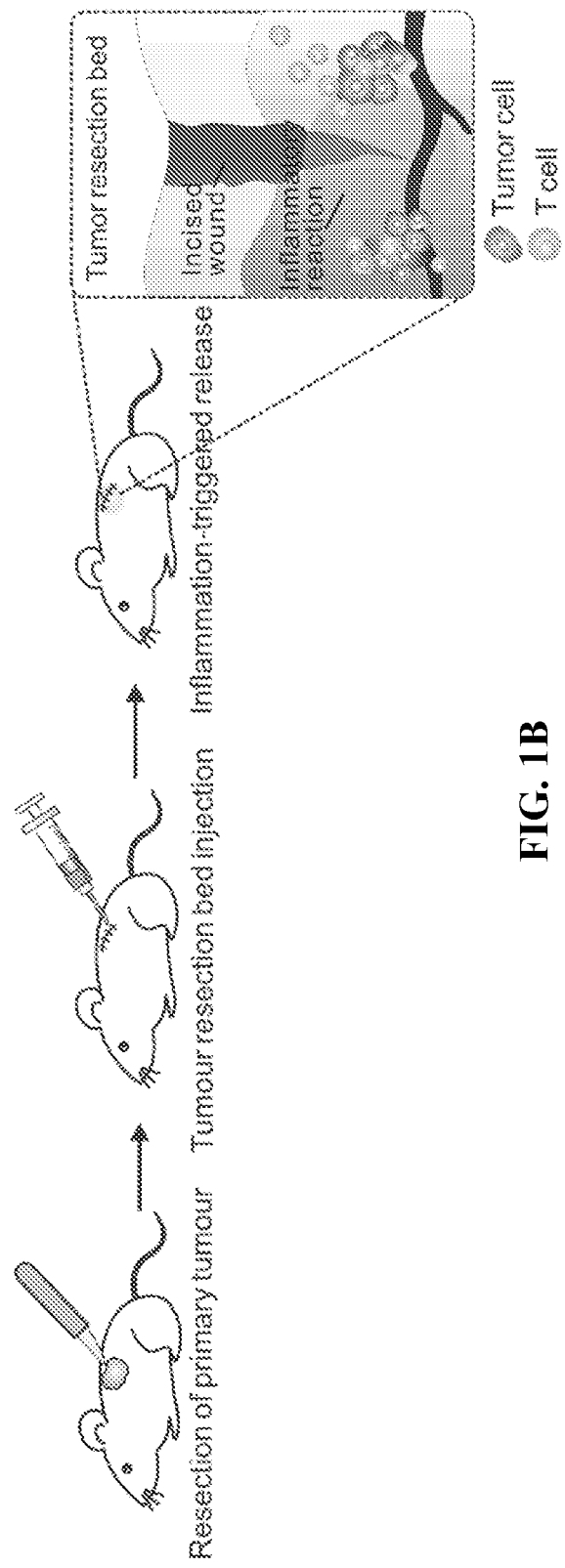

In this example, the inventors have developed a new cancer immunotherapy agent which can be used for the prevention of post-surgical tumor relapse. Tumor burden is the lowest after cancer surgery. Moreover, the local pro-inflammatory environment is conducive to immunotherapy. In this example, the inventors have developed an innovative delivery carrier for the controlled release of loaded anti-PD1 antibody (aPD1) and CpG oligodeoxynucleotides (ODNs) in response to inflammation conditions (FIG. 1A). CpG ODNs, trigger cells that express Toll-like receptor 9, including human plasmacytoid dendritic cells (pDCs), have potent immunostimulatory effects and can enhance the anti-cancer activity of a variety of cancer treatments (Marabelle, A. et al. *J. Clin. Invest.* 2013, 123, 2447; Krieg, A. M. *Oncogene* 2008, 27, 161). Through an enzymatic rolling circle amplification (RCA) method specifically based on a template encoded with the CpG sequence, the carrier (designated as DNA "nano-cocoons", DNCs) is assembled by a long-chain single-stranded DNA (ssDNA) (Jones, M. R. et al. *Science* 2015, 347, 1260901). The DNA contains repeating CpG sequences and cutting sites for the restriction enzyme HhaI, which are capable of digesting DNCs and subsequently generating CpG ODN fragments. To make the release event bio-responsive, HhaI is caged into triglycerol monostearate (TGMS) nanoparticles (TGMS NPs) and attached to DNCs. TGMS is an amphiphile whose ester linkage enables cleavage by esterases and matrix metalloproteinases (MMPs) that are highly expressed at the wound sites for developmental tissue remodeling (Gajanayake, T. et al. *Sci. Transl. Med.* 2014, 6, 249ra110). Triggered by the inflammatory condition occurring in the wound site of the tumor resection incision (FIG. 1B), TGMS can be enzymatically cleaved (Gajanayake, T. et al. *Sci. Transl. Med.* 2014, 6, 249ra110; Karp, J. M. et al. Google Patents: 2011), thereby disassembling the cage and releasing the HhaI, which can further sequentially convert DNCs to CpG ODNs and release aPD1 as well. The combination action of released CpG ODNs and aPD1 (FIG. 1C) can facilitate induction of durable and specific anti-tumor T-cell responses in a melanoma model, avoiding the toxic peak level in the body (Hamid, O. et al. *N. Engl. J. Med.* 2013, 369, 134).

Synthesis and Characterization of Triglycerol Monostearate Nanoparticles and DNA Nano-Cocoon (TGMS-DNC) Complexes.

Figure 5A:
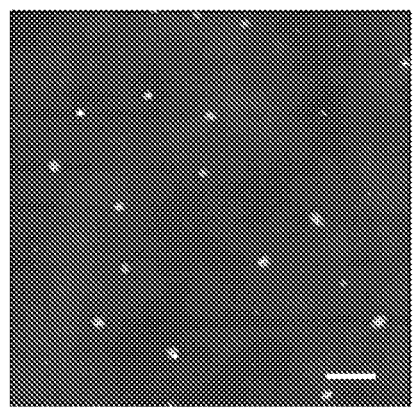
FIGS. 5A-5C. Images and size analysis of DNA nano-cocoons (DNCs).
Figure 5B:
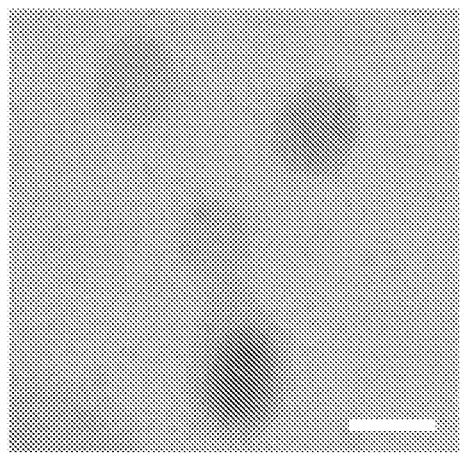
Figure 5C:
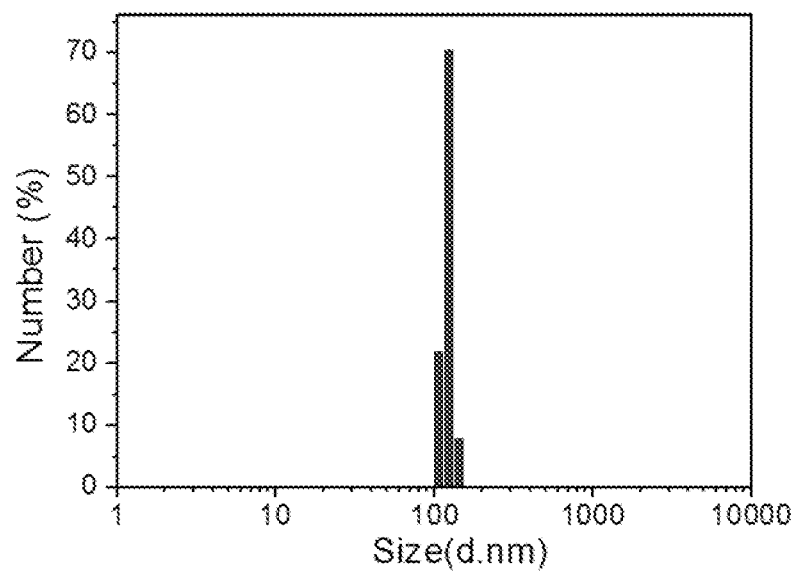
Figure 6A:
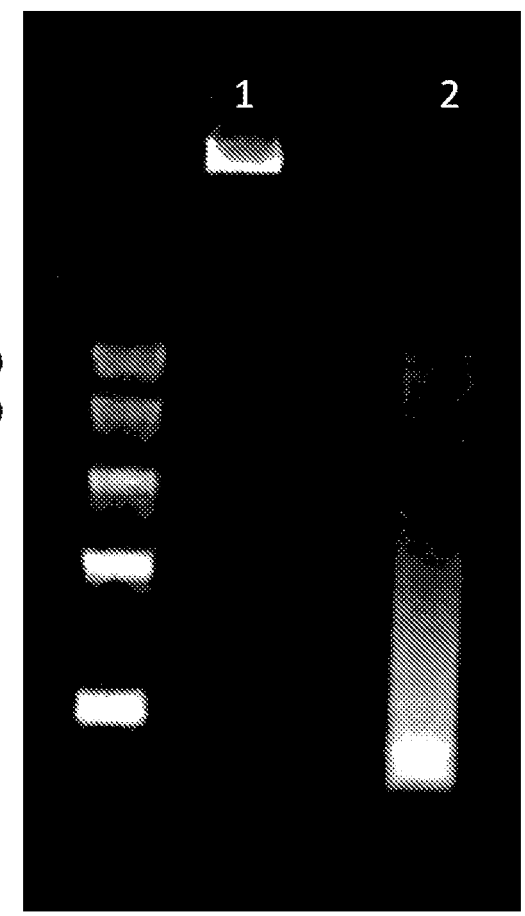
FIGS. 6A-6B. DNA nano-cocoon (DNC) degradation by the restriction enzyme HhaI.
Figure 6B:
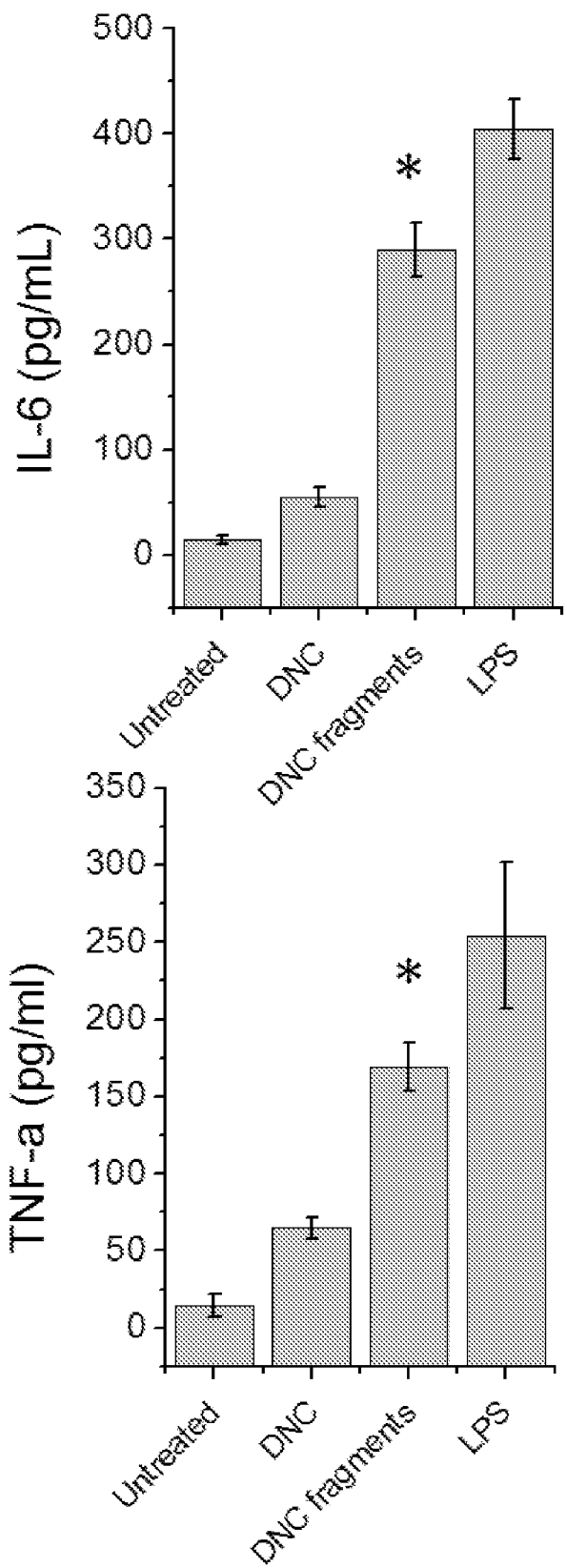

As shown in FIG. 5, the synthesized ssDNA self-assembled into the three-dimensional "cocoon"-like structure with an average particle size of 150 nm, as revealed by the transmission electron microscopy (TEM) and atomic force microscopy (AFM). The obtained DNCs can be digested into small homogeneous fragments treated with HhaI (FIG. 6). More importantly, these homogeneous fragments can induce TNF-α and IL6 production in RAW264.7 cells (FIG. 6), indicating that the DNCs can be degraded into CpG ODNs after restriction enzyme treatment. Two different control DNCs (cDNC) with a non-specific sequence were synthesized (Table 1) to verify the design.

sites, without CpG) could be readily cut into smaller homogeneous fragments, while the other cDNCs (with CpG, without cutting sites) were resistant to cleavage by HhaI.

Figure 2A:
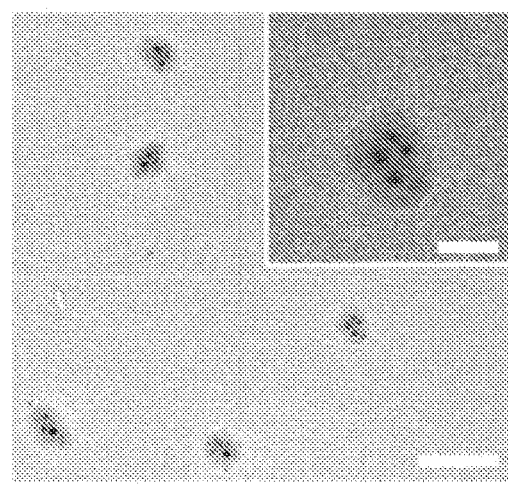
FIGS. 2A-2J. Characterization of CpG DNA nano-cocoons (DNCs) loaded with aPD1 and caged enzyme and enzyme-responsive drug release.
Figure 2B:
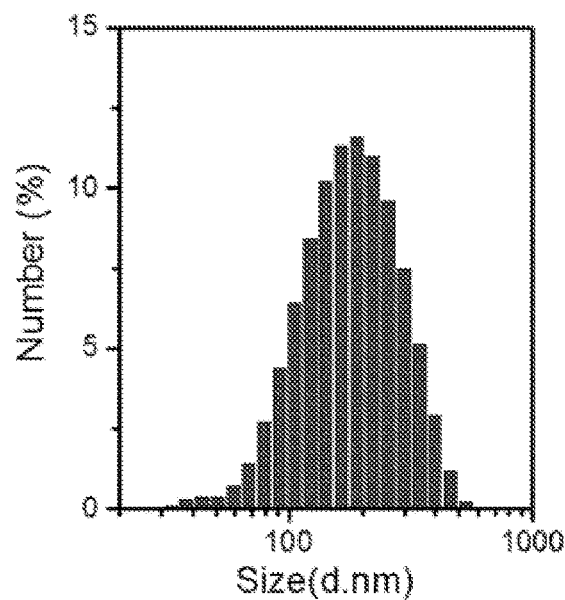
Figure 8A:
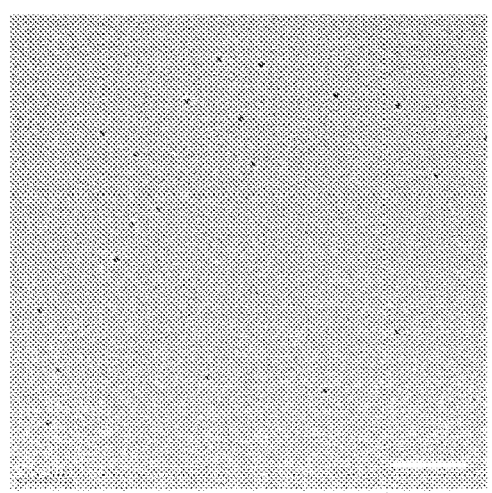
FIGS. 8A-8B. Images and size analysis of triglycerol monostearate (TGMS_nanoparticles (FIG. 8A) TEM and (FIG. 8B) DLS of TGMS nanoparticles. (Scale bar=500 nm)
Figure 8B:
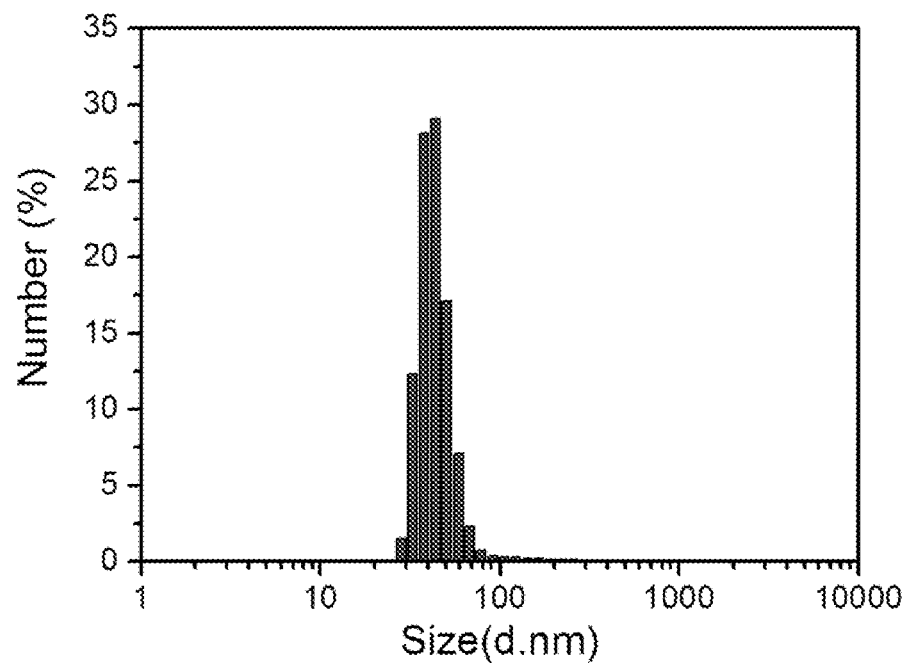
Figure 9:
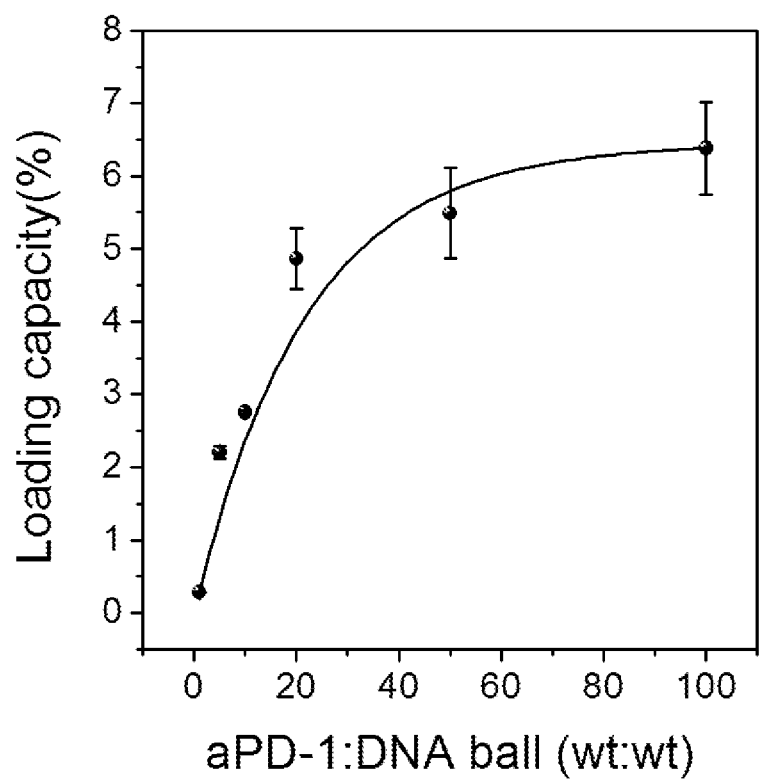
FIG. 9. Loading capacity of aPD-1 at different aPD-1 concentrations.

The enzyme could be caged into triglycerol monostearate nanoparticles (TGMS NPs) with a diameter about 30 nm monodispersed in PBS (FIG. 8). The enzyme activity of HhaI was significantly inhibited when caged into TGMS NPs (FIG. 10). It was also demonstrated that TGMS NPs can efficiently attach to DNA nano-cocoon to form monodispersed TGMS-DNC NPs after mixing, as revealed by TEM and dynamic light scattering (DLS) (FIG. 2A-B). Once attached with TGMS NPs, DNA nano-cocoon displayed an increase in the DLS measured diameter, from 150 nm to 210 nm. In addition, it is found that the aPD1 could be further loaded into TGMS-DNC NPs after ultrasonication and incubation overnight at 4° C. The loading efficiency of aPD1 was about 6.0%, as determined by the ELISA assay (FIG. 9).

In Vitro Inflammatory-Responsive CpG and aPD1 Release from TGMS-DNCs Complexes.

Figure 12A:
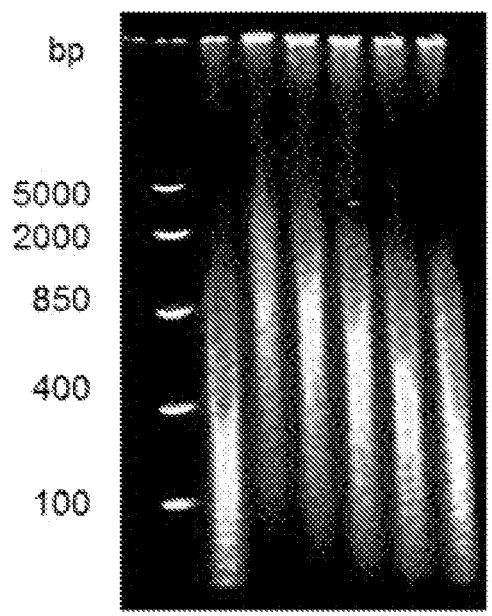
FIGS. 12A-12C.
Figure 12B:
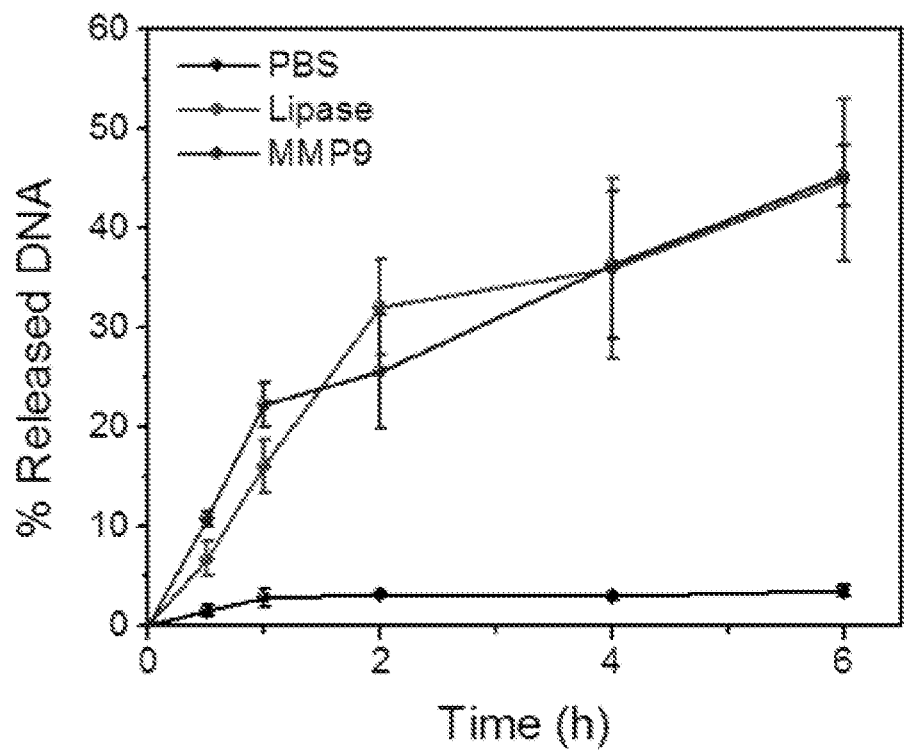
Figure 12C:
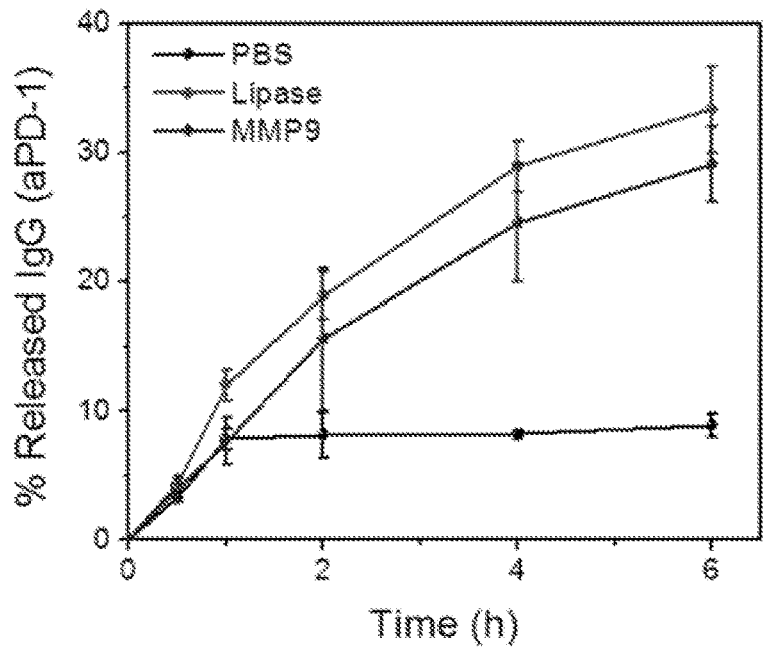

The controlled release profiles in response to inflammation conditions in vitro was analyzed next. Proteolytic enzymes, such as MMPs, are significantly up-regulated under inflammatory conditions like perioperative trauma (Ryan, T. J. *Australas. J. Dermatol.* 1994, 35, 35; Armstrong, D. G.; Jude, E. B. *J. Am. Podiatr. Med. Assoc.* 2002, 92, 12). It was determined that TGMS NPs were quickly dissociated by MMP9 treatment, as visualized by TEM imaging (FIG. 11). Next, the ability of TGMS-DNCs to disassemble and release the loaded aPD1 in response to the proteolytic enzymes was evaluated. TGMS-DNCs were incubated at 37° C. with lipase (esterase) or MMP-9 enzyme (500 ng/mL) in PBS. The degradation of DNA nano-cocoon and release profile of aPD1 were quantified by the agarose gel electrophoresis and ELISA assay, respectively (FIG. 12). The data show that DNA nano-cocoons were degraded into small DNA fragments upon the MMP-9 treatment as time increased. The cumulative release profiles of DNA and aPD1 revealed that lipase and MMPs could trigger fragmentation of DNCs and subsequently release the loaded aPD1. Whereas TGMS-DNCs in the PBS control solution remained stable and release insignificant amount of the

TABLE 1

Sequences of DNA oligos.

Template

| | |
|---|---|
| T-CpG DNC:<br>SEQ ID NO. 1<br>(underlined portion only) | 5'PO$_4$GCGCGTCGTCGTTCGAACGACGTTGCGCGTCGTCGT<br>TCGAACGACGTTGCGCGTCGTCGTTCGAACGACGTT3' |
| T-CpG cDNC-1:<br>SEQ ID NO. 2<br>(underlined portion only) | 5'PO$_4$ATATGTCGTCGTTCGAACGACGTTATATAACGTCGT<br>TCGAACGACGTTATATGTCGTCGTTCGAACGACGTT3' |
| T-CpG cDNC-2:<br>SEQ ID NO. 3<br>(underlined portion only) | 5'PO$_4$GCGCGTATTATTTCGAAATAATTTGCGCGTATTATT<br>TATAAATAATTTGCGCGTATTATTTATAAATAATTT3' |

Portions of sequences that are double underlined (GCGC in SEQ ID NO:1 and SEQ ID NO: 3) indicate the cutting sites of restriction enzyme HhaI.

Shaded parts indicate CpG sequence.

Figure 7:
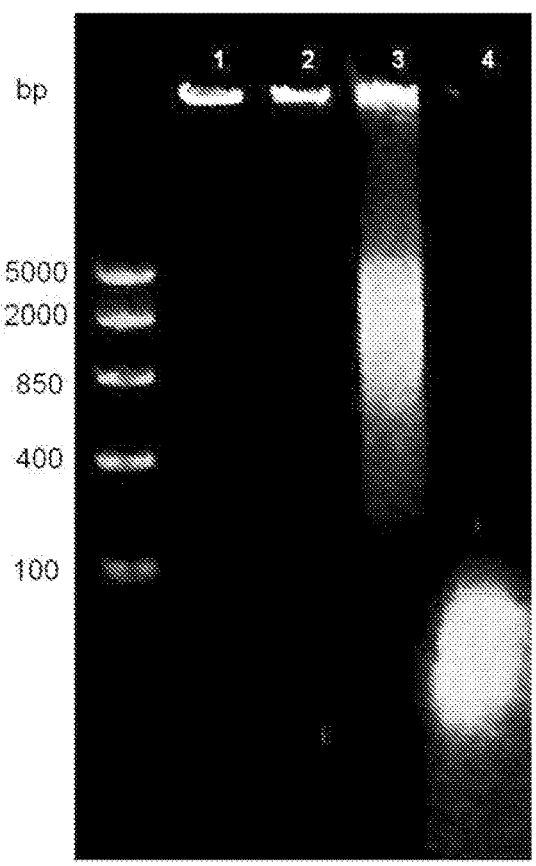
FIG. 7. Gel electrophoresis of two control DNCs after being treated with HhaI. While being treated with HhaI, one cDNC (cutting sites+CpG−) could can be readily cut into smaller homogeneous fragments, while the other cDNCs (cutting sites−CpG+) were resistant to cleavage by HhaI.
Figure 13A:
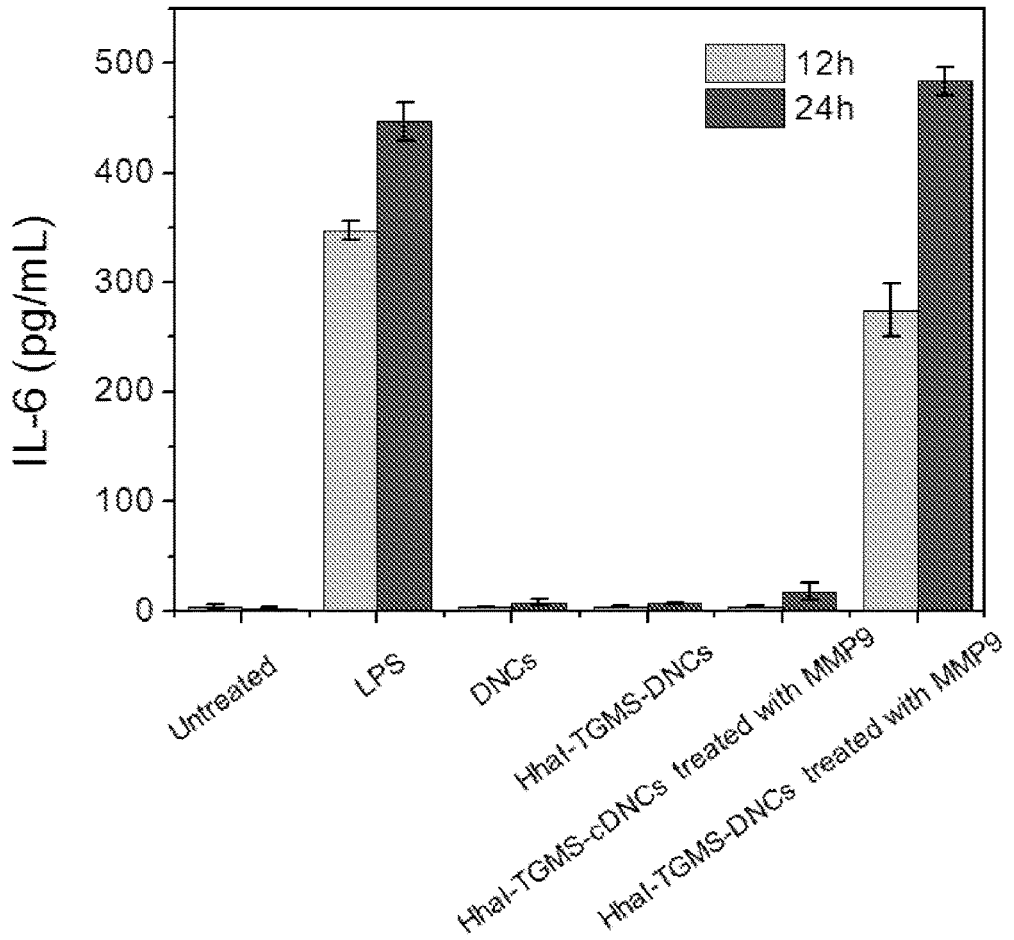
FIGS. 13A-13B. Secretion of (FIG. 13A) IL-6 and (FIG. 13B) TNF-α by RAW 264.7 macrophages as determined by ELISA.
Figure 13B:
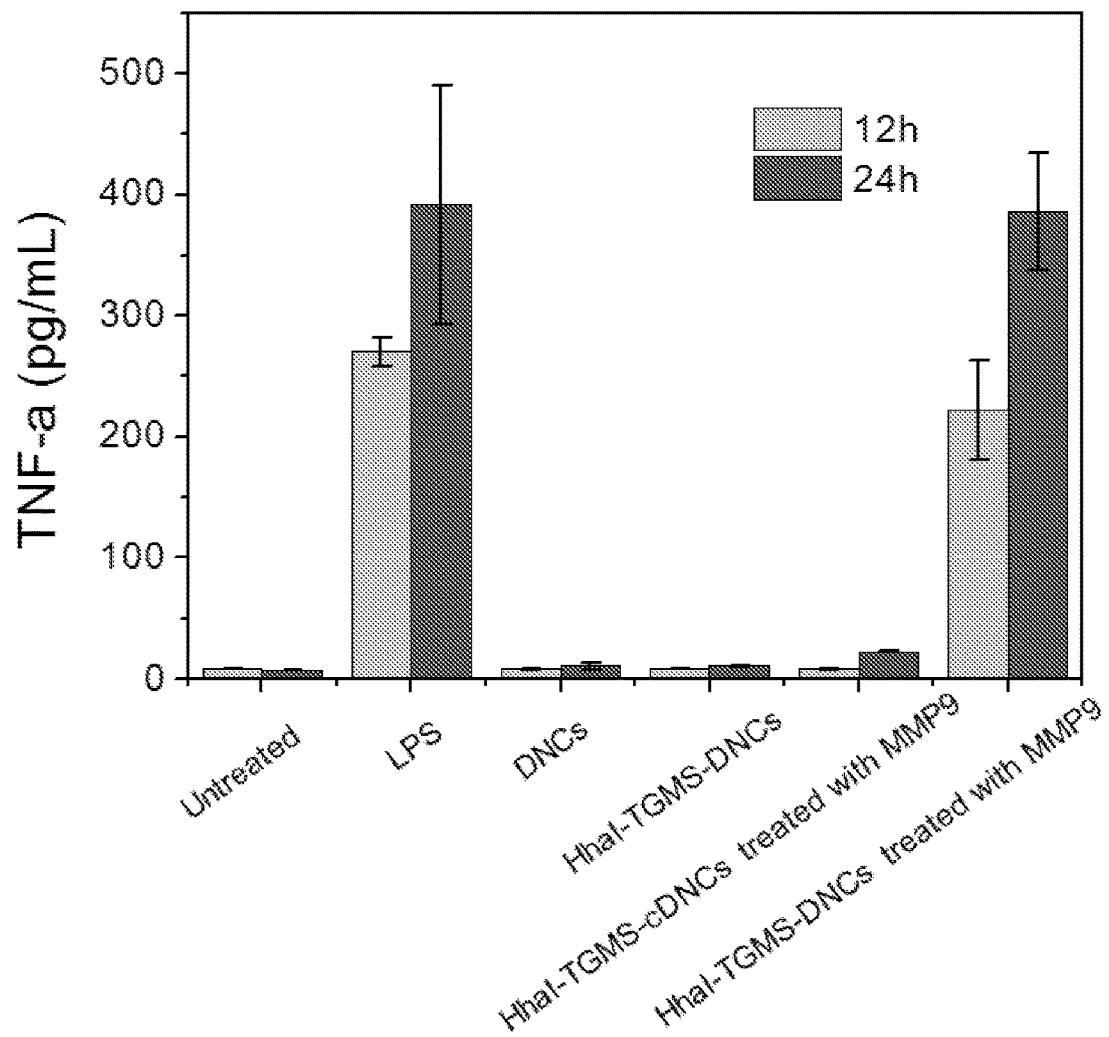

As shown in agarose gels (FIG. 7), without HhaI treatment, these cDNCs cannot migrate in the gel as DNCs. While being treated with HhaI, one cDNC (with cutting aPD1 over time (FIG. 12). Furthermore, the DNCs after MMP-9 treatment can effectively induce IL-6 and TNF-α production in murine macrophage (RAW264.7) cells, indicating that DNCs were digested into CpG nucleotides (FIG. 13).

Figure 2C:
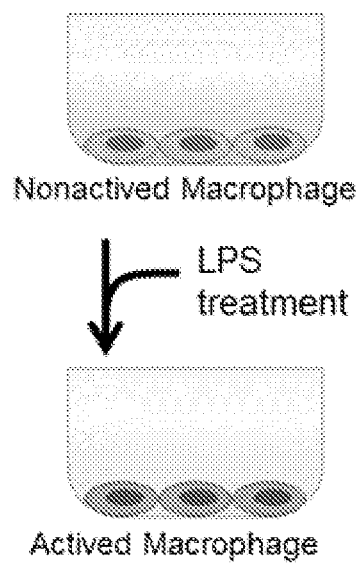
Figure 2D:
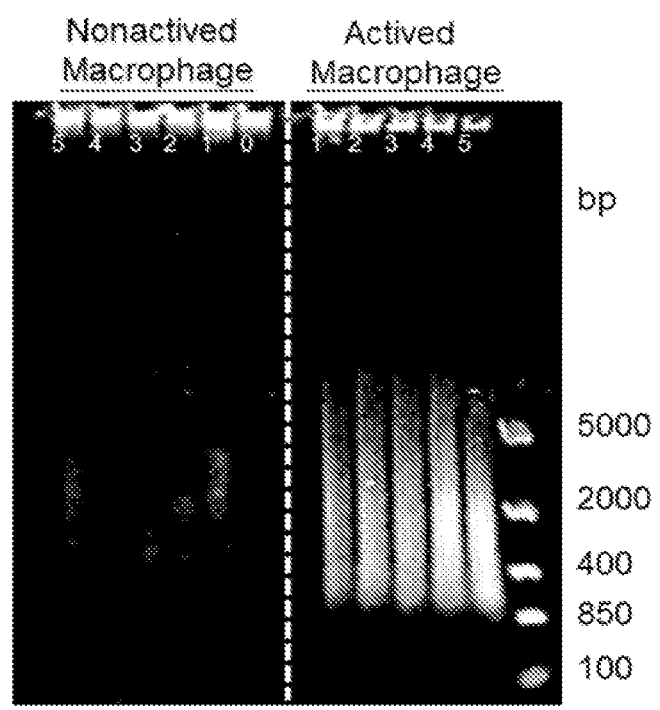
Figure 2E:
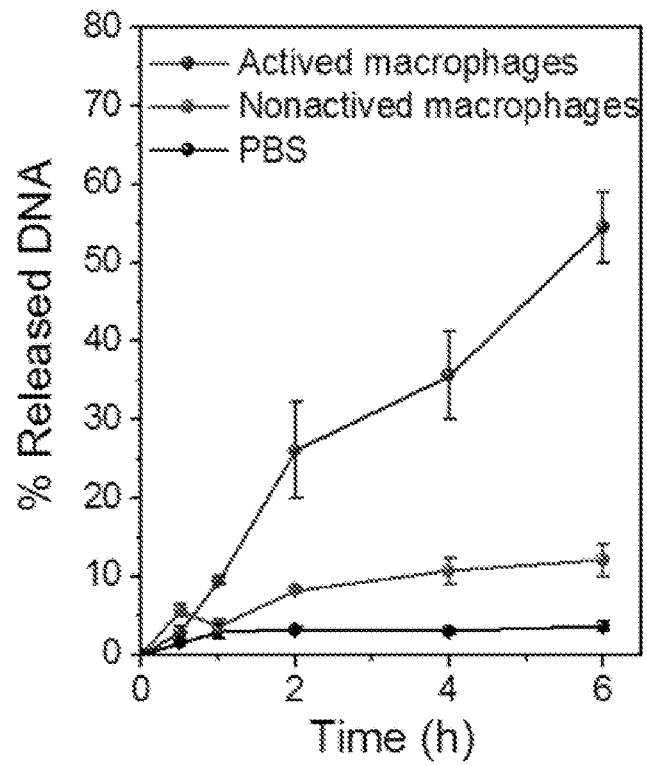
Figure 2F:
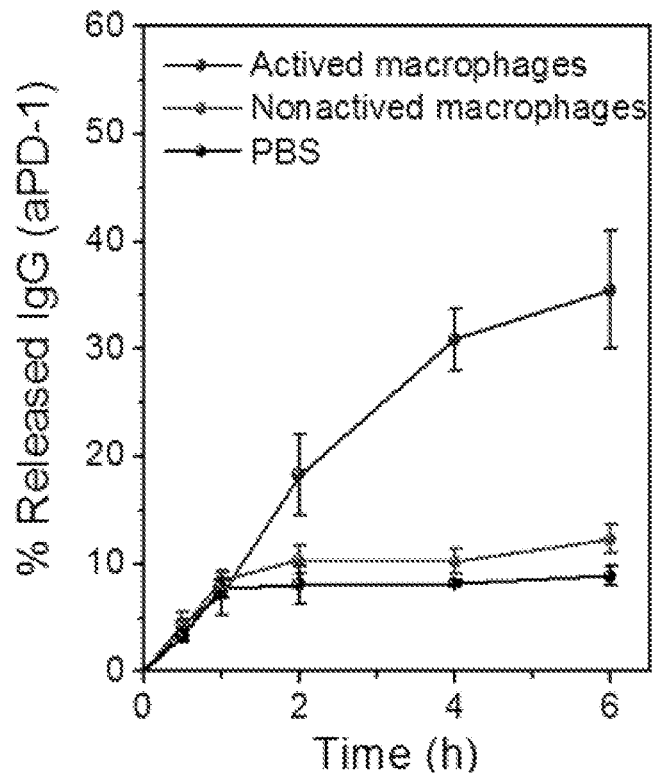

To further mimic the conditions of inflammation in vitro, RAW 264.7 cells were activated by treatment with lipopolysaccharide (LPS) (FIG. 2C). After 24 hours, the cell culture medium from the activated macrophages was added to TGMS-DNCs and incubated at 37° C. The release of CpG nucleotides and aPD1 were quantified in medium at different time points (FIG. 2D-F). Plotting cumulative release versus time revealed that the medium from the LPS activated macrophages triggered TGMS-DNCs degradation, leading to the sustained release of the aPD1. Whereas the medium of the nonactivated macrophage cultures did not. Furthermore, the atomic force microscopy (AFM) image and DLS data indicated that the TGMS-DNCs complexes remained stable when treated with the nonactivated macrophage cultures; while a high degradation efficiency of TGMS-DNCs complexes was observed when treated with the medium from the LPS activated macrophages (FIG. 2G-J).

In Vivo Anti-Tumor Relapse of TGMS-DNCs Complexes Post-Operative.

Figure 3A:
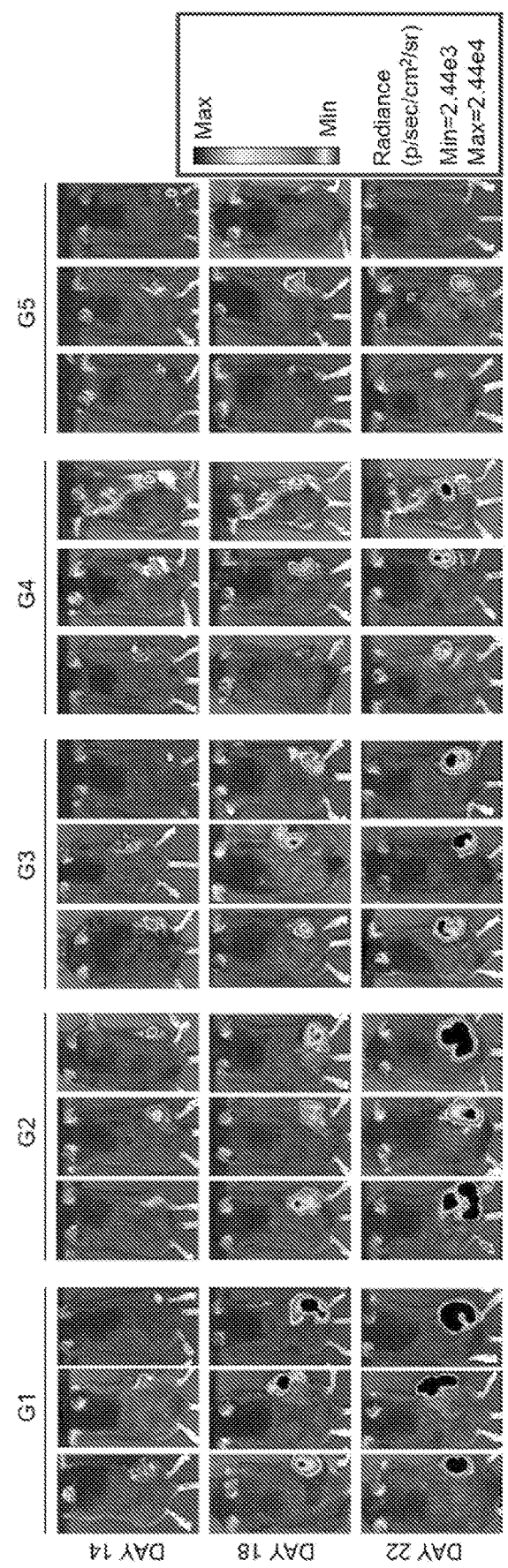
FIGS. 3A-3H. In vivo tumor therapy to reduce post-surgical tumor relapse via CpG DNA nano-cocoons (DNC) delivery system.
Figure 3B:
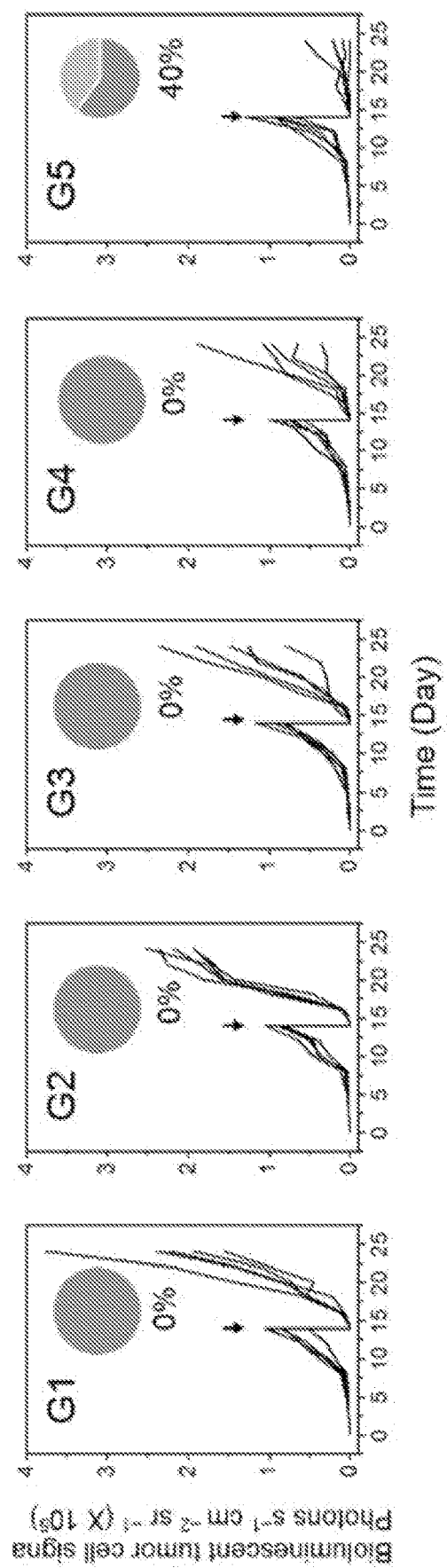
Figure 3C:
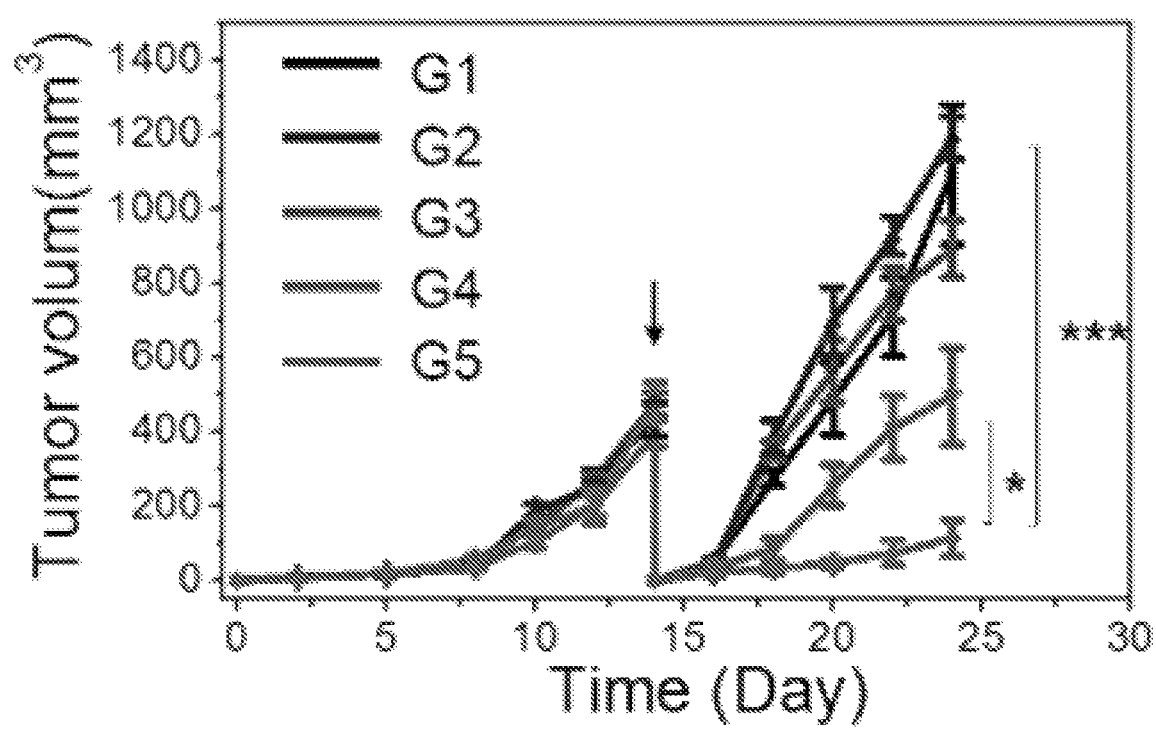
Figure 14:
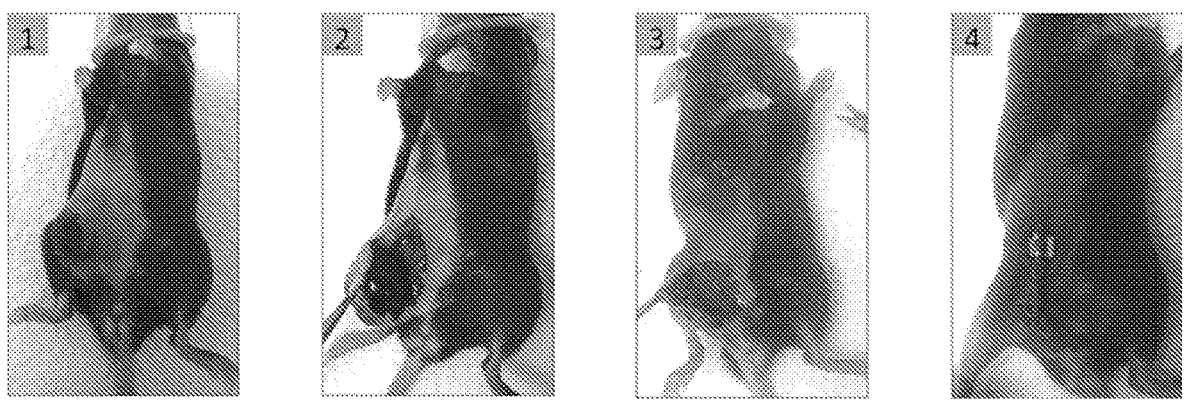
FIG. 14. Implementation of the approach. 1, primary tumor; 2, remove the tumor through surgery; 3, tumors were resected leaving ~1% residual tissue behind (incomplete resection); 4, peritumoural injection of the DNCs drug delivery system.
Figure 15:
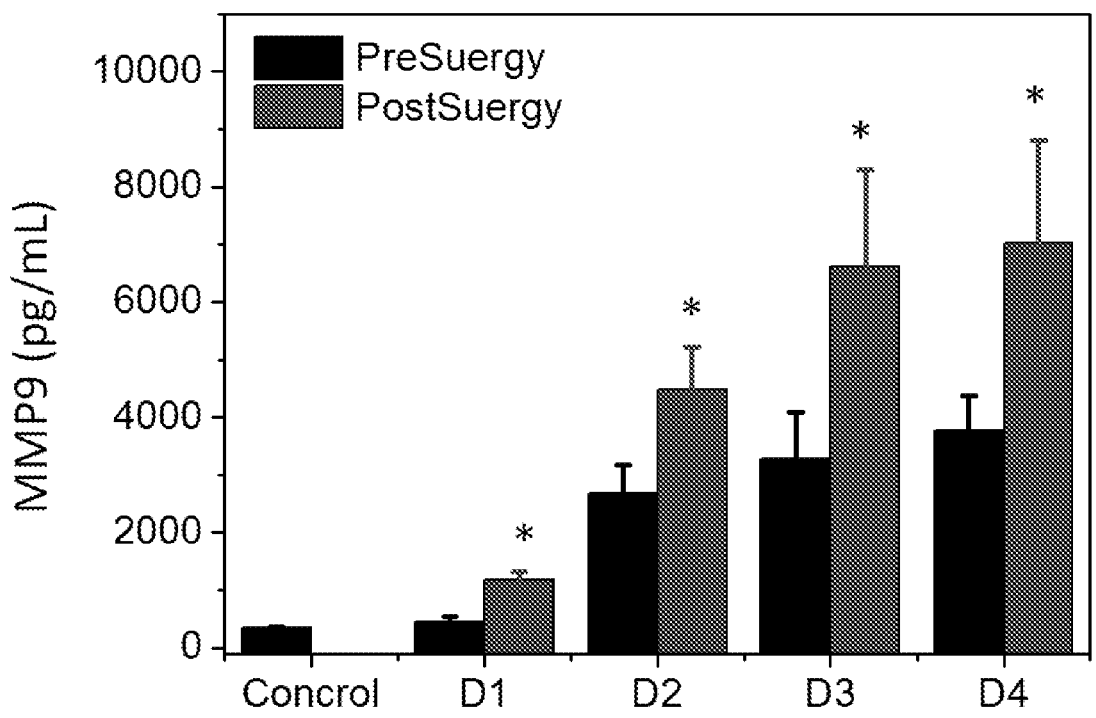
FIG. 15. Supernatants from wound tissues at days 1-4 post wounding were tested for MMP9 activity by ELISA.
Figure 16:
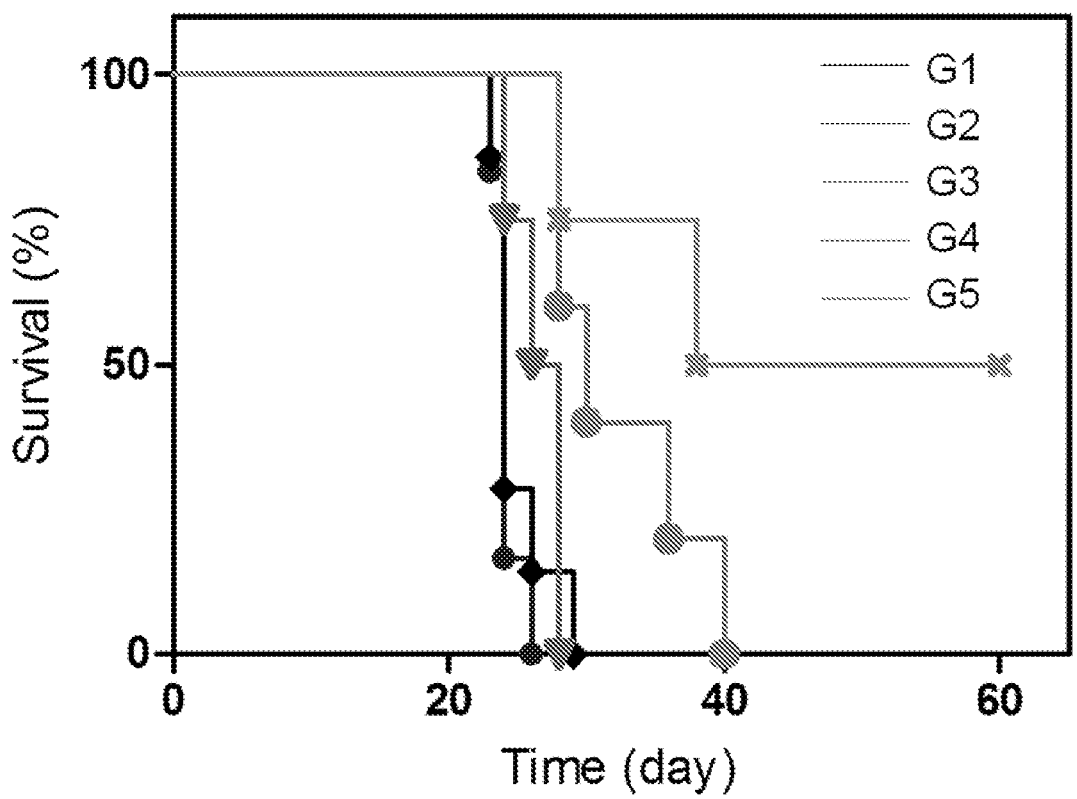
FIG. 16. The survival curves of mice in 60 days after various treatments indicated (G1, PBS control; G2, HhaI-TGMS-DNCs; G3, HhaI-TGMS-cDNCs-aPD1; G4, free aPD1/free CpG nucleotides; G5, HhaI-TGMS-DNCs-aPD1).

To evaluate anti-tumor relapse of the TGMS-DNCs complexes post-operative, the B16F10 mouse melanoma incomplete tumor resection model was used (which mimics local and systemic recurrences arising post-surgically) (FIG. 14) (Stephan, S. B. et al. Nat. Biotechnol. 2015, 33, 97). To verify the up-regulated expression of MMP-9 in the operative site, medium from wound tissues at day 1-4 post operation were tested for MMP-9 activity by ELISA (FIG. 15). Significantly increased levels of active MMP-9 were observed in the wounds cultured ex vivo, compared to the presurgery and unwounded tissue, thereby indicating that surgery promotes the MMP-9 secretion in the wound site. After incomplete operation to removal of the tumor, the mice were peritumorally injected with single dose of varying drug formulations, including PBS control (Group 1 (G1)), HhaI-TGMS-DNCs (G2), HhaI-TGMS-cDNCs (including cutting sites of HhaI without CpG sequence)-aPD1 (G3), free aPD1/free CpG nucleotides (G4) and HhaI-TGMS-DNCs-aPD1 (G5) (aPD1, 0.5 mg/kg. DNA, 10 mg/kg). Tumor growth was monitored by the bioluminescence signals of B16F10 cells and the sizes of the tumor (FIG. 3A-C). Mice receiving HhaI-TGMS-DNCs-aPD1 treatment showed the smallest relapsed tumor volumes. Of note, 40% of mice showed complete responses to the combination therapy. The remaining mice showed substantially delayed tumor growth (FIG. 3B). In other tested groups, free aPD1 and free CpG nucleotides co-administered mice showed a modest delay of tumor growth but did not prevent relapse. Furthermore, the prevention of tumor relapse in mice treated with HhaI-TGMS-DNCs and HhaI-TGMS-cDNCs-aPD1 was not more successful than the controls. It was also observed that these antibodies alone, without CpG DNCs, had insignificant efficacy toward tumor regression, indicating that CpG was critical to enhance the anti-tumor immune response together with aPD1 treatment. In addition to the prevention of tumor relapse, tumor size in mice was correlated with their survival (FIG. 16). Complete tumor regression and survival (40%) was observed 60 days after combination therapy. Co-administered free aPD1 and free CpG nucleotides modestly increased average survival times. Also neither HhaI-TGMS-DNCs nor HhaI-TGMS-cDNCs-aPD1 treatment improved survival over PBS controls.

Figure 3D:
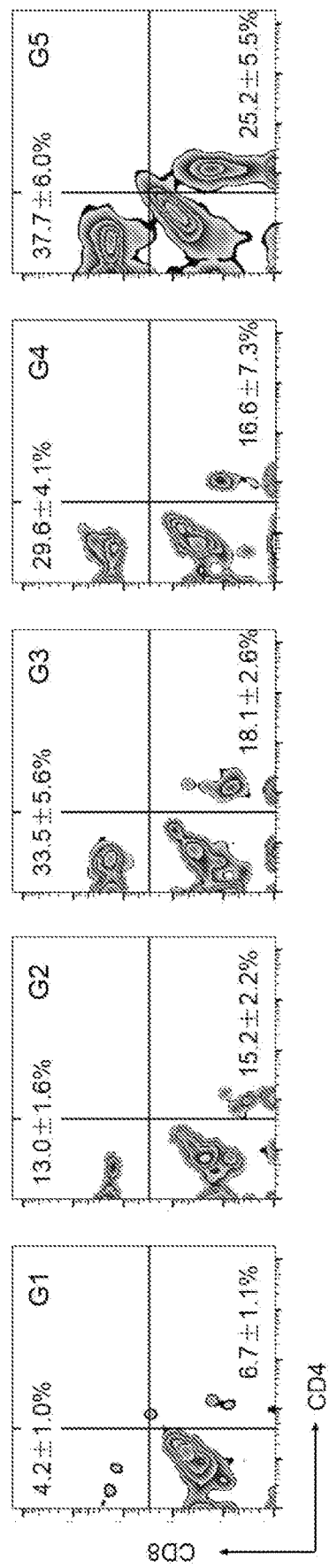
Figure 3E:
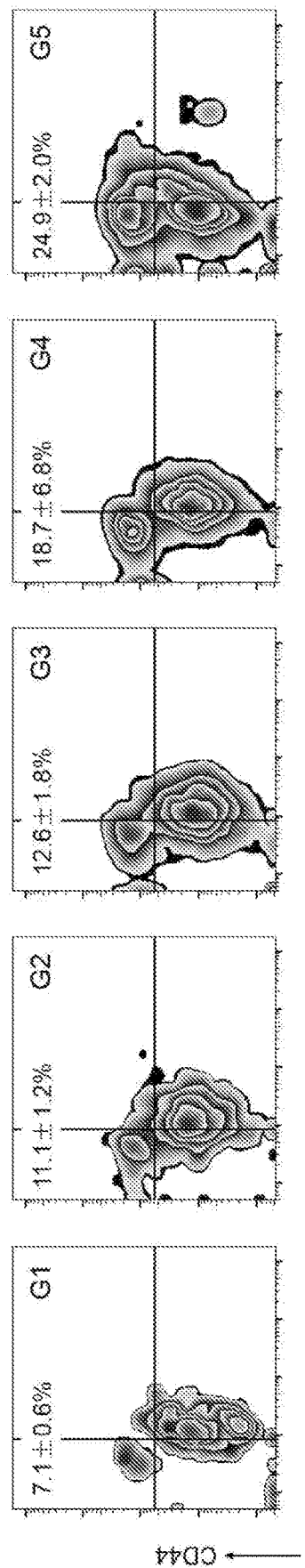
Figure 3F:
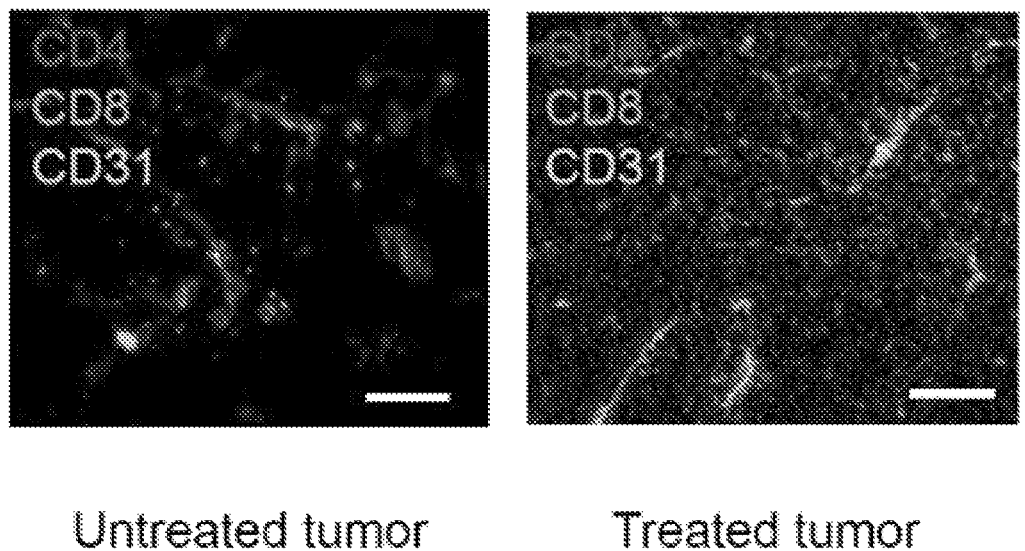
Figure 3G:
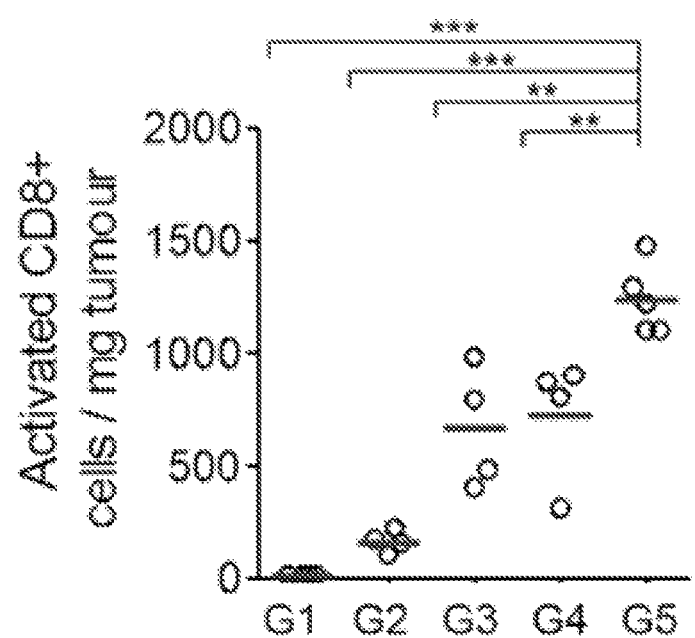
Figure 3H:
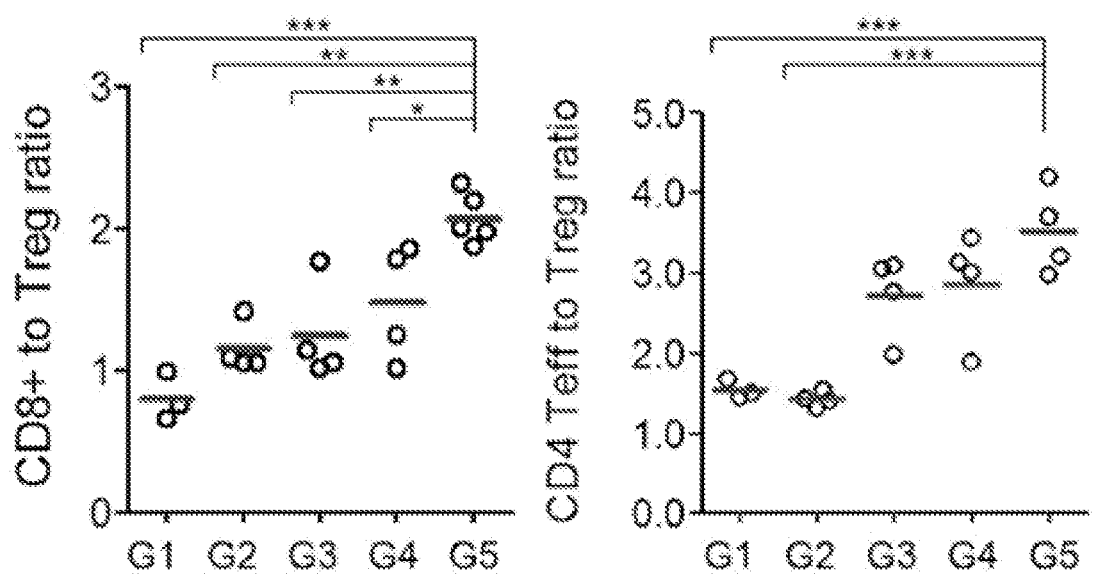
Figure 17:
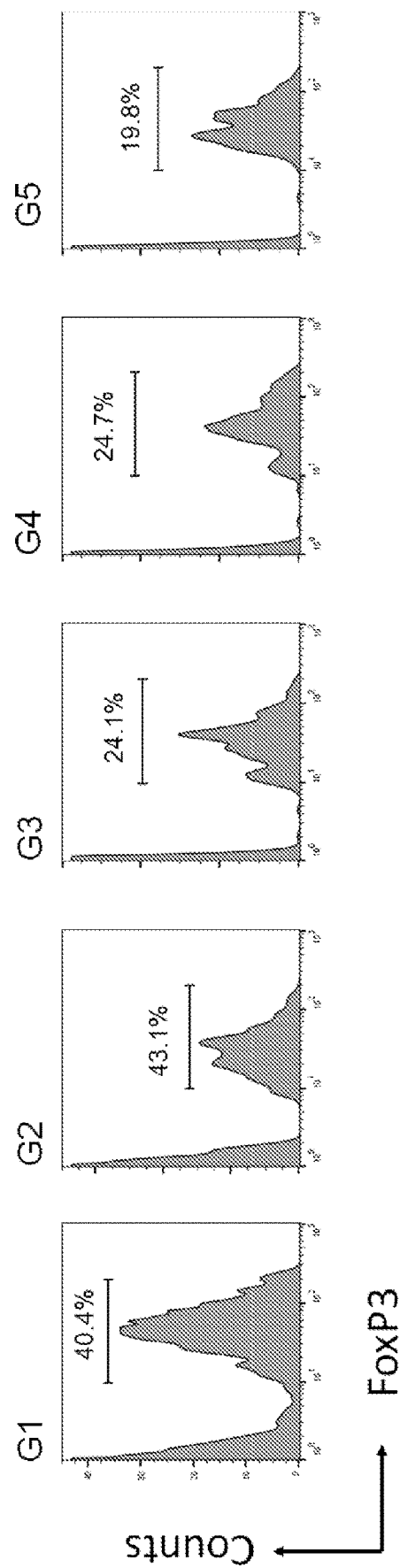
FIG. 17. Representative flow cytometry plots showing percentage (gated on CD4+ cells) of CD4+FoxP3+ T cells in relapsed tumors after various treatments indicated.
Figure 18A:
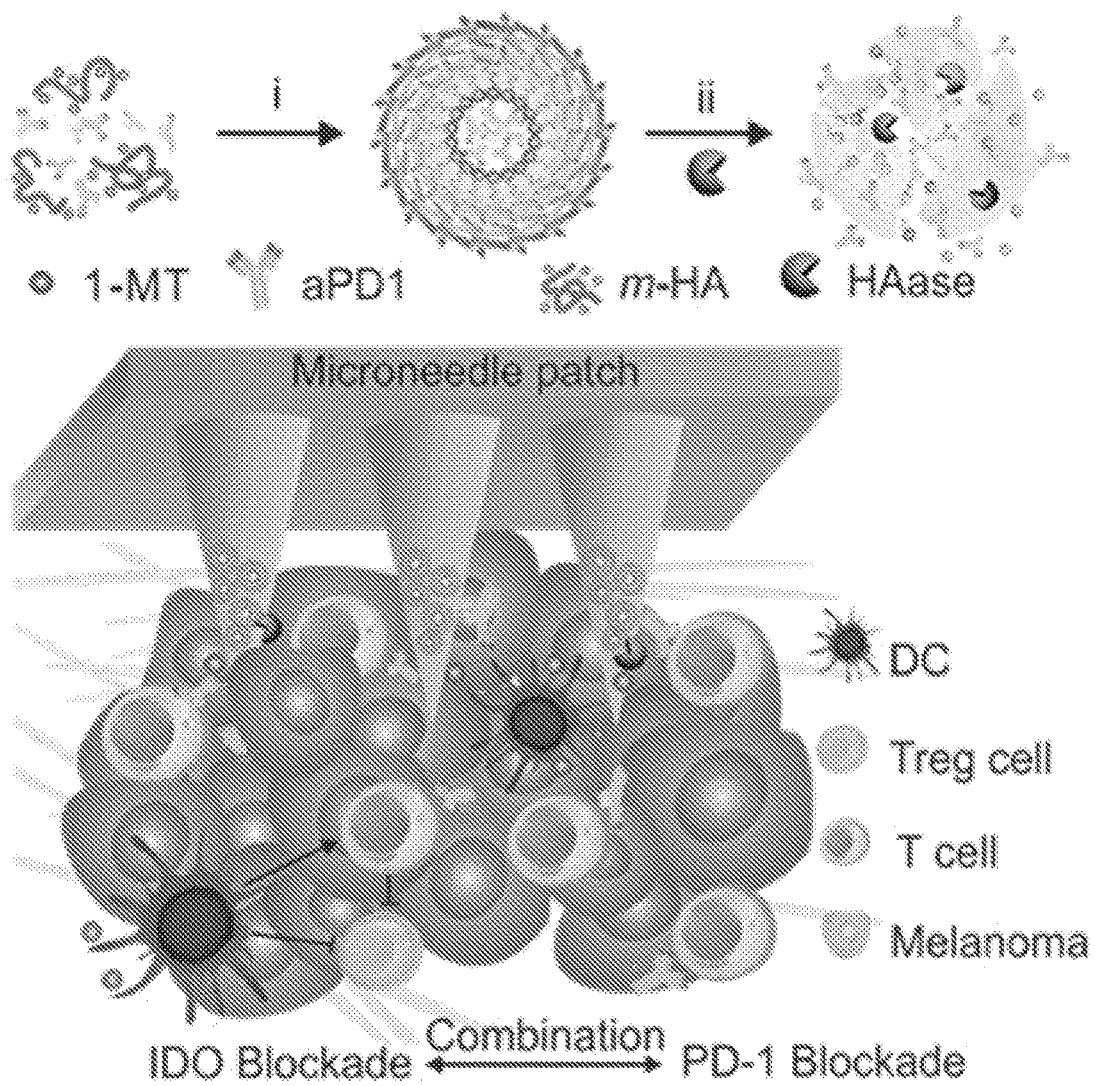
FIGS. 18A-18E. The schematics of a microneedle-based transcutaneous platform loaded with self-assembled immunotherapeutic nanocarriers.
Figure 18B:
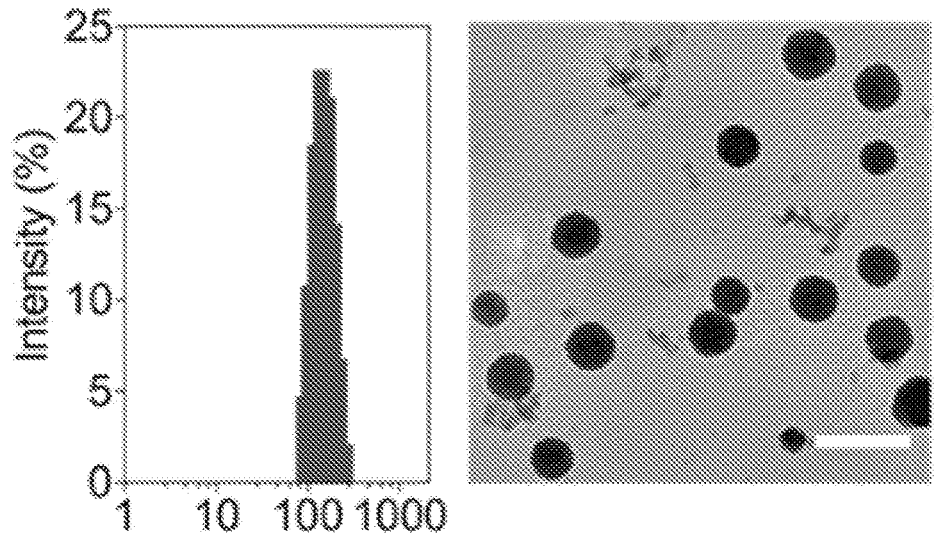
Figure 18C:
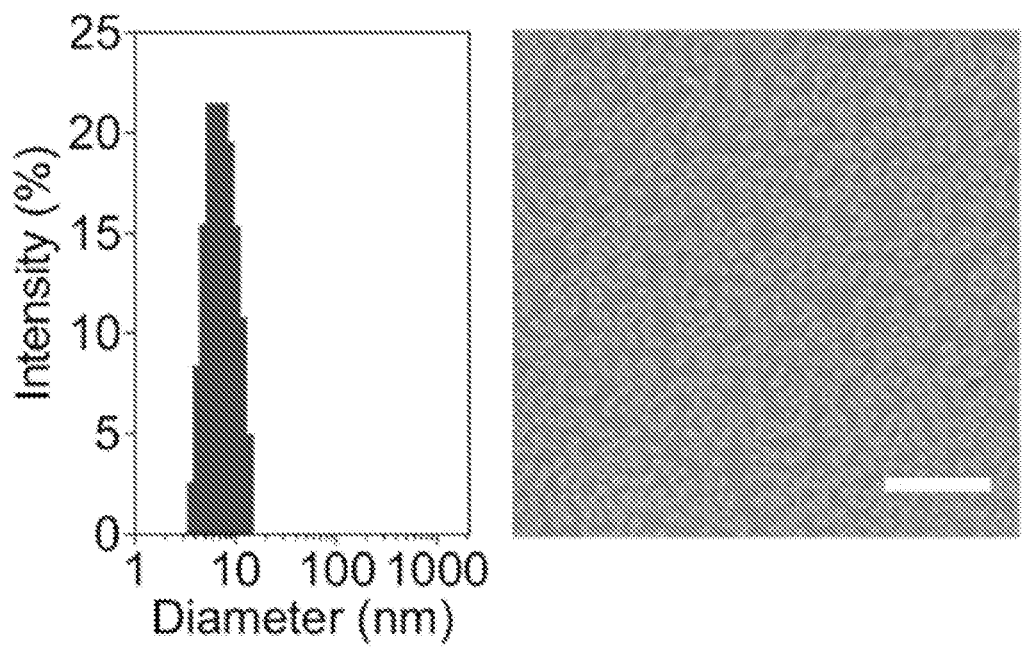
Figure 18D:
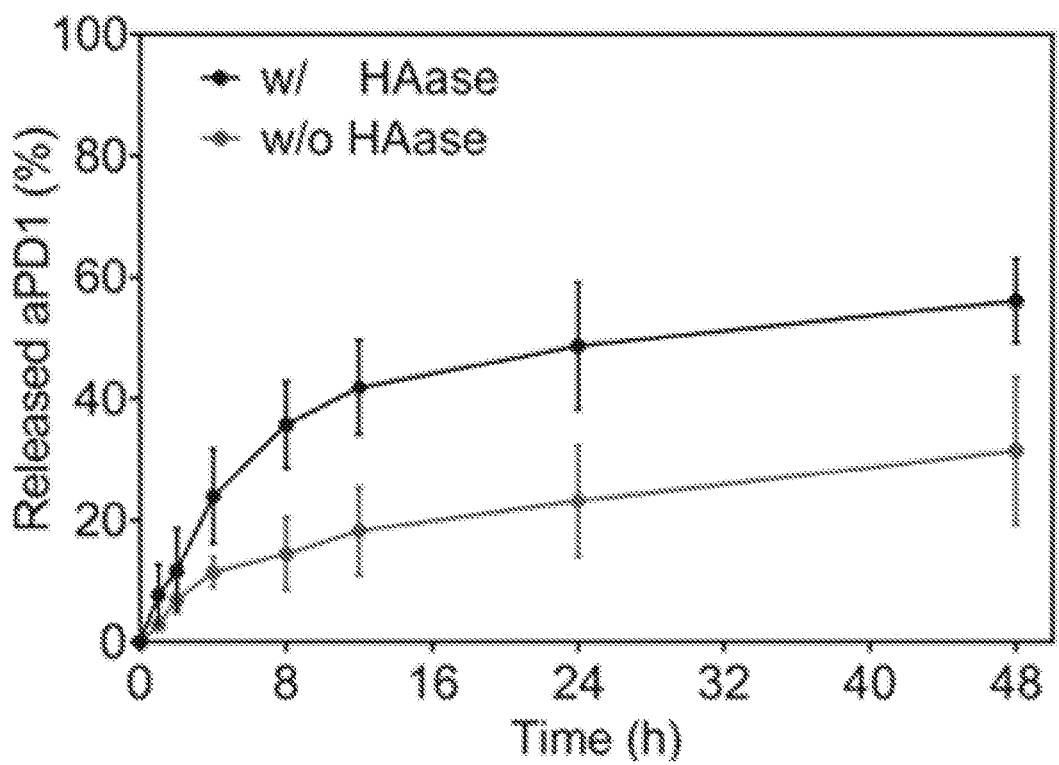
Figure 18E:
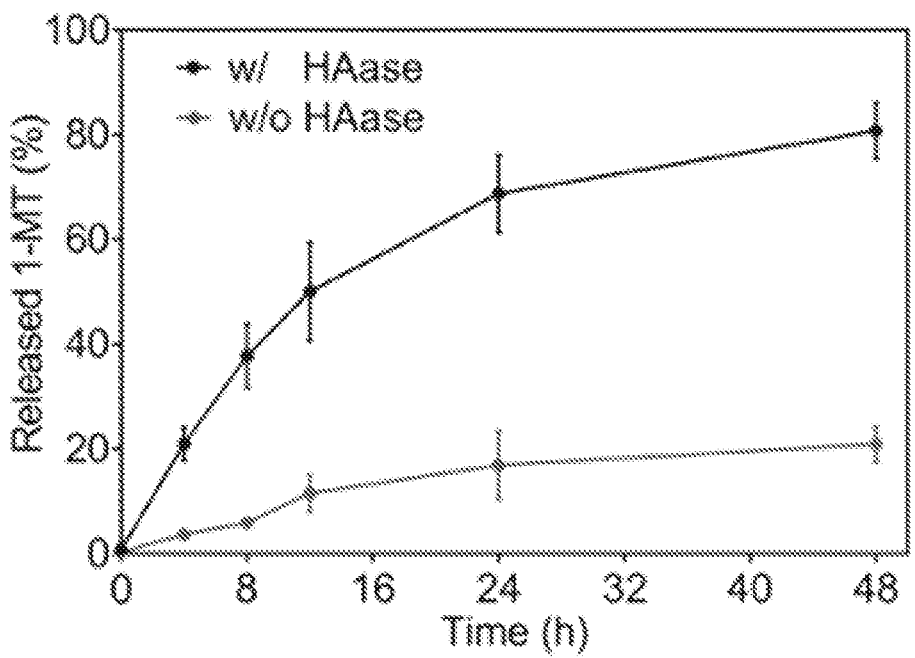
Figure 19A:
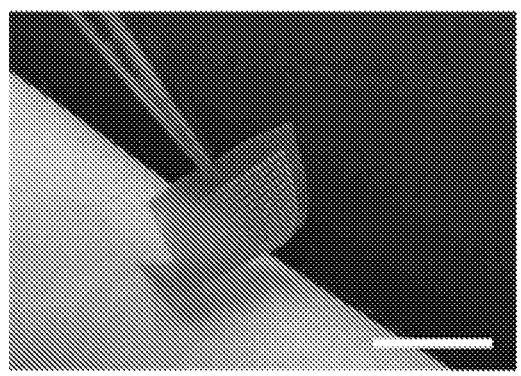
FIGS. 19A-19I. Characterization of aPD1/1-MT loaded microneedles.
Figure 19B:
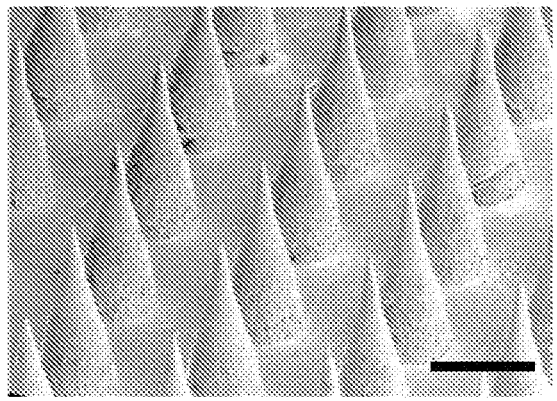
Figure 19C:
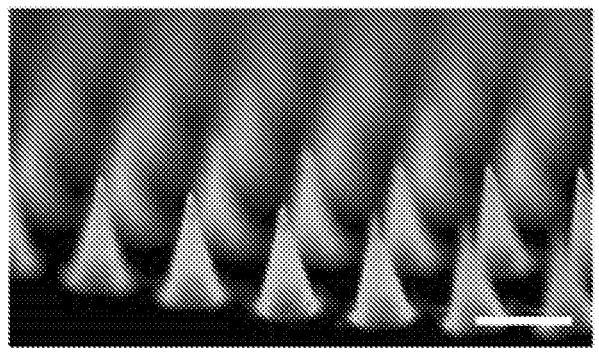
Figure 19D:
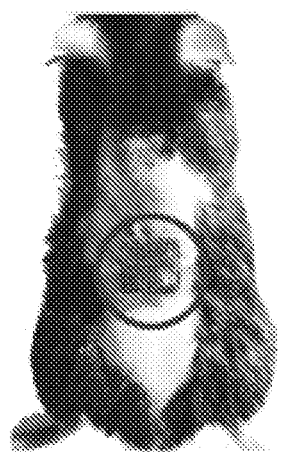
Figure 19E:
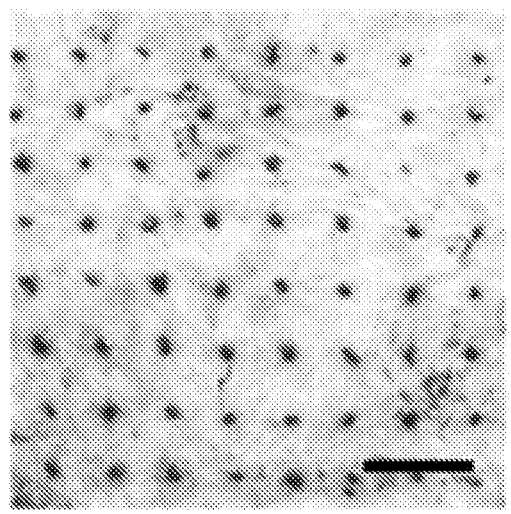
Figure 19F:
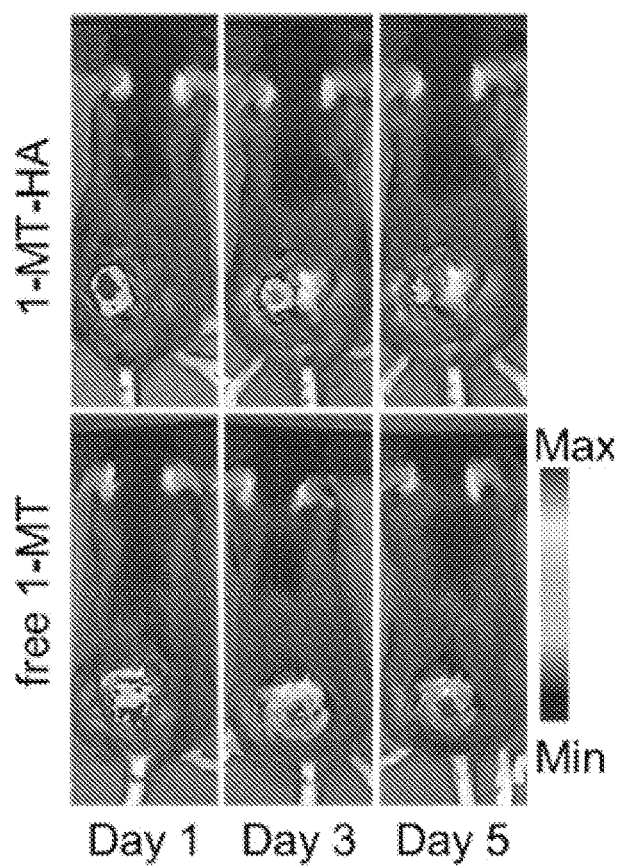
Figure 19G:
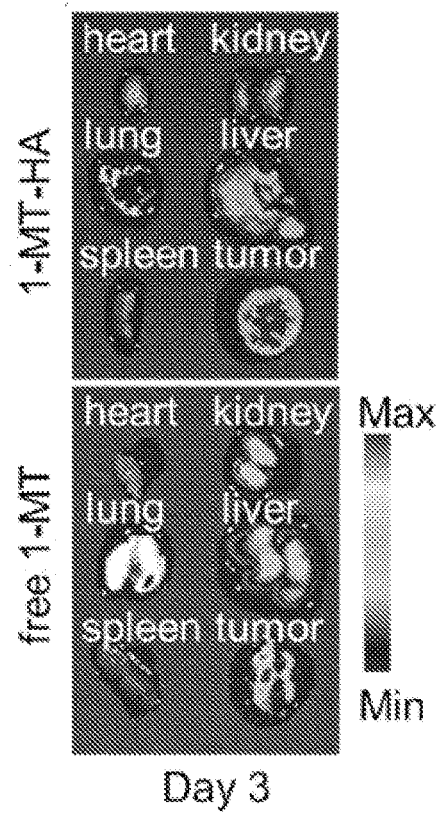
Figure 19H:
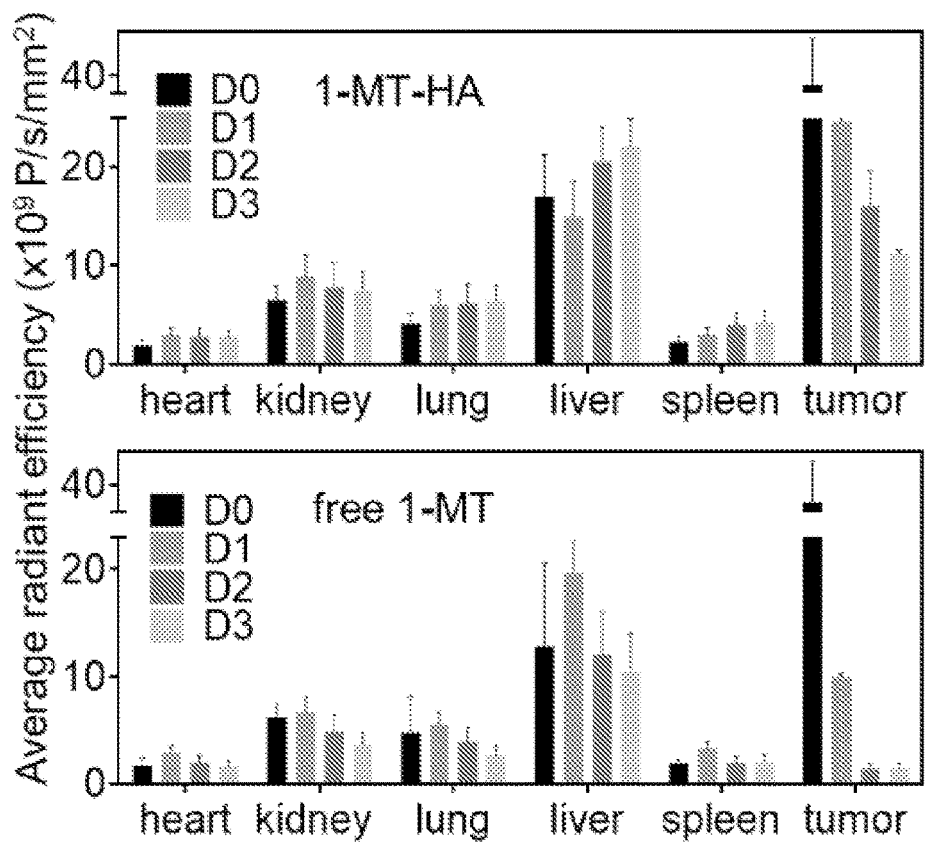
Figure 19I:
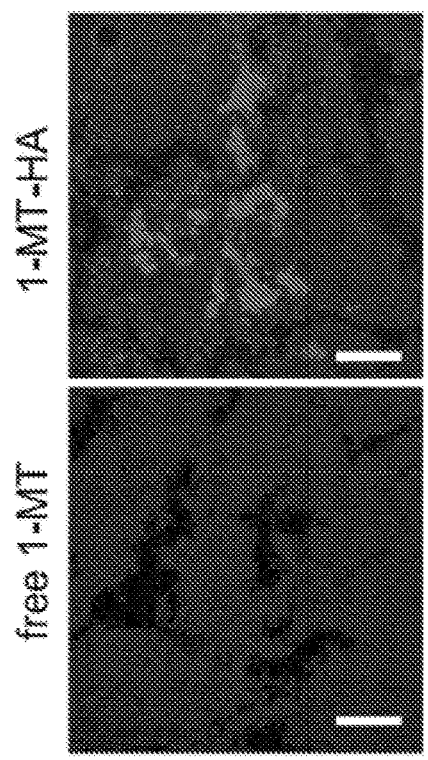
Figure 20A:
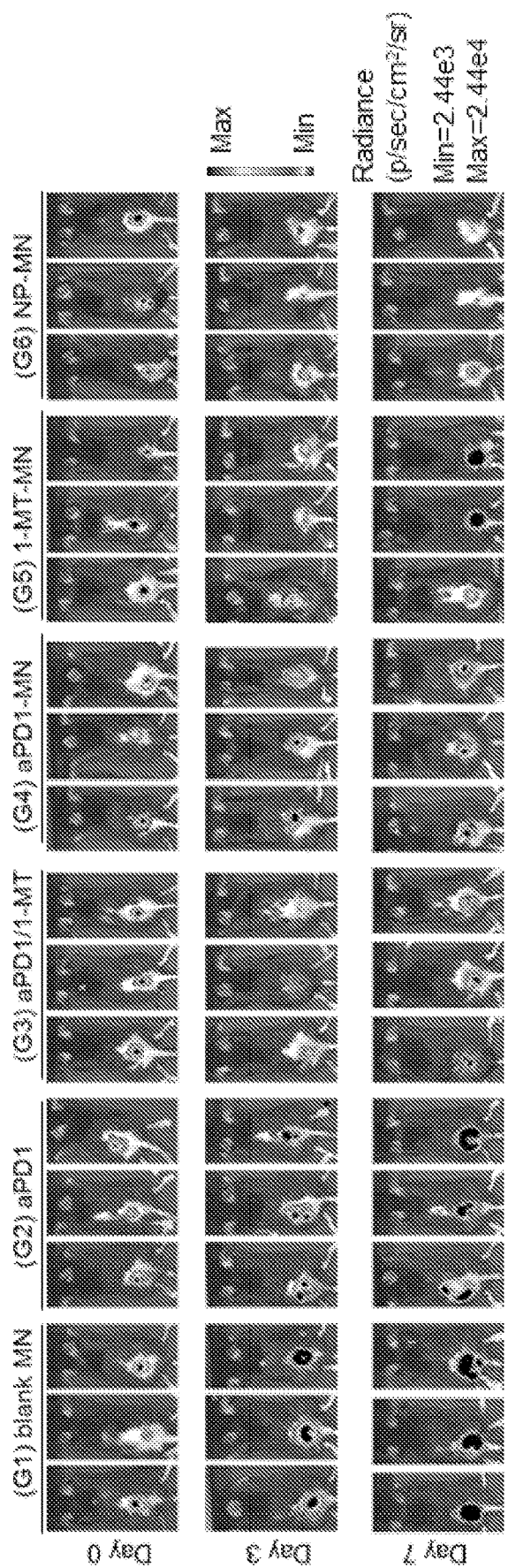
FIGS. 20A-20E. The synergistic therapy elicited robust tumor regression for B16F10 melanoma mice models.
Figure 20B:
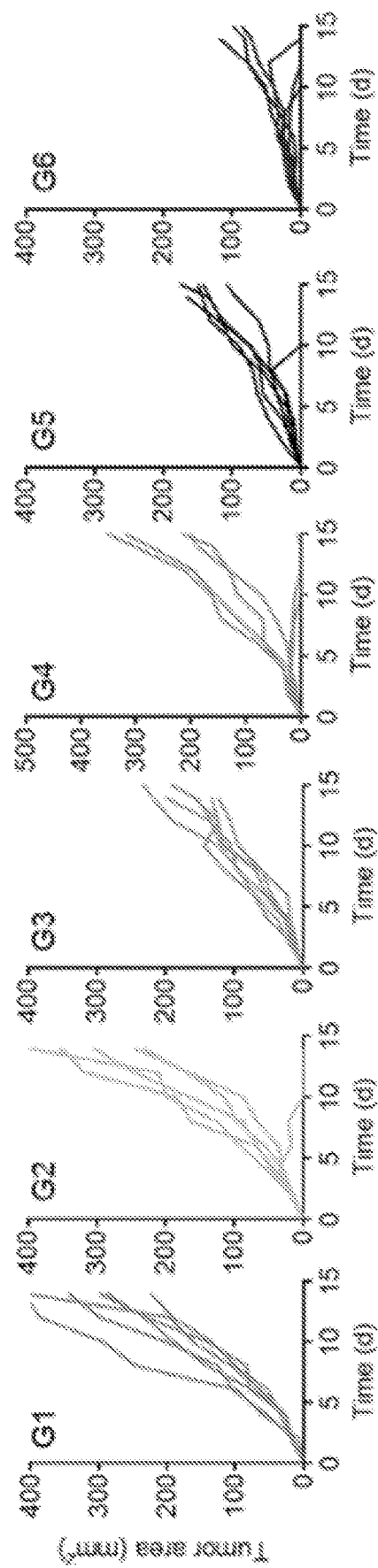
Figure 20C:
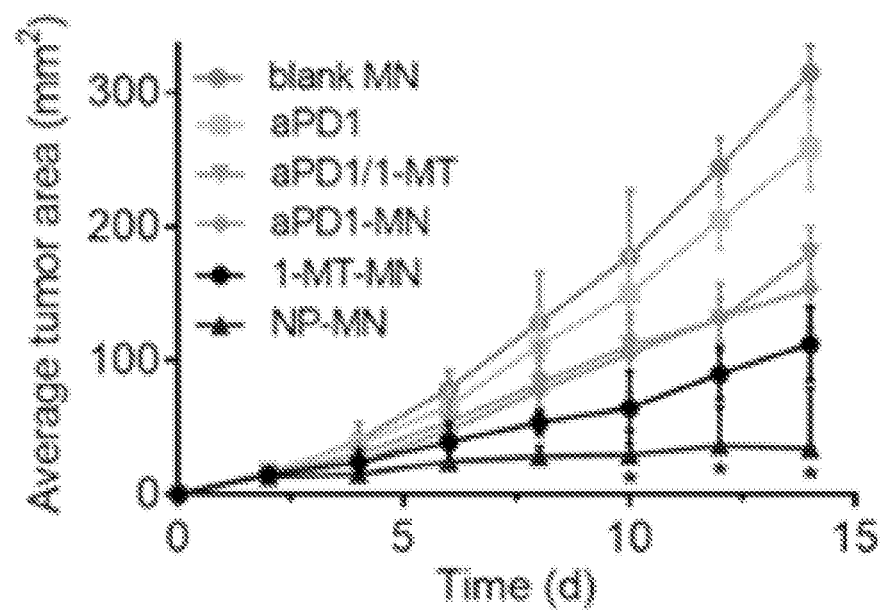
Figure 20D:
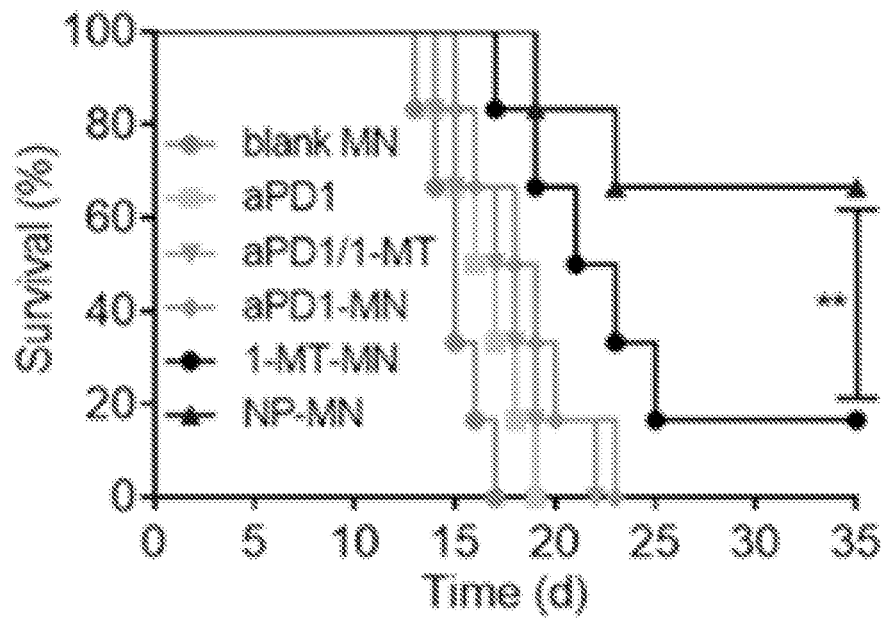
Figure 20E:
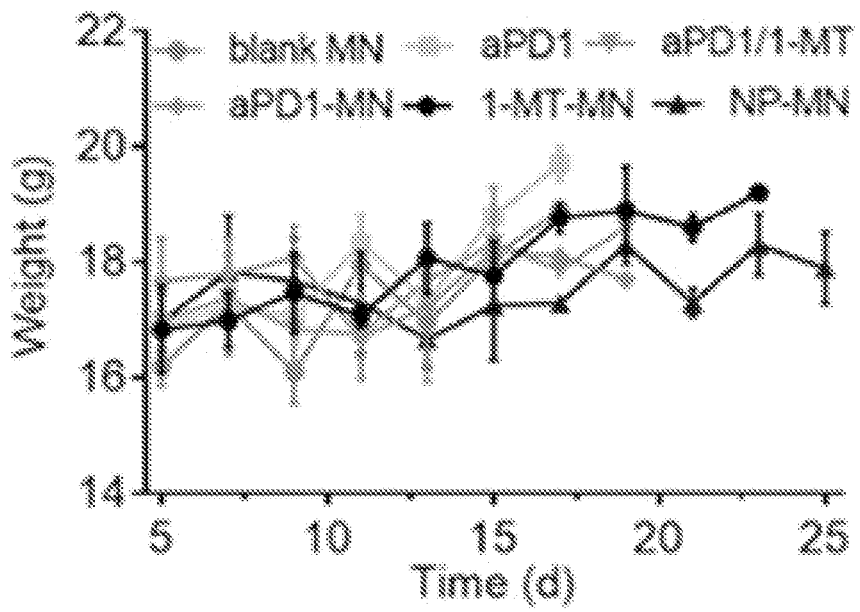
Figure 21A:
FIGS. 21A-21D. The synergistic therapy integrated with microneedles triggered an enhanced anti-tumor immune response.
Figure 21B:
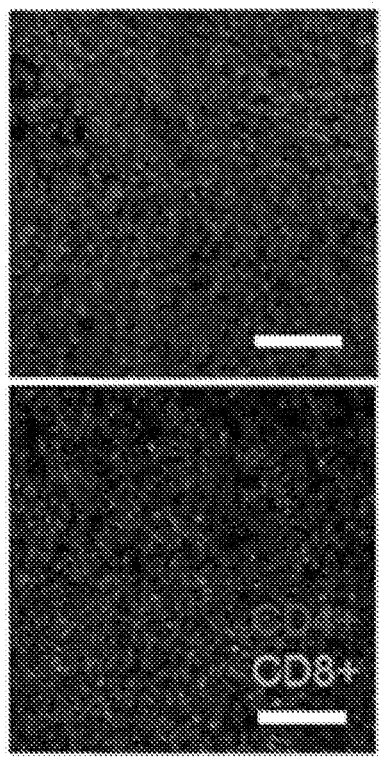
Figure 21C:
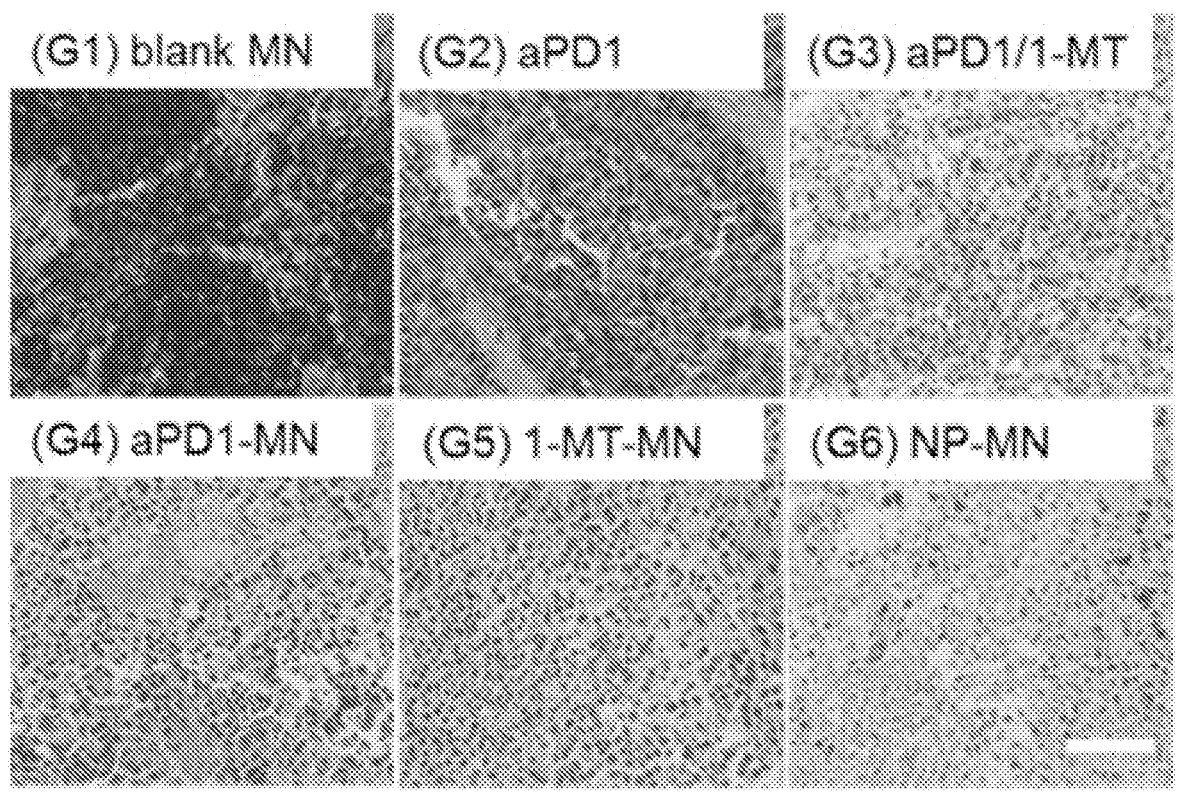
Figure 21D:
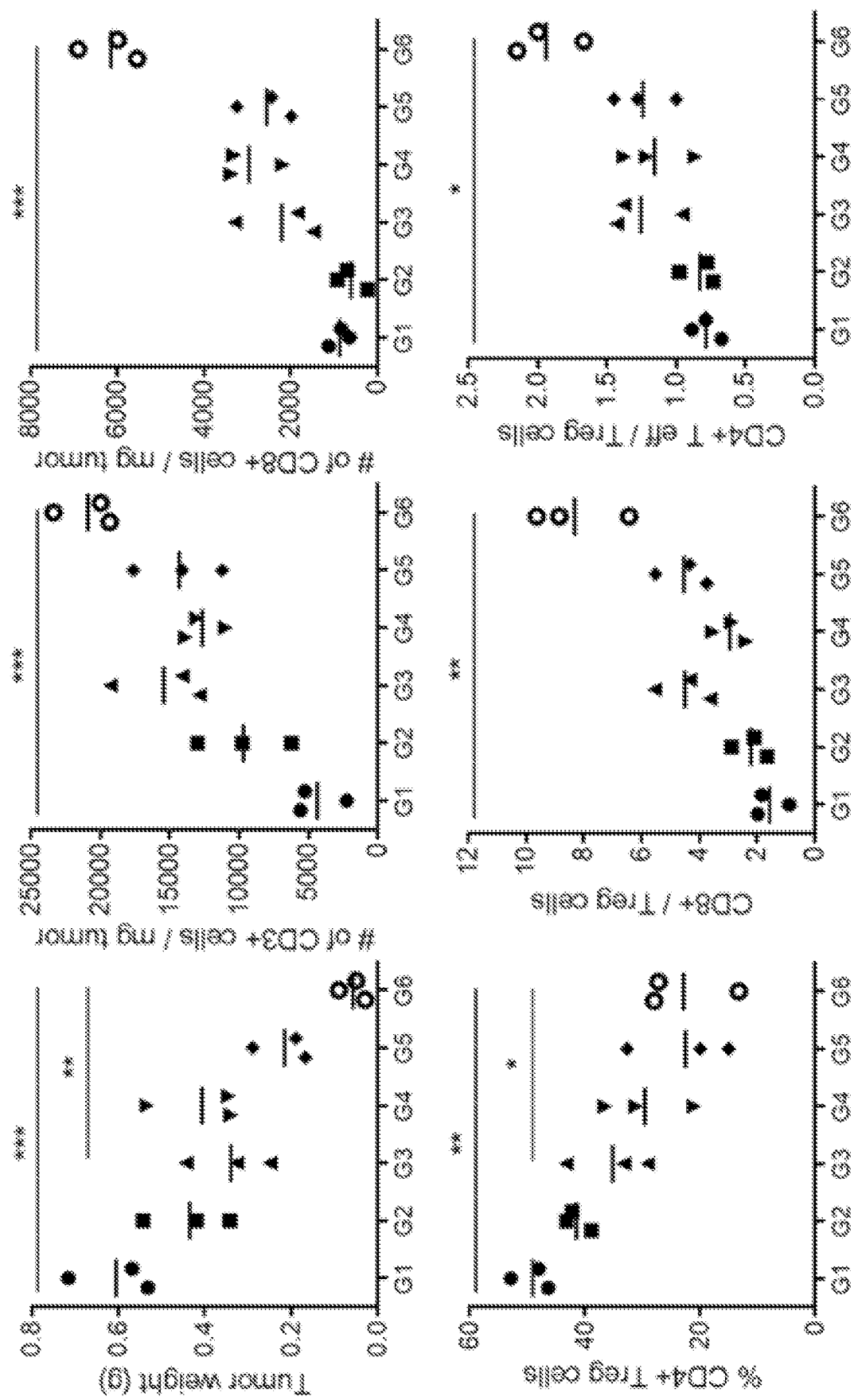

To investigate the immunologic mechanisms behind the enhanced therapeutic effects of the formulation, tumor-infiltrating lymphocytes (TILs) from relapsed tumors were harvested and analyzed by the flow cytometry and immunofluorescence 10 days after surgery. It was verified that HhaI-TGMS-DNCs-aPD1 combined treatment increased both the percentage and absolute numbers of activated CD8+ T cells (CD8+CD44+CD62L−) in the relapsed tumors (FIG. 3D-E). Immunofluorescence staining also revealed that the untreated relapsed tumors had limited T-cell infiltration (FIG. 3F). In contrast, tumors from HhaI-TGMS-DNCs-aPD1 treated mice were remarkably infiltrated by both CD8+ and CD4+ T cells. When absolute cell numbers and the mass of the pooled tumors were accounted for in the analysis, the total CD8+ T cells per mg of tumor in HhaI-TGMS-DNCs-aPD1 combination-treated mice increased 2-fold over free aPD1/free CpG nucleotides and HhaI-TGMS-cDNCs-aPD1 treated mice, and 10-fold over HhaI-TGMS-DNCs treatment and PBS controls (FIG. 3G). Besides, the tumor-infiltrating CD4+FoxP3+ T cells were also studied (FIG. 17). Likewise, the effective CD4+ cells were increased in combination-treated tumors as well compared with control groups. Collectively, the combination treatment not only increased the ratio of CD8+ T cells to Tregs, but also increased effective CD4+ T cells to Tregs (FIG. 3H).

Figure 4A:
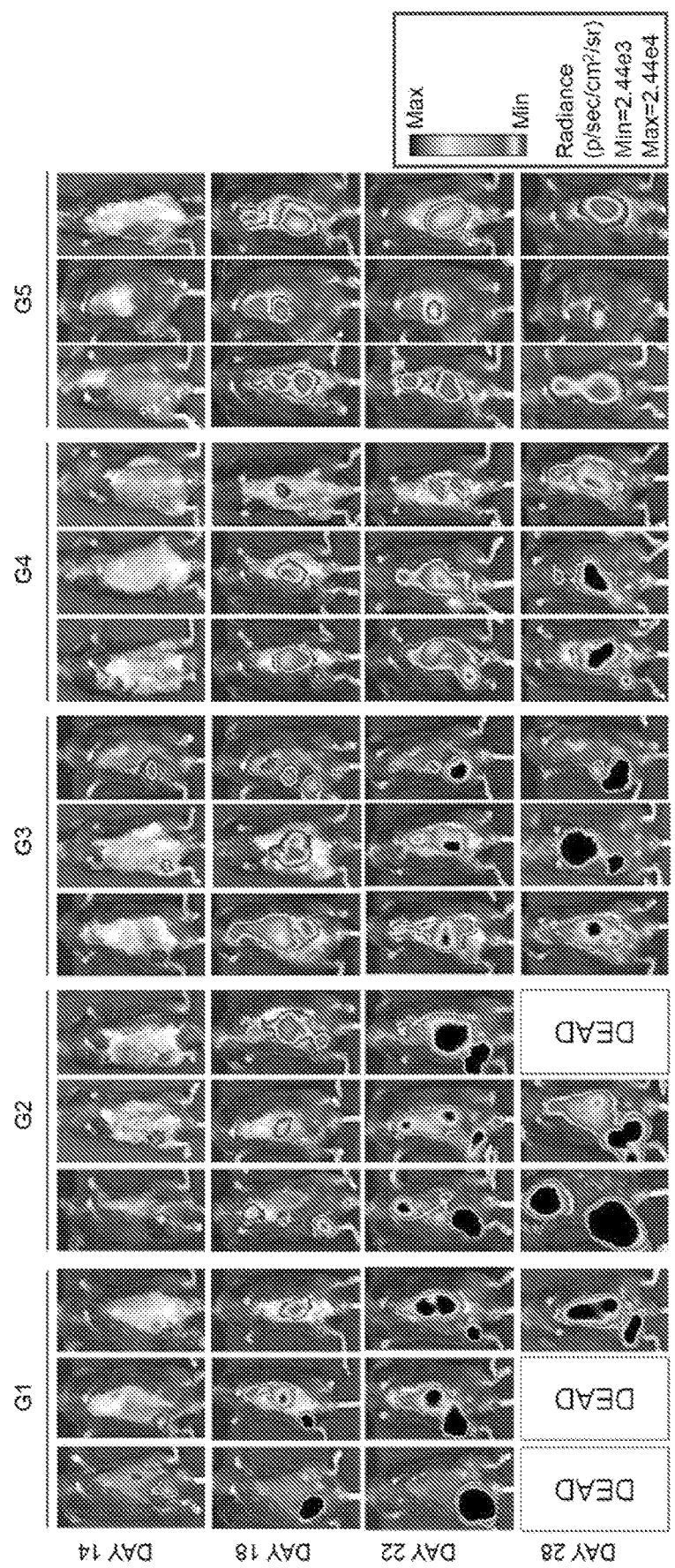
FIGS. 4A-4F. Systemic antitumor efficacy could be obtained by the local injection of DNC delivery system at the surgical site.
Figure 4B:
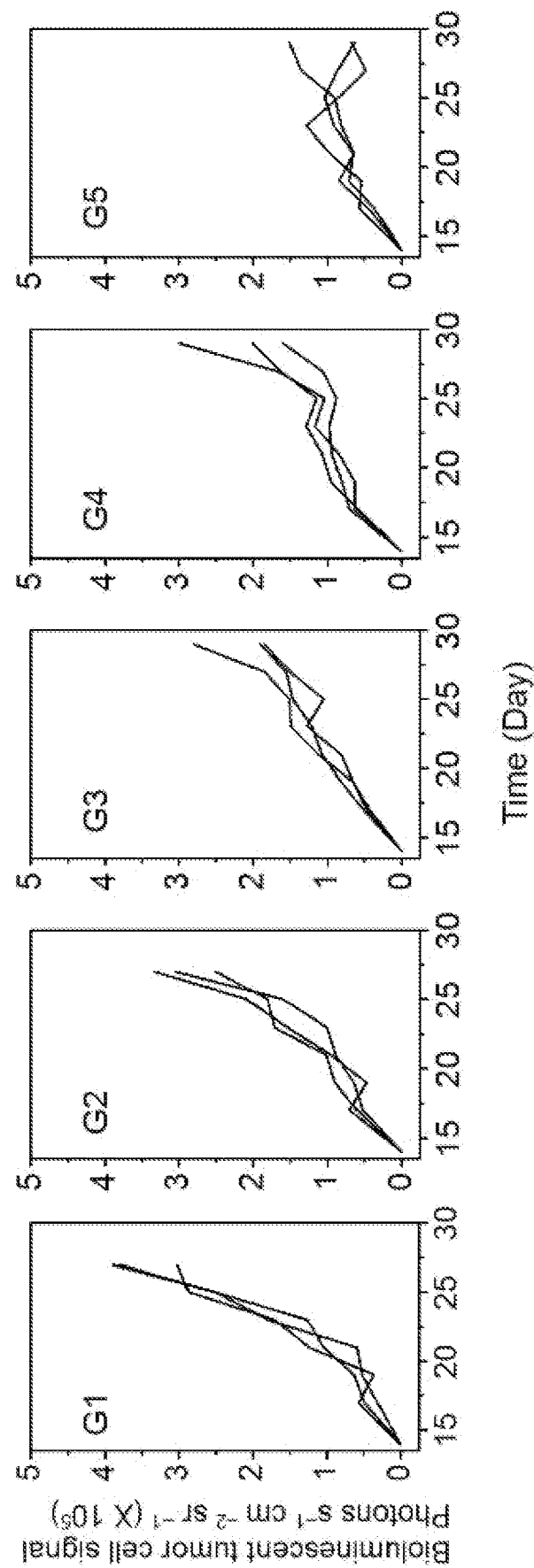
Figure 4C:
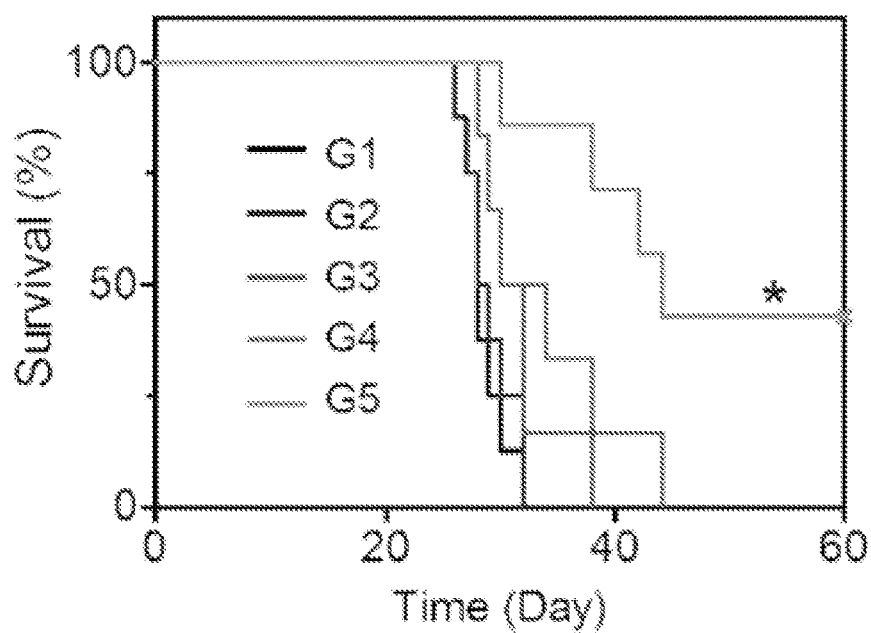
Figure 4D:
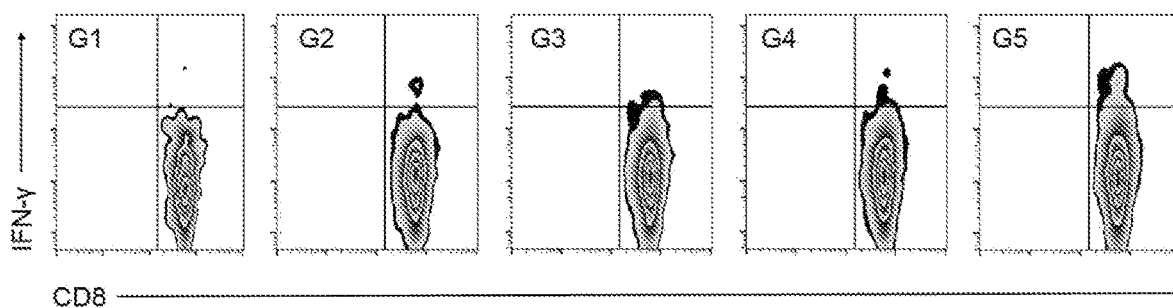
Figure 4E:
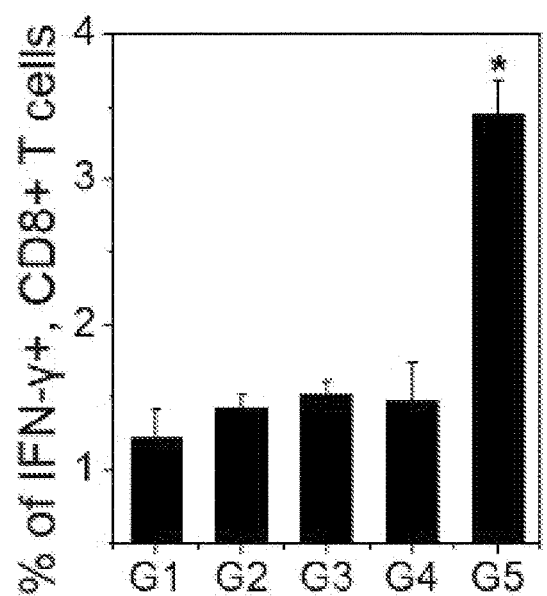
Figure 4F:
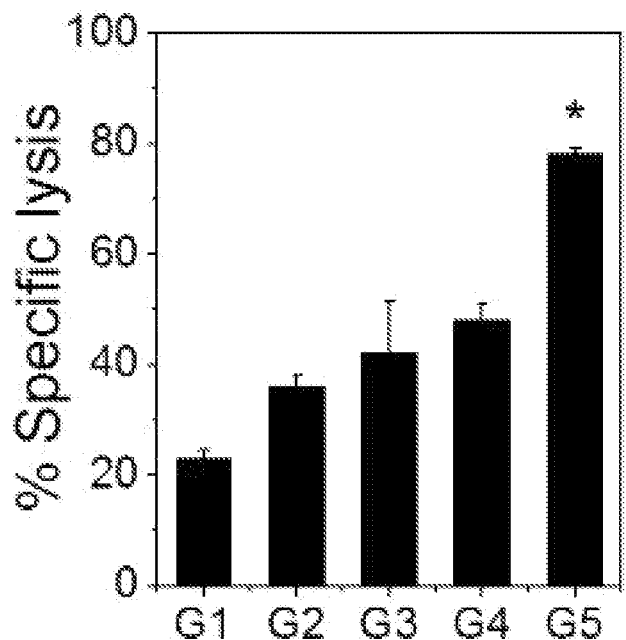

To further demonstrate the potency of this formulation, it was tested in a metastasis tumor model by challenging mice with i.v. injection of luciferase expressing B16F10 cells one day before surgery. After incomplete surgery to remove the most primary tumor, the mice were peritumorally injected with single dose of different formulations as indicated, including PBS control (Group 1 (G1)), HhaI-TGMS-DNCs (G2), HhaI-TGMS-cDNCs (including cutting sites of HhaI without CpG sequence)-aPD1 (G3), free aPD1/free CpG nucleotides (G4) and HhaI-TGMS-DNCs-aPD1 (G5) (aPD1, 0.5 mg/kg. DNA, 10 mg/kg). The systemic antitumor immune response generated by injection of HhaI-TGMS-DNCs-aPD1 after surgery was clearly observed (FIG. 4A-B). Both the primary tumor and the disseminated tumors showed significantly delayed growth, with 40% of mice surviving 40 days. In sharp contrast, the antitumor immune response generated by the control groups had little effect on the distant metastasis in multiple organs, and showed negligible improvement of survival compared to the untreated groups (FIG. 4C). Splenocyte responses were examined by measuring their production of IFN-γ. Splenocytes harvested from mice in the 30th day were treated with irradiated B16F10 cell for 16 h. It was shown that after HhaI-TGMS-DNCs-aPD1 treatment, the proportion of IFN-γ-secreting CD8 T cells in the spleen increased approximately 2-3 fold in mice compared to the control groups (FIG. 4D-E). Moreover, enhanced cytotoxic responses were also observed when incubated the splenocytes to B16F10 cancer cells in vitro (FIG. 4F). Taken together, the systemic antitumor efficacy can be achieved by locally injecting HhaI-TGMS-DNCs-aPD1 into the operative site, eradicating tumors in situ as well as disseminating metastasized tumors.

In summary, disclosed in this example is a local delivery system for cancer immunotherapy that can substantially improve the ability of the anticancer immune response to treat the remaining or metastasic tumors after the resection of primary tumors. The novel CpG DNA-based carrier not only served as a therapeutic loading matrix for aPD1, but can also enhance treatment efficacy after fragmentation of the CpG DNA. The sustained release and synergistic action of aPD1 and CpG ODNs in tumor sites can be activated by the inflammatory microenvironment induced by operation. It was substantiated that the bio-responsive controlled release of CpG and aPD1 was more effective than free CpG nucleotides and aPD1. The controlled release can also prevent the risk of toxic peak dosage of aPD1 in the body.

REFERENCES CITED IN THIS EXAMPLE

The disclosures of all articles and references, including patent applications and publications, are incorporated by reference for all purposes.

(1) Paik, S.; Shak, S.; Tang, G.; Kim, C.; Baker, J.; Cronin, M.; Baehner, F. L.; Walker, M. G.; Watson, D.; Park, T. *New England Journal of Medicine* 2004, 351, 2817.
(2) Vakkila, J.; Lotze, M. T. *Nat. Rev. Immunol.* 2004, 4, 641.
(3) Coffey, J. C.; Wang, J.; Smith, M.; Bouchier-Hayes, D.; Cotter, T.; Redmond, H. *Lancet Oncol.* 2003, 4, 760.
(4) Demicheli, R.; Retsky, M.; Hrushesky, W.; Baum, M.; Gukas, I. *Ann. Oncol.* 2008, mdn386.
(5) Grivennikov, S. I.; Greten, F. R.; Karin, M. *Cell* 2010, 140, 883.
(6) Ceelen, W.; Pattyn, P.; Mareel, M. *Crit. Rev. Oncol. Hematol.* 2014, 89, 16.
(7) Segatto, I.; Berton, S.; Sonego, M.; Massarut, S.; Perin, T.; Piccoli, E.; Colombatti, A.; Vecchione, A.; Baldassarre, G.; Belletti, B. *Oncotarget* 2014, 5, 6267.
(8) Antonio, N.; Bonnelykke-Behrndtz, M. L.; Ward, L. C.; Collin, J.; Christensen, I. J.; Steiniche, T.; Schmidt, H.; Feng, Y.; Martin, P. *EMBO J.* 2015, 34, 2219.
(9) Baker, D.; Masterson, T.; Pace, R.; Constable, W.; Wanebo, H. *Surgery* 1989, 106, 525.
(10) Albain, K.; Swann, R.; Rusch, V.; Turrisi, A.; Shepherd, F.; Smith, C.; Gandara, D.; Johnson, D.; Green, M.; Miller, R. In *ASCO Annual Meeting Proceedings* 2005; Vol. 23, p 7014.
(11) Stephan, S. B.; Taber, A. M.; Jileaeva, I.; Pegues, E. P.; Sentman, C. L.; Stephan, M. T. *Nat. Biotechnol.* 2015, 33, 97.
(12) Kwon, E. D.; Foster, B. A.; Hurwitz, A. A.; Madias, C.; Allison, J. P.; Greenberg, N. M.; Burg, M. B. *Proc. Natl. Acad. Sci. U.S.A* 1999, 96, 15074.
(13) Liu, Q.; Zhai, B.; Yang, W.; Yu, L.-X.; Dong, W.; He, Y.-Q.; Chen, L.; Tang, L.; Lin, Y.; Huang, D.-D. *Molecular Therapy* 2009, 17, 2049.
(14) Gubin, M. M.; Zhang, X.; Schuster, H.; Caron, E.; Ward, J. P.; Noguchi, T.; Ivanova, Y.; Hundal, J.; Arthur, C. D.; Krebber, W.-J. *Nature* 2014, 515, 577.
(15) Pardoll, D. M. *Nat. Rev. Cancer* 2012, 12, 252.
(16) Wang, C.; Xu, L. G.; Liang, C.; Xiang, J.; Peng, R.; Liu, Z. *Adv. Mater.* 2014, 26, 8154.
(17) Curran, M. A.; Montalvo, W.; Yagita, H.; Allison, J. P. *Proc. Natl. Acad. Sci. U.S.A.* 2010, 107, 4275.
(18) Ribas, A. *N. Engl. J. Med.* 2015, 373, 1490.
(19) Mitragotri, S.; Burke, P. A.; Langer, R. *Nat. Rev. Drug Discovery* 2014, 13, 655.
(20) Patnaik, A.; Kang, S. P.; Tolcher, A. W.; Rasco, D. W.; Papadopoulos, K. P.; Beeram, M.; Drengler, R.; Chen, C.; Smith, L.; Perez, C. In *ASCO Annual Meeting Proceedings* 2012; Vol. 30, p 2512.
(21) Topalian, S. L.; Hodi, F. S.; Brahmer, J. R.; Gettinger, S. N.; Smith, D. C.; McDermott, D. F.; Powderly, J. D.; Carvajal, R. D.; Sosman, J. A.; Atkins, M. B. *N. Engl. J. Med.* 2012, 366, 2443.
(22) Sabado, R. L.; Bhardwaj, N. *Nature* 2015, 519, 300.
(23) Naidoo, J.; Page, D. B.; Li, B. T.; Connell, L. C.; Schindler, K.; Lacouture, M. E.; Postow, M. A.; Wolchok, J. D. *Ann. Oncol.* 2015, mdv383.
(24) Hamid, O.; Robert, C.; Daud, A.; Hodi, F. S.; Hwu, W.-J.; Kefford, R.; Wolchok, J. D.; Hersey, P.; Joseph, R. W.; Weber, J. S. *N. Engl. J. Med.* 2013, 369, 134.
(25) Mellati, M.; Eaton, K. D.; Brooks-Worrell, B. M.; Hagopian, W. A.; Martins, R.; Palmer, J. P.; Hirsch, I. B. *Diabetes Care* 2015, 38, e137.
(26) Topalian, S. L.; Sznol, M.; McDermott, D. F.; Kluger, H. M.; Carvajal, R. D.; Sharfman, W. H.; Brahmer, J. R.; Lawrence, D. P.; Atkins, M. B.; Powderly, J. D. *Journal of Clinical Oncology* 2014, 32, 1020.
(27) Fadel, T. R.; Sharp, F. A.; Vudattu, N.; Ragheb, R.; Garyu, J.; Kim, D.; Hong, E.; Li, N.; Haller, G. L.; Pfefferle, L. D. *Nat. Nanotechnol.* 2014, 9, 639.
(28) Kim, J.; Li, W. A.; Choi, Y.; Lewin, S. A.; Verbeke, C. S.; Dranoff, G.; Mooney, D. *J. Nat. Biotechnol.* 2015, 33, 64.
(29) Stephan, M. T.; Moon, J. J.; Um, S. H.; Bershteyn, A.; Irvine, D. *J. Nat. Med.* 2010, 16, 1035.
(30) Park, J.; Wrzesinski, S. H.; Stern, E.; Look, M.; Criscione, J.; Ragheb, R.; Jay, S. M.; Demento, S. L.; Agawu, A.; Licona Limon, P.; Ferrandino, A. F.; Gonzalez, D.; Habermann, A.; Flavell, R. A.; Fahmy, T. M. *Nat. Mater.* 2012, 11, 895.
(31) Goldberg, M. S. Cell 2015, 161, 201.
(32) Huang, B. N.; Abraham, W. D.; Zheng, Y. R.; Lopez, S. C. B.; Luo, S. S.; Irvine, D. *J. Sci. Transl. Med.* 2015, 7, 291ra94.
(33) Irvine, D. J.; Hanson, M. C.; Rakhra, K.; Tokatlian, T. *Chem. Rev.* 2015, 115, 11109.
(34) Nochi, T.; Yuki, Y.; Takahashi, H.; Sawada, S.-i.; Mejima, M.; Kohda, T.; Harada, N.; Kong, I. G.; Sato, A.; Kataoka, N. *Nat. Mater.* 2010, 9, 572.
(35) Mura, S.; Nicolas, J.; Couvreur, P. *Nat. Mater.* 2013, 12, 991.
(36) Marabelle, A.; Kohrt, H.; Sagiv-Barfi, I.; Ajami, B.; Axtell, R. C.; Zhou, G.; Rajapaksa, R.; Green, M. R.; Torchia, J.; Brody, J. *J. Clin. Invest.* 2013, 123, 2447.
(37) Krieg, A. M. *Oncogene* 2008, 27, 161.
(38) Jones, M. R.; Seeman, N. C.; Mirkin, C. A. *Science* 2015, 347, 1260901.
(39) Gajanayake, T.; Olariu, R.; Leclére, F. M.; Dhayani, A.; Yang, Z.; Bongoni, A. K.; Banz, Y.; Constantinescu, M. A.; Karp, J. M.; Vemula, P. K. *Sci. Transl. Med.* 2014, 6, 249ra110.
(40) Karp, J. M.; Vemula, P. K.; Campbell, N. R.; Syed, A. M.; Zhang, S.; Farokhzad, O. C.; Langer, R. S.; Google Patents: 2011.
(41) Sun, W.; Ji, W.; Hall, J. M.; Hu, Q.; Wang, C.; Beisel, C. L.; Gu, Z. *Angew. Chem. Int. Ed.* 2015, 54, 12029.
(42) Sun, W.; Jiang, T.; Lu, Y.; Reiff, M.; Mo, R.; Gu, Z. *J. Am. Chem. Soc.* 2014, 136, 14722.
(43) Ali, M. M.; Li, F.; Zhang, Z.; Zhang, K.; Kang, D. K.; Ankrum, J. A.; Le, X. C.; Zhao, W. *Chem. Soc. Rev.* 2014, 43, 3324.
(44) Roh, Y. H.; Lee, J. B.; Shopsowitz, K. E.; Dreaden, E. C.; Morton, S. W.; Poon, Z.; Hong, J.; Yamin, I.; Bonner, D. K.; Hammond, P. T. *ACS Nano* 2014, 8, 9767.
(45) Lv, Y.; Hu, R.; Zhu, G.; Zhang, X.; Mei, L.; Liu, Q.; Qiu, L.; Wu, C.; Tan, W. *Nature protocols* 2015, 10, 1508.
(46) Ryan, T. J. *Australas. J. Dermatol.* 1994, 35, 35.
(47) Armstrong, D. G.; Jude, E. B. *J. Am. Podiatr. Med. Assoc.* 2002, 92, 12.

Example 2. Synergistically Transcutaneous Immunotherapy Enhances Antitumor Immune Responses Through Blockade of PD1 and IDO Recent developments in cancer immunology have demonstrated the paramount importance of immunoregulatory approaches in treating cancer.[1-4] Among them, the immune checkpoint inhibitor programmed cell death protein 1 is a potent negative regulator of the tumor-infiltrating lymphocytes (TILs).[5-6] Tumor cells and antigen presenting cells (APCs) engage the PD1/PDL1 (programmed death-ligand 1) interaction which leads to T cell apoptosis, anergy or exhaustion.[7] Blocking PD1 function with monoclonal antibodies results in augmented T cell responses and long-term remissions in various types of tumors.[8-9] In clinic trials for advanced melanoma, anti-PD1 antibody (aPD1) treatment elicited significantly longer progression-free survival and has been approved by the US Food and Drug Administration (FDA).[10-13] However, the clinical benefit of aPD1 therapy has been restricted to only a fraction of patients.[14] This effect is likely to be impaired by inefficient infiltration of lymphocytes in the evolution of immune evasion.[15] For example, the tumors can trigger a variety of immunosuppressive molecules, such as indoleamine 2,3-dioxygenase (IDO) in regulatory dendritic cells (DC), which catalyzes the degradation of the tryptophan and limits the T-cell function. Moreover, regulatory T cells can be attracted by the upregulation of IDO expression, which would oppose an antitumor response significantly.[16-18] Meanwhile, the potential immune-related adverse events also impose major challenges, owing to the off-target binding of antibodies to normal tissues after traditional systematic administration.[19]

To overcome these challenges, microneedle (MN)-based transcutaneous delivery platform for the synergistic checkpoint blockade of PD1 and IDO in the tumor microenvironment were developed.[20-25] Pharmacological inhibition of IDO with 1-methyl-DL-tryptophan (1-MT) has been demonstrated to enhance T cell-dependent antitumor immunity.[15, 26-27] The orally administrated NLG2101 is currently under a phase Ib/II trial dose-escalating clinical study for the treatment of metastatic breast, brain, melanoma and pancreatic cancer.[17] Limiting the immunosuppression by IDO inhibitor can thus maximize the therapeutic effects of PD1 blockade. The strategy employed in this example is to design the covalently conjugated 1-MT toward hyaluronic acid (m-HA) to form an amphiphilic structure, and readily construct nanoparticles (NPs) by self-assembly to encapsulate aPD1.[28-31] This formulation method based on the combination strategy of "drug A in carriers formed by incorporation of drug B" effectively facilitates the loading capacity of therapeutics.[32-34] Integrated into the MN system, the combinational therapeutics can be transported across the stratum corneum and readily accumulated in the network of skin-resident DCs around the local tumor.[21, 35-39] The MN-based sustained delivery platform can enhance the local retention of such agents, improving their effect on tumor-infiltrating lymphocytes and reducing the toxicity resulting from leakage into the systemic circulation. Meanwhile, the drug release can be activated by the enzymatic digestion of HA at the tumor site with the assistance of hyaluronidase (HAase), an overexpressed enzyme in the tumor microenvironment.[40] The release of the small molecule 1-MT from the m-HA can block the immune-inhibitory pathways in the tumor microenvironment. Meanwhile, the subsequently triggered release of aPD1 exerted the PD1 blockade in the context of increased alloreactive T-cell population (FIG. 1). Using a B16F10 mouse melanoma model, it was demonstrated that the synergistic delivery of aPD1 and 1-MT elicited potent and sustained antitumor effect, which was accompanied with enhanced effector T cell immunity as well as reduced immunosuppression in the tumor environment.

Results and Discussion

Figure 22:
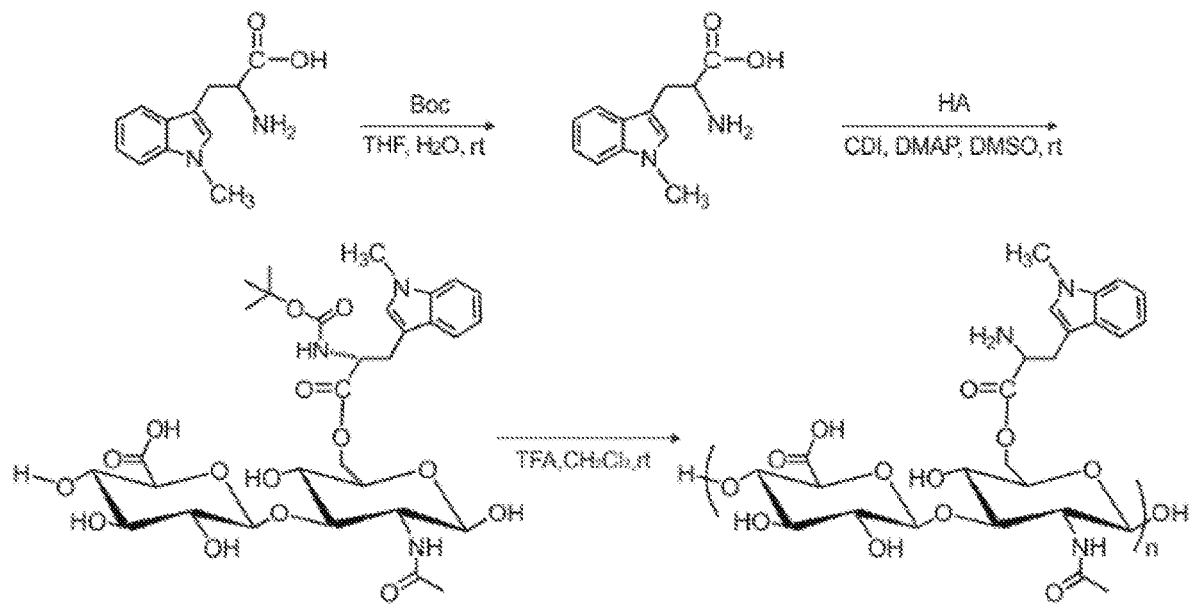
FIG. 22. The conjugation mechanism of m-HA
Figure 23:
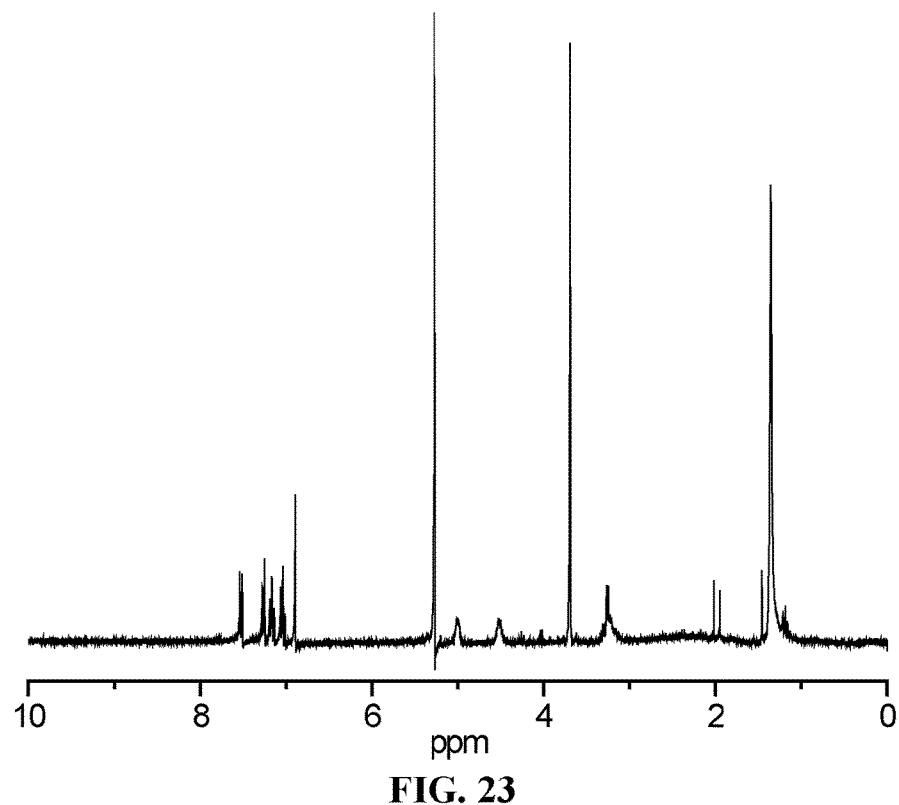
FIG. 23. $^1$H NMR of Boc-MT. $^1$H NMR ($d_6$-$CD_2Cl_2$, 300 MHz, δ ppm): δ 7.49-7.43 (d, 1H, Ar—H), 7.32-7.25 (d, 1H, Ar—H), 7.08-7.01 (m, 1H, Ar—H), 6.97-6.89 (m, 1H, Ar—H), 6.85-6.78 (s, 1H, C—$H_{N\text{-}methylindole}$), 4.07 (s, 1H, NH), 3.64 (s, 2H, $CH_2$), 2.81 (s, 1H, CH), 2.41 (s, 3H, N—$CH_3$), 1.25 (s, 9H, $C(CH_3)_3$).
Figure 24:
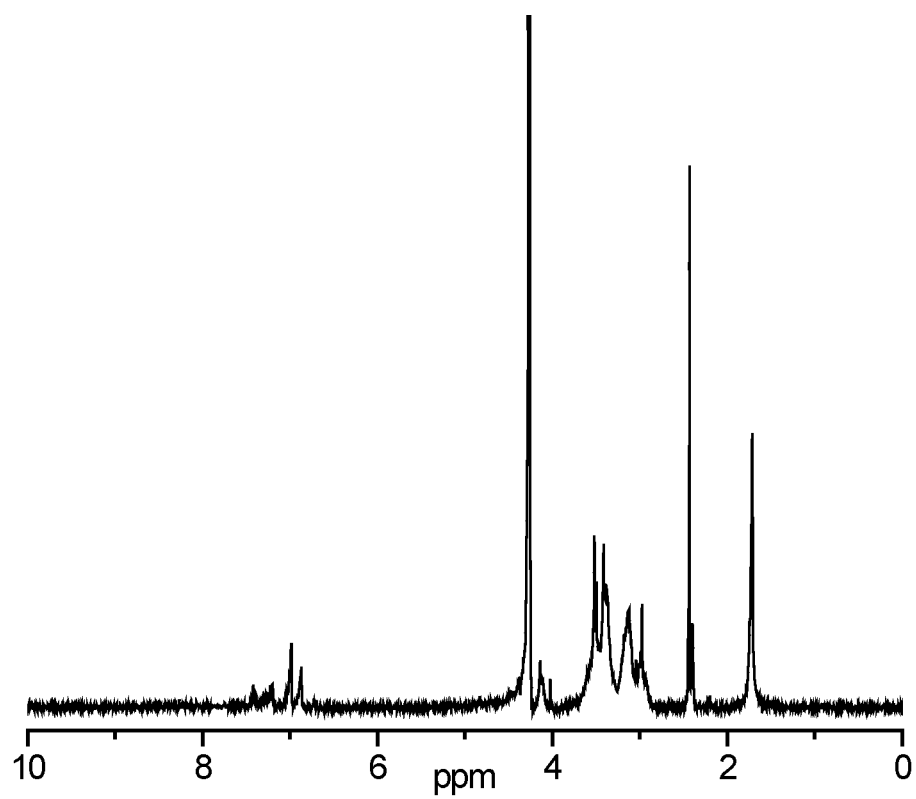
FIG. 24. $^1$H NMR of m-HA. m-HA: $^1$H NMR ($D_2O$, 300 MHz, δ ppm): δ 7.49-6.78 (m, 1.17H, 1-MT), 1.82-1.63 (m, 8H, $NH_2CH_2(CH_2)_4$).
Figure 25:
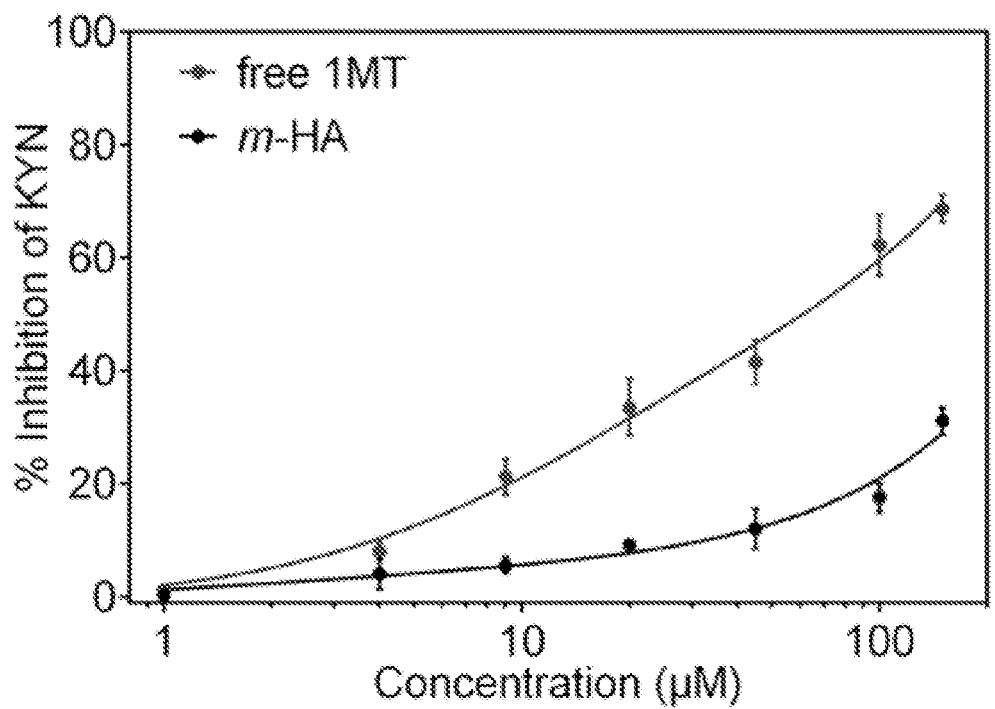
FIG. 25. IDO enzyme activity was measured as the inhibition of kynurenine production after the free 1-MT and m-HA treatment. Error bars indicate SD (n=3).

The solvent dialysis approach was employed to prepare the self-assembly of 1-MT conjugated HA (m-HA, MW=50 kDa) encapsulating monoclonal aPD1.[41] The m-HA was prepared via the formation of ester bond between HA and amine-protected 1-MT (FIG. 22-24). The functional DO inhibition was tested by HeLa cells with the constitutive expression of DO after IFN-γ stimulation (FIG. 25).[42-43]

Figure 26:
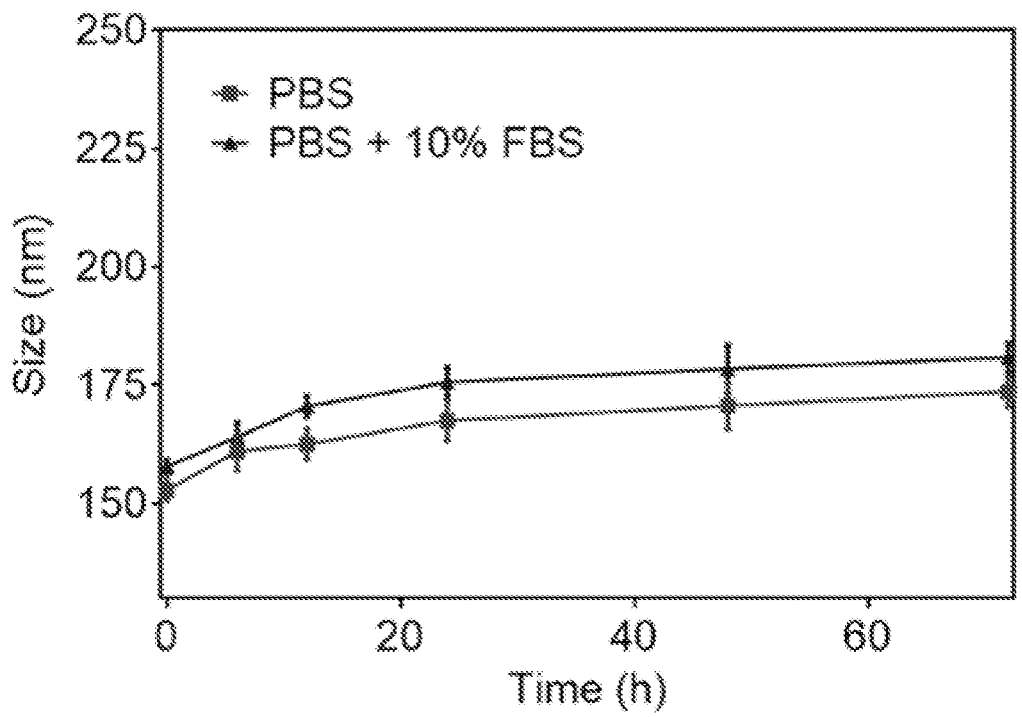
FIG. 26. In vitro stability of aPD1 loaded HA-NPs in PBS and 10% FBS. Error bars indicate SD (n=3).
Figure 27:
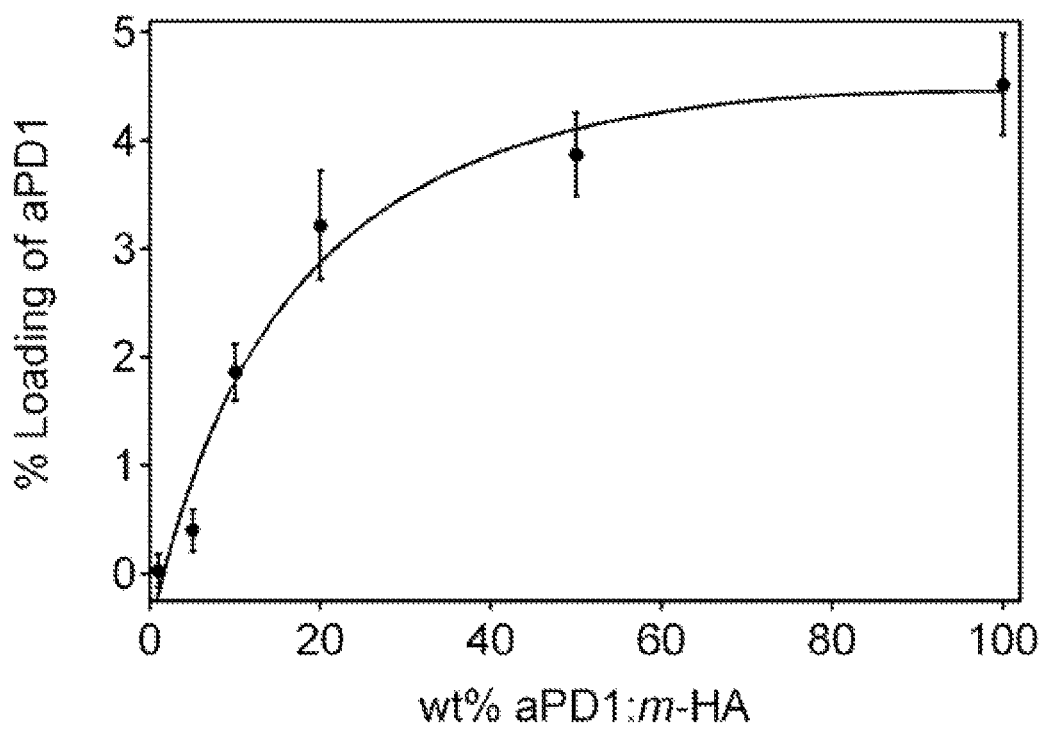
FIG. 27. Loading capacity of aPD1 at different weight ratio between aPD1 and m-HA. Error bars indicate SD (n=3).
Figure 28:
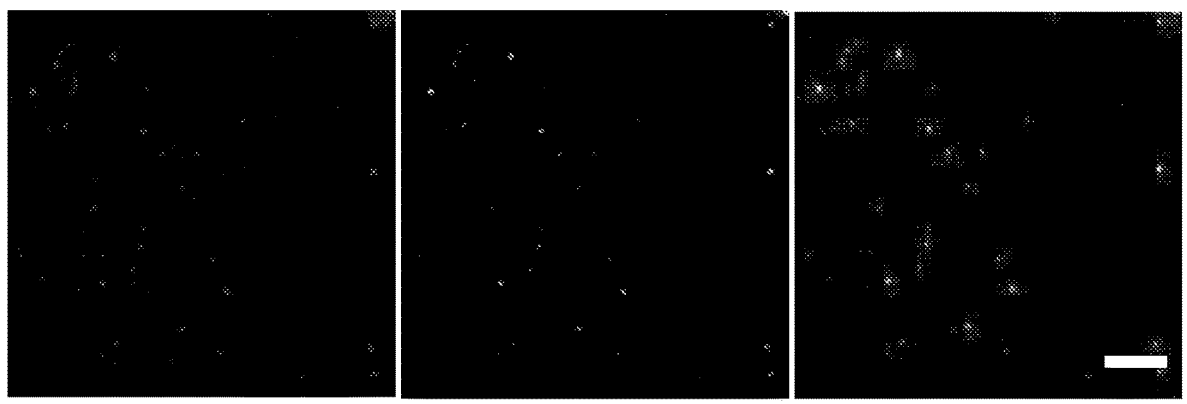
FIG. 28. The encapsulation of aPD1 inside the NP was visualized by the co-localization of aPD1 (green) and the 1-MT (red) using confocal microscopy.

Given the modification of m-HA with the hydrophobic indolic ring structure of 1-MT, the amphiphilic HA enabled the self-assembly of NPs in the aqueous solution. As shown in the transmission electron microscopy (TEM) image, the resulting HA based NPs (HA-NPs) had a spherical shape with a monodisperse size distribution. The average diameter of NPs in DI water was determined as 151 nm by the dynamic light scattering (DLS) (FIG. 1b), which was consistent with the observation by TEM. The aPD1 loaded HA-NPs were stable in PBS and 10% FBS solution with negligible size difference for 72 h (FIG. 26). The zeta-potential of HA-NPs was measured as −17.1±0.2 mV due to the carboxyl groups of the HA. The aPD1 was loaded in the inner structure during the HA-NPs formation, due to the hydrophobic and electrostatic nonspecific-interaction.[29] The loading capacity of aPD1 was determined as 4.5% (wt/wt) by the ELISA (FIG. 27). Additionally, the successful incorporation of aPD1 was further substantiated by the co-localization of the Cy5.5-labeled aPD1 and rhodamine B-surrogated 1-MT (FIG. 28). The obtained HA-NPs were highly stable, without showing appreciable precipitation at 4° C. within five days in PBS.

Figure 1C:
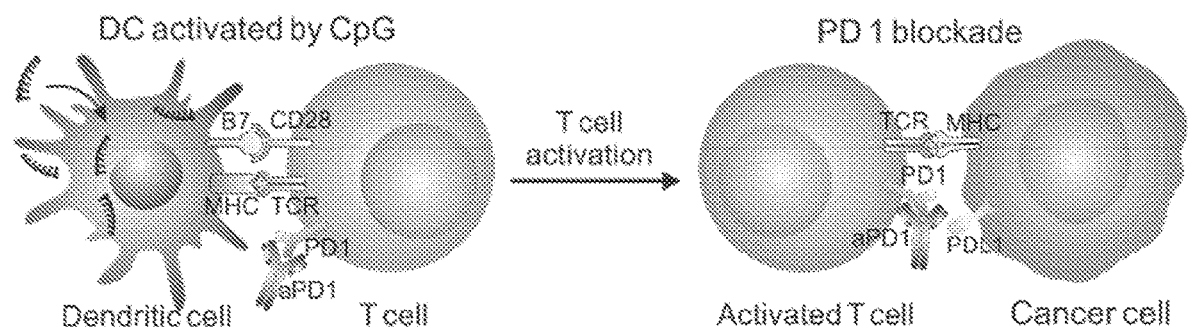
Figure 29:
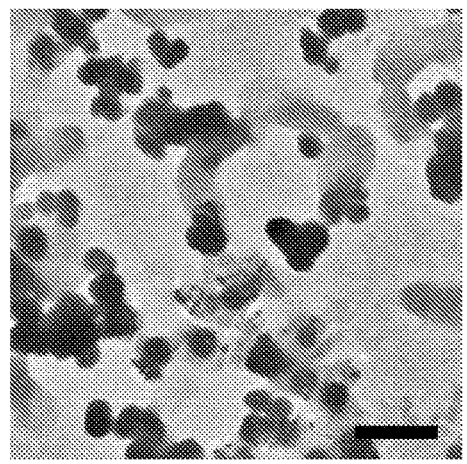
FIG. 29. The morphology of NPs after 4 h HAase treatment characterized by TEM (scale bar: 200 nm).
Figure 30:
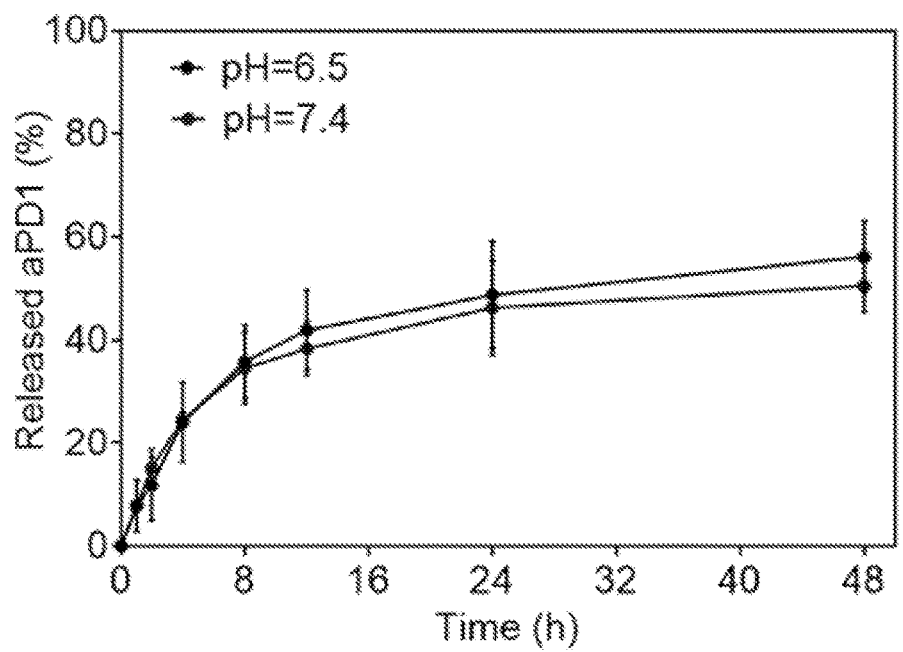
FIG. 30. Accumulated percentage of aPD1 released from NPs incubated in pH 6.5 or pH 7.4 buffer solution. Error bars indicate SD (n=3).
Figure 31:
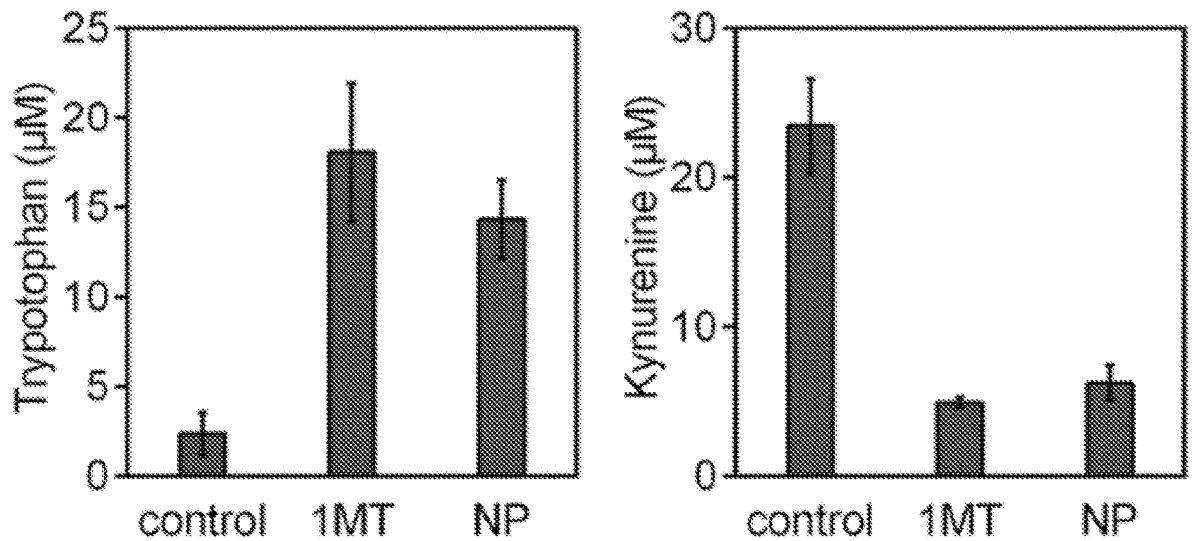
FIG. 31. IDO enzyme activity was measured as the inhibition of tryptophan consumption and kynurenine production after the free 1-MT and NP treatment. Error bars indicate SD (n=3).

To evaluate the HAase-triggered dissociation of the NPs and the subsequent release of aPD1 and 1-MT, the evolutional disassembly behaviors of HA-NPs over time was investigated. The conformation and size of the HA-NPs exhibited a time-dependent manner after the addition of HAase. The particles gradually dissociated in four hours and the size decreased to 8 nm after the continuous incubation with HAase (1 mg/mL) for 24 h (FIG. 1c and FIG. 29). The in vitro release profile of aPD1 from the self-assembled m-HA with or without HAase was monitored at pH 6.5 to mimic the physiological release kinetics in the mildly acidic the tumor microenvironment (FIG. 30). A significantly higher aPD1 release profile was achieved from the sample with HAase due to the dissociation of the HA-NPs matrix mediated by the enzymatic hydrolysis, whereas only a small amount of aPD1 was released from the HA-NPs in PBS solution without the HAase (FIG. 1d). Furthermore, a similar release pattern was observed for 1-MT from the HA-NPs, measured by the high performance liquid chromatography (HPLC). Without the HAase, only about 8% of 1-MT was released from the HA-NPs within 8 h and approximately 18% of 1-MT was released within 48 h. In comparison, the 1-MT showed promoted cumulative release by a factor of five with the assistance of HAase (FIG. 1e). It was also observed that the released 1-MT from the HA-NPs interrupted the kynurenines production at a similar pattern in comparison to the one treated with native 1-MT (FIG. 31). Collectively, these results demonstrated that the HAase facilitated to dissociate the self-assembled HA-NPs, thereby promoting the sustained release of aPD1 and 1-MT simultaneously.

Figure 32:
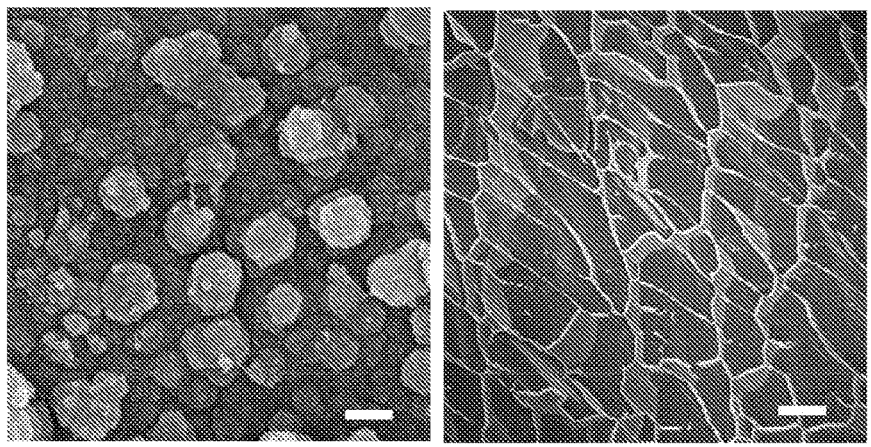
FIG. 32. CryoSEM images of NP (left, scale bar: 200 nm) and NPs inside the HA matrix (right, scale bar 5 µm) during the microneedle fabrication.
Figure 33:
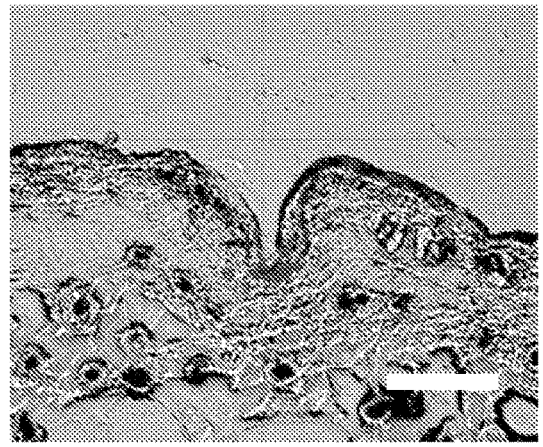
FIG. 33. Merged fluorescence and bright field image of the mouse skin penetrated by 1-MT surrogate rhodamine loaded MNs (scale bar: 200 µm).
Figure 34:
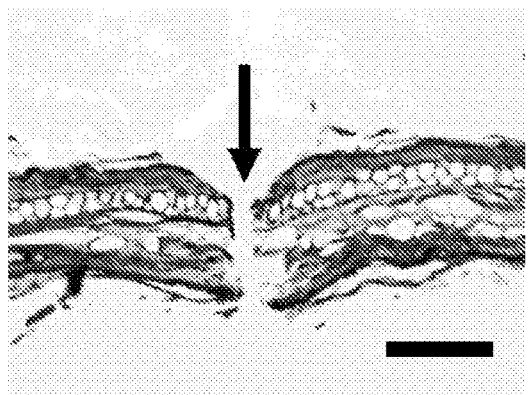
FIG. 34. H&E-stained section of cross-sectional mouse skin area penetrated by one MN (scale bar: 200 µm).
Figure 35:
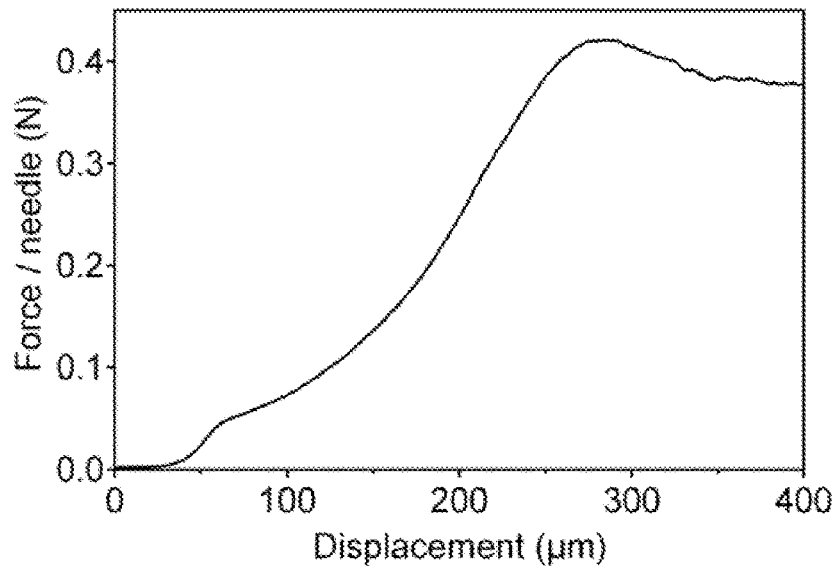
FIG. 35. Mechanical property of the MN. The failure force for desired MN was quantitatively measured as 0.41 N/needle.
Figure 36:
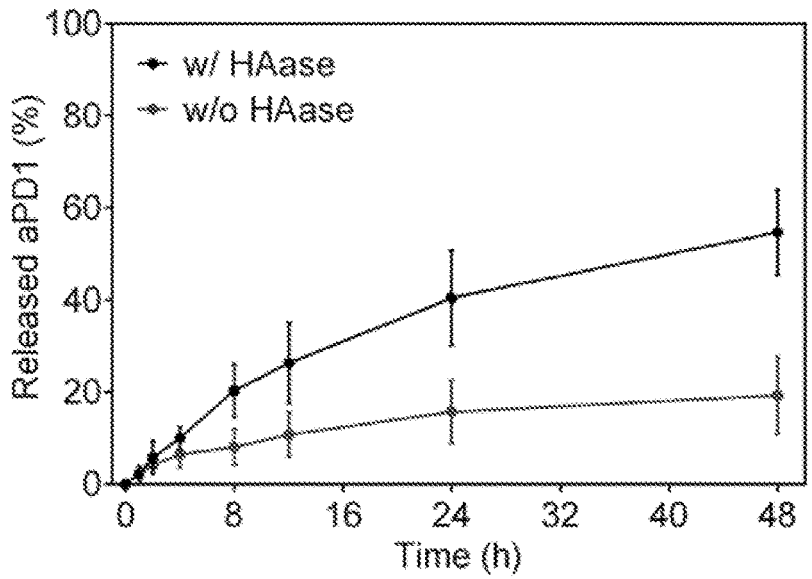
FIG. 36. The release of aPD1 from the microneedle patch was tested by ELISA assay. Error bars indicate SD (n=3).

To target the immune surveillance skin region at the melanoma site, the MN-array patch was fabricated for synergistic delivery of aPD1 and 1-MT. For the MN preparation, the HA-NPs were first loaded in the tips of micromolds by centrifugation. The m-HA hydrogel and entrapped HA-NPs served as the matrix material for the structure of the MNs (FIG. 32). The needles were arranged in a 15×15 array with an area of 10×10 mm² and then tailored to suit the injection syringe. Each needle was conical, with a base radius of 150 μm, a height of 800 μm, and a tip radius of 5 μm (FIG. 2a, 2b). The fluorescence image indicated the distribution of FITC-labeled aPD1 inside the needle matrix (FIG. 2c). To assess the skin penetration capability, prepared MNs were inserted into the dorsum skin of the mouse with gentle force (FIG. 2d). The effective insertion was evidenced by deposited fluorescent payload within the epidermis at a depth of approximately 200 μm (FIG. 33). A histological examination further revealed the complete penetration into the skin (FIG. 34). The array of trypan blue spots on the skin is corresponded to the MN insertion sites, further indicating that all of the MNs were fully inserted (FIG. 2e). The fracture force of the MN array was measured as 0.41±0.03 N per needle, which provided a sixfold margin of safety over the force (0.06 N per needle) required for insertion into the skin without buckling (FIG. 35).[22] To investigate whether HA-NPs encapsulated in the MN maintained their enzyme-mediated degradation capability after MN formulation, the tips of the needles containing HA-NPs were incubated in HAase solution at pH 6.5. With the assistance of MN matrix, a more sustained release profile of aPD1 was achieved from the MN with HAase, whereas insignificant release was collected from the samples without HAase (FIG. 36).

Figure 2G:
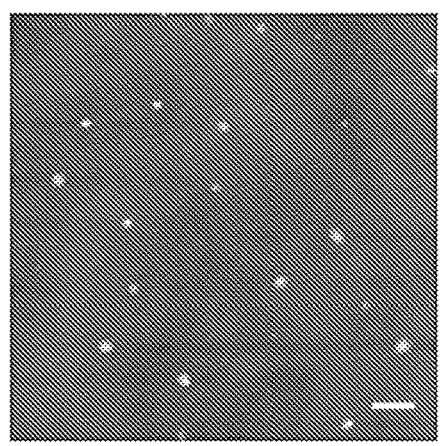
Figure 2H:
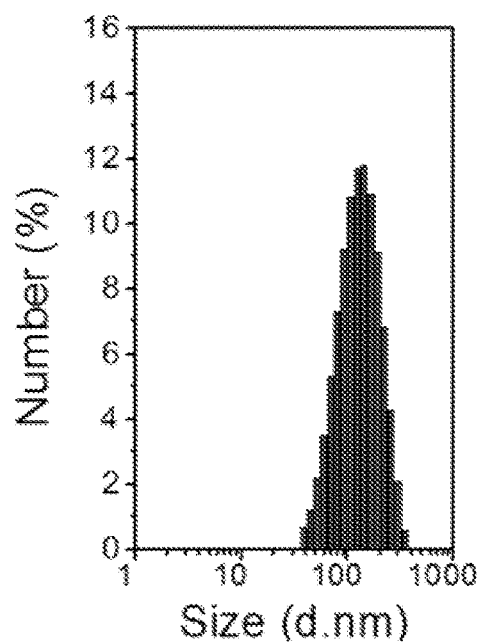
Figure 2I:
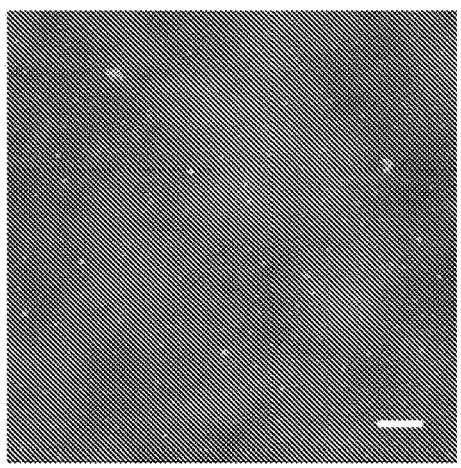
Figure 2J:
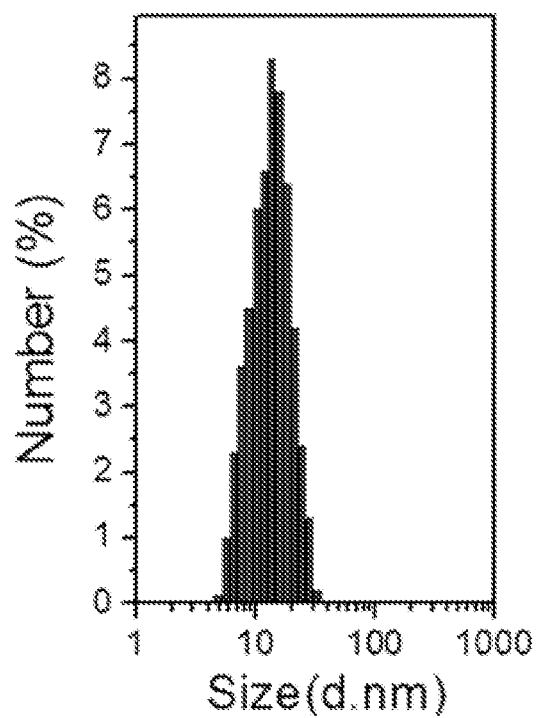
Figure 37:
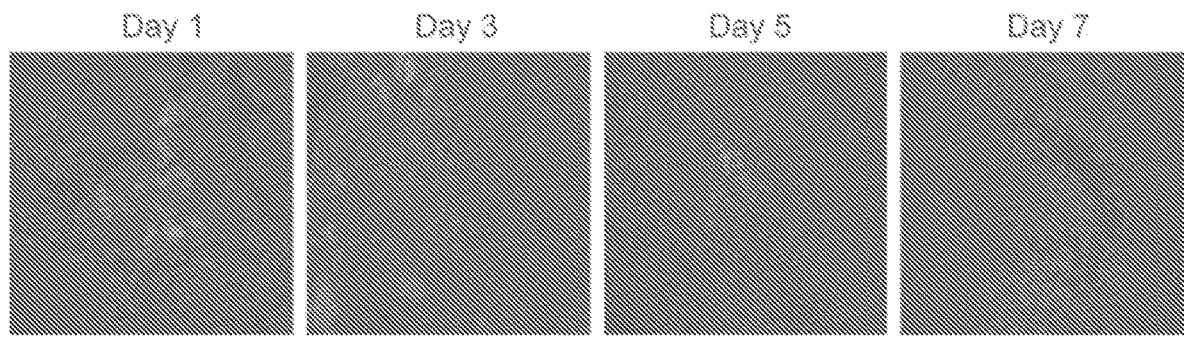
FIG. 37. Immunofluorescence staining of tumors treated with 1-MT-HA/aPD1 loaded MN at different time points (red: aPD1, blue: nucleus) (scale bar: 100 µm).
Figure 38:
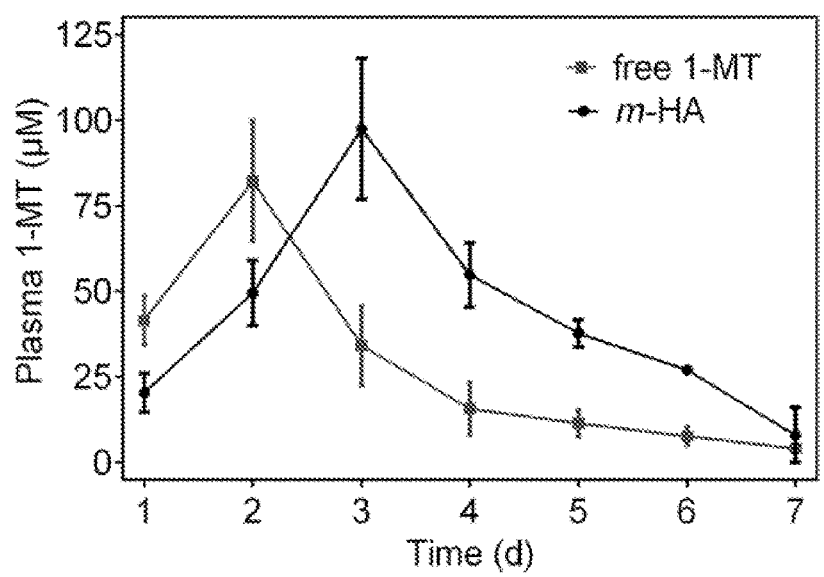
FIG. 38. Plasma levels of 1-MT after microneedle administration was measured by HPLC. Error bars indicate SD (n=3).

HA-NPs formulation with conjugated 1-MT and encapsulated aPD1 can improve their physicochemical properties. Therefore, the in vivo kinetics of free aPD1/1-MT and NPs following MN administration were evaluated in the mice model bearing B16F10 melanoma. The drug retention capability was tested at the tumor site after the MN administration. In vivo bioluminescence imaging was conducted at day 1, day 3 and day 5 post injection of the MN loaded with aPD1 and Cy5.5-1-MT-HA or free Cy5.5-1-MT. A significantly prolonged signal of Cy5.5 around the melanoma site was visualized for the self-assembled 1-MT-HA NP formulation group, whereas little signal could be detected for the free drug group after three days (FIG. 2f, upper). This indicated the 1-MT tended to remain at the melanoma site with the patch after conjugation toward HA, whereas the free 1-MT was quickly cleaved from the patch and eliminated by the body within one day (FIG. 2f, lower). The longer retention time was also implicated in the active targeting based on the affinity between conjugated HA and CD44 receptors in the tumorigenesis.[40] The biodistribution of 1-MT occurring in the tumor and the major organs were compared at various time points after administration, which showed the highest accumulations in the tumor followed by the lung and liver (FIG. 2g). A similar pattern was observed compared to the biodistribution at the tumor site and other organs in the control group. Quantification of signals showed that the accumulation of conjugated 1-MT at melanoma site was three-fold higher compared to the free 1-MT at day 1 and fivefold higher at day two and day three post MN treatment (FIG. 2h). More importantly, a significantly increased tumor uptake of encapsulated aPD1 was observed by the immunofluorescence staining of the tumor slides in the HA-NPs group compared to the control group (FIG. 2i and FIG. 37). Blood was drawn at different time intervals and HPLC analysis of 1-MT showed that a greatly prolonged blood-circulation time occurred when conjugated toward HA (FIG. 38). The sustained high concentrations of the drugs within tumor regions as well as in peripheral circulation would enhance the immune system capability to treat not only primary tumor but also metastatic tumors in the body.

The B16F10 mouse melanoma tumor model, which is a highly aggressive tumor model was used to evaluate the efficacy of synergistic immunotherapy in a clinical relevant setting. The B16F10-luc cancer cells were subcutaneously implanted to the female C57BL/6 mice in the rear dorsal area. The melanoma-bearing mice were grouped and treated with a single administration of blank MN patch (Group 1 (G1)), intravenous (i.v.) injection of aPD1 (Group 1 (G2)), intratumoral (i.t.) injection of aPD1 and 1-MT (Group 1 (G3)), aPD1 loaded MN patch (Group 1 (G4)), 1-MT loaded MN patch (Group 1 (G5)) and aPD1/1-MT NPs loaded MN patch (Group 1 (G6)). The NPs administered by MNs significantly delayed the tumor growth, resulting the smallest tumors in mice after 7 days of therapy (FIG. 3a). Taking the tumor penetration efficiency into consideration, aPD1 and 1-MT administered i.v. did not achieve significant delay in the tumor growth, but nonetheless the average tumor weight was lower than the blank MN group. The groups administrated with the MN containing aPD1 or 1-MT only showed limited anti-tumor efficiency (FIG. 3b, 3c). These tumor regressions show that the NPs loaded MN released the aPD1 and the small molecular IDO inhibitors in a synergistic and sustained manner. The marked delay in the tumor volumes was correlated with their survival in the B16F10 melanoma models. 70% survival of mice was observed in 40 days after the synergistic treatment which is better than our previous results.[40] Conversely, none of the mice survived in the four control groups after 40 days (FIG. 3d). Furthermore, no obvious weight loss or other clinical signs of toxicity was observed after various treatments, and thus the 1-MT/aPD1 MN patch could be a safe cancer treatment technique with substantial clinical potential. (FIG. 3e).

Figure 39:
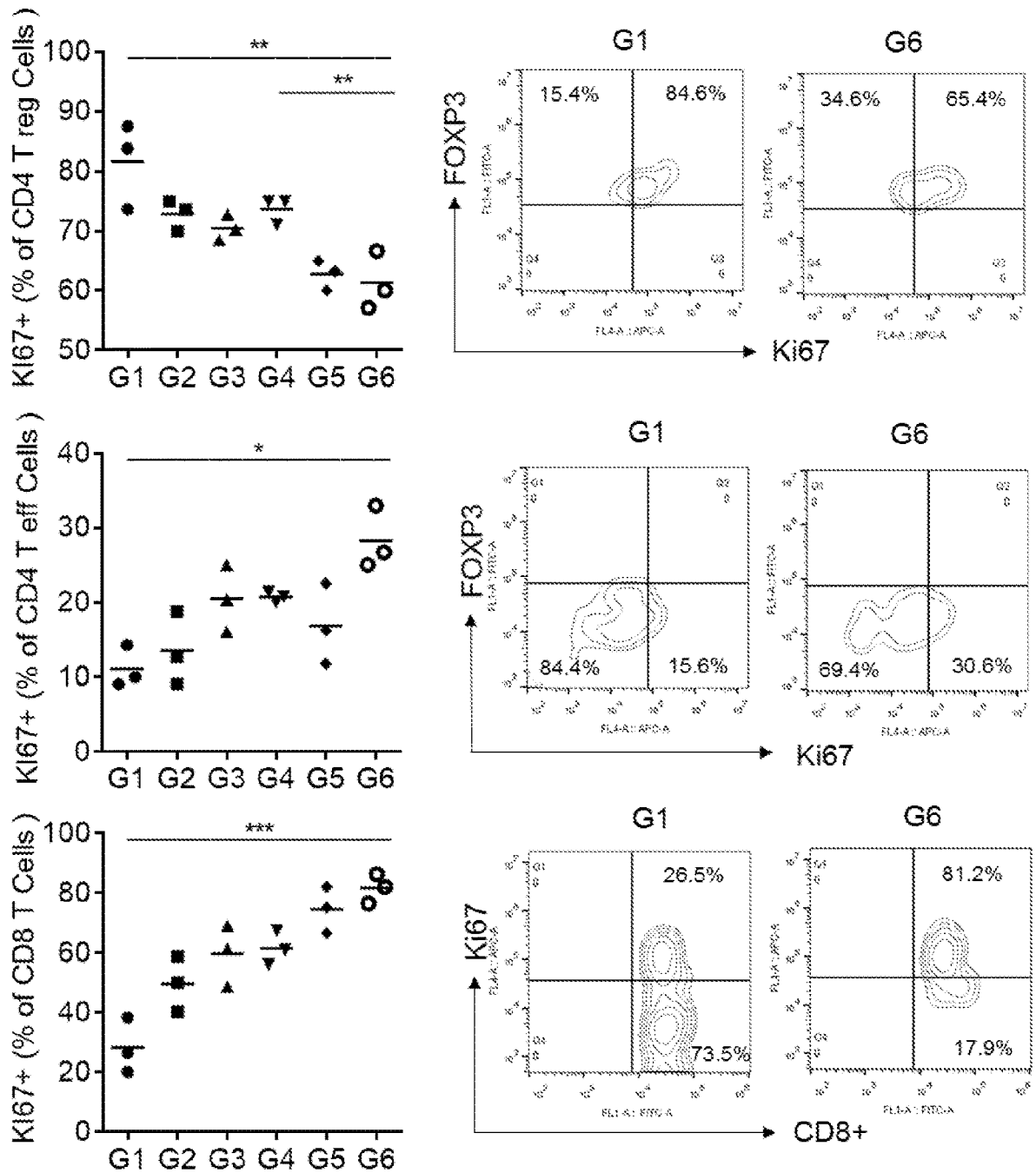
FIG. 39. The CD4+Foxp3+ regulatory T cell, CD4+Foxp3 effector T cell and CD8+ proliferation within the tumors of mice were measured by the expression of the cell cycle associated protein Ki67. Error bars indicate SD (n=3).
Figure 40:
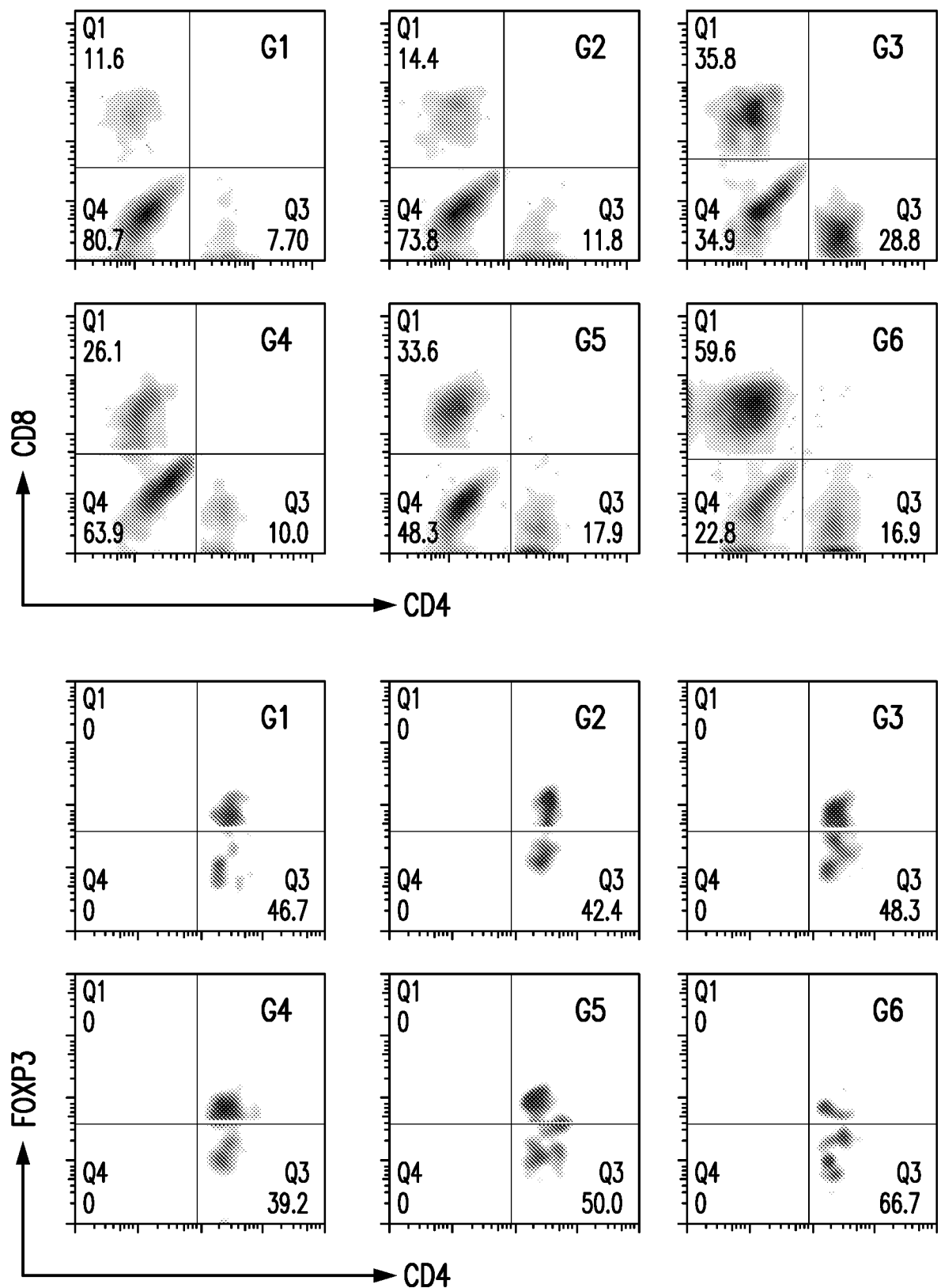
FIG. 40. Representative FACS plots are shown for two independent experiments done with five mice of the residual tumors in each group.
Figure 41:
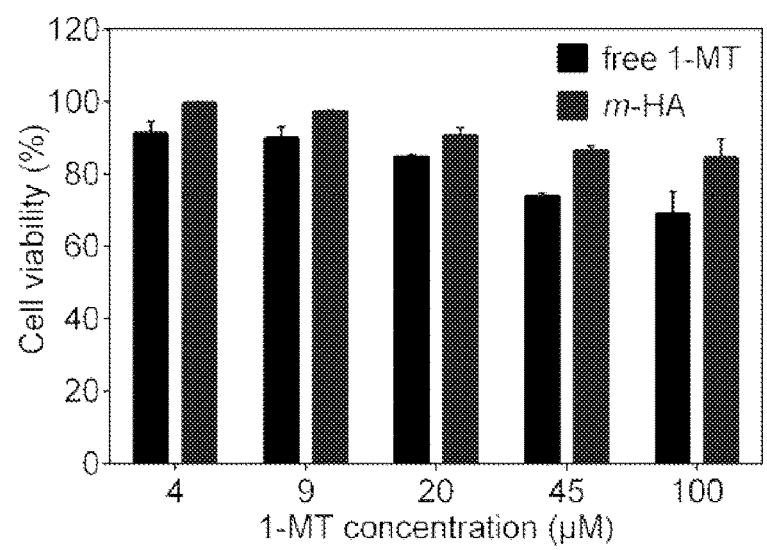
FIG. 41. The cytotoxicity of free 1-MT and m-HA NPs after 24 h of incubation with B16F10 cells. Error bars indicate SD (n=6).
Figure 42:
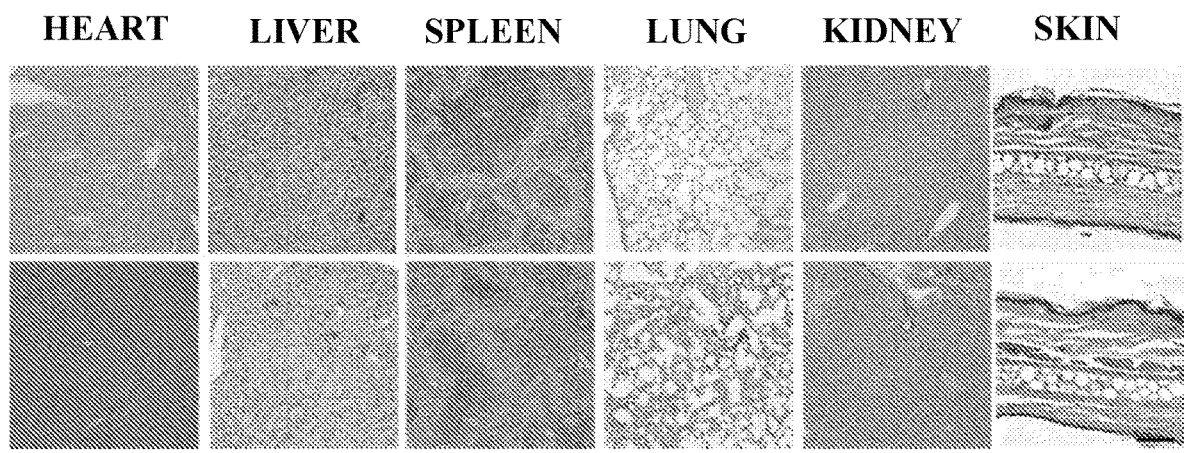
FIG. 42. H&E-stained the major organ sections 2 d post-administration with PBS (top panel) and the microneedle patch (bottom panel) (scale bar: 200 µm).

To address the cellular mechanisms mediating the tumor regression in this system, the TILs were isolated and analyzed by the immunofluorescence and flow cytometry on day 12 (FIG. 4a). Immunofluorescence images showed that the tumors in the control groups had limited T-cell infiltration (FIG. 4b). Contrasting the control, tumors treated with synergistic therapy were remarkably infiltrated by both CD8+ and CD4+ T cells. The hematoxylin and eosin (H&E) staining further indicated a decreased population of tumor cells visualized by the melanin (FIG. 4c). The absolute number of CD3+ cells in the tumors was significantly lower in the aPD1/1-MT treated mice on day 12, which also corresponded to the decrease in the tumor weight. In addition, a significant higher CD8+ and CD4+ effector T cell proliferation within the tumors was observed, as measured by the expression of the cell cycle associated protein Ki67 (FIG. 39). More importantly, the CD8+ cells/milligram tumor recruited to the tumor site increased by almost six folds in the aPD1/1-MT treated mice compared with the blank MN control, indicating that B16F10-reactive CD8+ T cells were trafficking to the tumor site. Moreover, the tumor-infiltrating CD4+FoxP3+ T cells were analyzed. In contrast to the effector T cells, the cell recruitment was inhibited for regulatory T (Treg) cells in the treated groups. The decrease in Treg cell infiltration was also reflected in the remarkable increase in CD8+ T cell to Treg cell ratios. Intratumoral ratios of T effector cell to Treg cell were also enhanced in mice after aPD1/1-MT therapy which correlated with tumor regression (FIG. 40). Taken together, these observations show that the synergistic therapy delivered aPD1 and 1-MT efficiently at the tumor site, resulting in a qualitatively more effective cytotoxic T cell response (FIG. 4d). Notably, the system showed its biocompatibility and low cytotoxicity (FIG. 41). Histopathology was conducted on major organs such as skin, colon, liver, kidney, lungs, and intestines, and no evidence of toxicity or inflammation was observed (FIG. 42).

In summary, a synergistic transcutaneous immunotherapy that preferentially targets the immunoinhibitory receptor PD1 and immunosuppressive enzyme IDO to enhance anti-tumor response is described in this example. The platform using MN as a carrier to deliver checkpoint inhibitor aPD1 and 1-MT facilitates the retention time of therapeutics in the diseased site and potentially alleviates the side effects of systematic administration of cancer immunotherapeutic.

Methods

Materials

All chemicals unless mentioned were purchased from Sigma-Aldrich. Sodium hyaluronic acid (HA, the molecular weight of 50 kDa) was purchased from Freda Biochem Co., Ltd. (Shandong, China), skin affix surgical adhesive was purchased from Medline Industries, Inc. Anti PD1 antibody (aPD1) used in vivo was purchased from Biolegend Inc. (Cat. #124329, Clone: 10F.9G2) and 1-methyl-DL-tryptophan was purchased from Sigma. Staining antibodies included CD3, CD4, CD8, Ki67 (Thermo Scientific), intracellular Foxp3 (eBioscience) for FACS analysis following manufacturers' instructions and analyzed on a Calibur FACS instrument (BD) using flowjo software (version 10). The deionized water was prepared by a Millipore NanoPure purification system (resistivity higher than 18.2 MΩ·cm$^{-1}$). All the organic solvents were ordered from Fisher Scientific Inc. and used as received.

Preparation of HA-NPs

NPs were prepared by self-assembly in aqueous solution. Briefly, 10 mg of amphiphilic m-HA and 1 mg aPD1 was dissolved in water/methanol (2:1 vol/vol). The emulsion was stirred at 4° C. for 2 h. Then, the methanol was removed by dialysis against deionized (DI) water for 3 d to remove the unconjugated 1-MT and further filtered by a centrifugal filter (3,000 Da molecular mass cutoff, Millipore). The free aPD1 was removed using a G-100 Sephadex column equilibrated with PBS at pH 7.4. The final NP suspension in DI water was stored at 4° C. for later study. The zeta-potential and size distribution of NP suspension in DI water were measured on the Zetasizer (Nano ZS; Malvern).

The loading capacity (LC) and encapsulation efficiency (EE) of aPD1-encapsulated NPs were determined by measuring the amount of non-encapsulated IgG through mouse IgG ELISA assay and using empty particles as basic correction. LC and EE were calculated as LC=(A−B)/C, EE=(A−B)/A, where A was expected encapsulated amount of aPD1, B was the free amount of aPD1 in the collection solution, and C was the total weight of the particles. Particle size and polydispersity intensity were measured by dynamic light scattering (DLS) on the Malvern Zetasizer NanoZS. The zeta potential of the NPs was determined by their electrophoretic mobility using the same instrument after appropriate dilution. Measurements were tested in triplicate at room temperature. The TEM images of NPs morphology were obtained on a JEOL 2000FX TEM instrument at 100 kV.

For the fluorescent NPs, Cyanine5.5 NHS ester (Lumiprobe, Cy5.5) was covalently coupled to the primary amines of the aPD1 and 1-MT. The Cy5.5 was dissolved in anhydrous DMSO immediately before use, at a concentration of 10 mg/ml. Cy5.5 and 1-MT reacted at optimal ratio of 5:1. For the conjugation with aPD1, 40 μg Cy5.5 per mg of antibody was mixed immediately. The tube was wrapped in foil and incubated at room temperature for 1 hour. The unreacted Cy5.5 was removed and the aPD1 was exchanged by gel filtration using Sephadex G-25M.

In Vitro aPD1 Release Profile Studies

To measure the aPD1 release profile from the HA-NPs, 1 mg/mL HAase was added to the HA-NPs suspension at 37° C. and pH=6.4 on an orbital shaker. At the predetermined times, 10 μL of the sample was removed for analysis and 10 μL of fresh release media was then added to the well to maintain a constant volume and placed back on the orbital shaker. The amount of aPD1 released from the HA-NPs suspension was diluted and measured by mouse IgG ELISA. The absorbance was detected in a UV-Vis spectrophotometer at 450 nm, and the concentration was interpolated from an antibody standard curve. In vitro release of antibody from MNs was evaluated through incubation of MN patches in 2 mL release media in a 6 well plate.

Fabrication and Characterization of Microneedles

All of the MNs in the context were fabricated using six silicone molds with arrays of conical holes machined by laser ablation (Blueacre Technology Ltd.). Each microneedle had a 300 μm by 300 μm round base tapering to a height of 800 μm with a tip radius of around 5 μm. The microneedles were arranged in a 15 by 15 array with 600 μm center-to-center spacing.

The prepared HA-NPs were concentrated in 0.5 mL distilled water using Labconco (7812002) CentriVap Concentrator. Then, 50 uL of HA-NPs suspension (containing 1 mg of NPs) was directly deposited by pipetting onto each silicone micromold surface followed by vacuum (600 mmHg) condition for 5 min to allow the NP solution flowing into the cavities. After that, the micromolds were transferred to a Hettich Universal 32R centrifuge for 20 min at 2000 rpm to compact HA-NPs into microneedle cavities. The residue HA-NPs on the mold surface during the fabrication were collected and the deposition process was repeated three times to ensure loading uniformity. Next, a piece of 4 cm×9 cm silver adhesive tape was applied around the 2 cm×2 cm micromold baseplate. In addition, 3 mL dissolved m-HA (4 wt %) solution was added to the prepared micromold reservoir. For the blank MN without 1-MT loading, native HA was used to fabricate the MN matrix. The final device underwent drying at 25° C. in a vacuum desiccator overnight. After desiccation was completed, the needle arrays were carefully separated from the silicone mold and the needle base can be tailored into a round shape to fit the injection syringe. The resulting product can be stored in a sealed six well container for up to 30 days. The fluorescent microneedles were fabricated with Rhodamine B labeled HA and Cy5.5 labeled aPD1 or 1-MT nanoparticles. The morphology of the microneedles was characterized on a FEI Verios 460L field-emission scanning electron microscope (FESEM) operating at 20 kV after sputter coating with gold/palladium at the Analytical Instrumentation Facility. The fluorescence images of MNs were taken by Olympus IX70 multi-parameter fluorescence microscope.

Mice and In Vivo Tumor Models

Female C57B6 mice were purchased from Jackson Lab (USA). All mouse studies were performed in the context of an animal protocol approved by the Institutional Animal Care and Use Committee at North Carolina State University and University of North Carolina at Chapel Hill. Mice were weighed and randomly divided into different groups. 7 d after 1×10$^6$ luciferase-tagged B 16F10 tumor cells transplanted into the back of mice (the tumor reaches 50-60 mm$^3$), aPD1 (1 mg/kg) and 1MT (2.5 mg/kg) were administered into mice by intravenous/intratumoral HA-NPs injection or by microneedle. MN patch was applied on the dorsal cervical skin region for 10 min and further fixed using skin affix surgical adhesive purchased from Medline Industries, Inc. The tumor growth was monitored by bioluminescence signals of B16F10 cells. Tumor incidences were monitored by physical examination and sizes were also measured by digital caliper over time. The tumor area (mm$^2$) was calculated as (long diameter×short diameter). To assess potential toxicities, mice were monitored daily for weight loss, and histopathology was conducted on the tumor and major organs after treatment (i.e., skin, heart, liver, spleen, lungs and kidney).

REFERENCES CITED IN THIS EXAMPLE

The disclosures of all articles and references, including patent applications and publications, are incorporated by reference for all purposes.

1. Topalian, Suzanne L.; Drake, Charles G.; Pardoll, Drew M., Immune Checkpoint Blockade: A Common Denominator Approach to Cancer Therapy. *Cancer Cell* 2015, 27 (4), 450-461.
2. Cheung, A. S.; Mooney, D. J., Engineered materials for cancer immunotherapy. *Nano Today* 2015, 10 (4), 511-531.
3. Jeanbart, L.; Swartz, M. A., Engineering opportunities in cancer immunotherapy. *Proc. Natl. Acad. Sci.* 2015, 112 (47), 14467-14472.
4. Koshy, S. T.; Mooney, D. J., Biomaterials for enhancing anti-cancer immunity. *Curr. Opin. Biotechnol.* 2016, 40, 1-8.
5. Sharma, P.; Allison, J. P., The future of immune checkpoint therapy. *Science* 2015, 348 (6230), 56-61.
6. Sharma, P.; Allison, James P., Immune Checkpoint Targeting in Cancer Therapy: Toward Combination Strategies with Curative Potential. *Cell* 2015, 161 (2), 205-214.
7. Zou, W.; Wolchok, J. D.; Chen, L., PD-L1 (B7-H1) and PD-1 pathway blockade for cancer therapy: Mechanisms, response biomarkers, and combinations. *Sci. Transl. Med.* 2016, 8 (328), 328rv4-328rv4.
8. Buchbinder, E. I.; Hodi, F. S., Melanoma in 2015: Immune-checkpoint blockade—durable cancer control. *Nat. Rev. Clin. Oncol.* 2016, 13 (2), 77-78.
9. Larkin, J.; Chiarion-Sileni, V.; Gonzalez, R.; Grob, J. J.; Cowey, C. L.; Lao, C. D.; Schadendorf, D.; Dummer, R.; Smylie, M.; Rutkowski, P.; Ferrucci, P. F.; Hill, A.; Wagstaff, J.; Carlino, M. S.; Haanen, J. B.; Maio, M.; Marquez-Rodas, I.; McArthur, G. A.; Ascierto, P. A.; Long, G. V.; Callahan, M. K.; Postow, M. A.; Grossmann, K.; Sznol, M.; Dreno, B.; Bastholt, L.; Yang, A.; Rollin, L. M.; Horak, C.; Hodi, F. S.; Wolchok, J. D., Combined Nivolumab and Ipilimumab or Monotherapy in Untreated Melanoma. *N. Engl. J. Med.* 2015, 373 (1), 23-34.
10. Sullivan, R. J.; Flaherty, K. T., Immunotherapy: Anti-PD-1 therapies—a new first-line option in advanced melanoma. *Nat. Rev. Clin. Oncol.* 2015, 12 (11), 625-626.
11. Rosenberg, J. E.; Hoffman-Censits, J.; Powles, T.; van der Heijden, M. S.; Balar, A. V.; Necchi, A.; Dawson, N.; O'Donnell, P. H.; Balmanoukian, A.; Loriot, Y.; Srinivas, S.; Retz, M. M.; Grivas, P.; Joseph, R. W.; Galsky, M. D.; Fleming, M. T.; Petrylak, D. P.; Perez-Gracia, J. L.; Burris, H. A.; Castellano, D.; Canil, C.; Bellmunt, J.; Bajorin, D.; Nickles, D.; Bourgon, R.; Frampton, G. M.; Cui, N.; Mariathasan, S.; Abidoye, O.; Fine, G. D.; Dreicer, R., Atezolizumab in patients with locally advanced and metastatic urothelial carcinoma who have progressed following treatment with platinum-based chemotherapy: a single-arm, multicentre, phase 2 trial. *The Lancet* 2016, 387 (10031), 1909-1920.
12. Postow, M. A.; Chesney, J.; Pavlick, A. C.; Robert, C.; Grossmann, K.; McDermott, D.; Linette, G. P.; Meyer, N.; Giguere, J. K.; Agarwala, S. S.; Shaheen, M.; Ernstoff, M. S.; Minor, D.; Salama, A. K.; Taylor, M.; Ott, P. A.; Rollin, L. M.; Horak, C.; Gagnier, P.; Wolchok, J. D.; Hodi, F. S., Nivolumab and ipilimumab versus ipilimumab in untreated melanoma. *N. Engl. J. Med.* 2015, 372 (21), 2006-17.
13. Robert, C.; Schachter, J.; Long, G. V.; Arance, A.; Grob, J. J.; Mortier, L.; Daud, A.; Carlino, M. S.; McNeil, C.; Lotem, M.; Larkin, J.; Lorigan, P.; Neyns, B.; Blank, C. U.; Hamid, O.; Mateus, C.; Shapira-Frommer, R.; Kosh, M.; Zhou, H.; Ibrahim, N.; Ebbinghaus, S.; Ribas, A.; investigators, K.-. Pembrolizumab versus Ipilimumab in Advanced Melanoma. *N. Engl. J. Med.* 2015, 372 (26), 2521-32.
14. Le, D. T.; Uram, J. N.; Wang, H.; Bartlett, B. R.; Kemberling, H.; Eyring, A. D.; Skora, A. D.; Luber, B. S.; Azad, N. S.; Laheru, D.; Biedrzycki, B.; Donehower, R. C.; Zaheer, A.; Fisher, G. A.; Crocenzi, T. S.; Lee, J. J.; Duffy, S. M.; Goldberg, R. M.; de la Chapelle, A.; Koshiji, M.; Bhaijee, F.; Huebner, T.; Hruban, R. H.; Wood, L. D.; Cuka, N.; Pardoll, D. M.; Papadopoulos, N.; Kinzler, K. W.; Zhou, S.; Cornish, T. C.; Taube, J. M.; Anders, R. A.; Eshleman, J. R.; Vogelstein, B.; Diaz, L. A., PD-1 Blockade in Tumors with Mismatch-Repair Deficiency. *N. Engl. J. Med.* 2015, 372 (26), 2509-2520.
15. Spranger, S.; Spaapen, R. M.; Zha, Y.; Williams, J.; Meng, Y.; Ha, T. T.; Gajewski, T. F., Up-Regulation of PD-L1, IDO, and Tregs in the Melanoma Tumor Microenvironment Is Driven by CD8+ T Cells. *Sci. Transl. Med.* 2013, 5 (200), 200ra116-200ra116.
16. Mellor, A. L.; Munn, D. H., Ido expression by dendritic cells: tolerance and tryptophan catabolism. *Nat. Rev. Immunol.* 2004, 4 (10), 762-774.
17. Moon, Y. W.; Hajjar, J.; Hwu, P.; Naing, A., Targeting the indoleamine 2,3-dioxygenase pathway in cancer. *J. Immunother. Cancer.* 2015, 3 (1).
18. Muller, A. J.; DuHadaway, J. B.; Donover, P. S.; Sutanto-Ward, E.; Prendergast, G. C., Inhibition of indoleamine 2,3-dioxygenase, an immunoregulatory target of the cancer suppression gene Bin1, potentiates cancer chemotherapy. *Nat. Med.* 2005, 11 (3), 312-319.
19. Topalian, S. L.; Hodi, F. S.; Brahmer, J. R.; Gettinger, S. N.; Smith, D. C.; McDermott, D. F.; Powderly, J. D.; Carvajal, R. D.; Sosman, J. A.; Atkins, M. B.; Leming, P. D.; Spigel, D. R.; Antonia, S. J.; Horn, L.; Drake, C. G.; Pardoll, D. M.; Chen, L.; Sharfman, W. H.; Anders, R. A.; Taube, J. M.; McMiller, T. L.; Xu, H.; Korman, A. J.; Jure-Kunkel, M.; Agrawal, S.; McDonald, D.; Kollia, G. D.; Gupta, A.; Wigginton, J. M.; Sznol, M., Safety, Activity, and Immune Correlates of Anti-PD-1 Antibody in Cancer. *N. Engl. J. Med.* 2012, 366 (26), 2443-2454.
20. DeMuth, P. C.; Min, Y.; Irvine, D. J.; Hammond, P. T., Implantable Silk Composite Microneedles for Programmable Vaccine Release Kinetics and Enhanced Immunogenicity in Transcutaneous Immunization. *Adv. Healthcare Mater.* 2014, 3 (1), 47-58.
21. DeMuth, P. C.; Moon, J. J.; Suh, H.; Hammond, P. T.; Irvine, D. J., Releasable Layer-by-Layer Assembly of Stabilized Lipid Nanocapsules on Microneedles for Enhanced Transcutaneous Vaccine Delivery. *ACS Nano* 2012, 6 (9), 8041-8051.
22. Sullivan, S. P.; Koutsonanos, D. G.; del Pilar Martin, M.; Lee, J. W.; Zarnitsyn, V.; Choi, S.-O.; Murthy, N.; Compans, R. W.; Skountzou, I.; Prausnitz, M. R., Dissolving polymer microneedle patches for influenza vaccination. *Nat. Med.* 2010, 16 (8), 915-920.
23. Kim, Y.-C.; Park, J.-H.; Prausnitz, M. R., Microneedles for drug and vaccine delivery. *Adv. Drug Delivery Rev.* 2012, 64 (14), 1547-1568.

24. Prausnitz, M. R.; Langer, R., Transdermal drug delivery. *Nat. Biotechnol.* 2008, 26 (11), 1261-1268.
25. DeMuth, P. C.; Su, X.; Samuel, R. E.; Hammond, P. T.; Irvine, D. J., Nano-Layered Microneedles for Transcutaneous Delivery of Polymer Nanoparticles and Plasmid DNA. *Adv. Mater.* 2010, 22 (43), 4851-4856.
26. Uyttenhove, C.; Pilotte, L.; Théate, I.; Stroobant, V.; Colau, D.; Parmentier, N.; Boon, T.; Van den Eynde, B. J., Evidence for a tumoral immune resistance mechanism based on tryptophan degradation by indoleamine 2,3-dioxygenase. *Nat. Med.* 2003, 9 (10), 1269-1274.
27. Pilotte, L.; Larrieu, P.; Stroobant, V.; Colau, D.; Dolusic, E.; Frederick, R.; De Plaen, E.; Uyttenhove, C.; Wouters, J.; Masereel, B.; Van den Eynde, B. J., Reversal of tumoral immune resistance by inhibition of tryptophan 2,3-dioxygenase. *Proc. Natl. Acad. Sci.* 2012, 109 (7), 2497-2502.
28. Awuah, S. G.; Zheng, Y.-R.; Bruno, P. M.; Hemann, M. T.; Lippard, S. J., A Pt(IV) Pro-drug Preferentially Targets Indoleamine-2,3-dioxygenase, Providing Enhanced Ovarian Cancer Immuno-Chemotherapy. *J. Am. Chem. Soc.* 2015, 137 (47), 14854-14857.
29. Yu, J.; Zhang, Y.; Ye, Y.; DiSanto, R.; Sun, W.; Ranson, D.; Ligler, F. S.; Buse, J. B.; Gu, Z., Microneedle-array patches loaded with hypoxia-sensitive vesicles provide fast glucose-responsive insulin delivery. *Proc. Natl. Acad. Sci.* 2015, 112 (27), 8260-8265.
30. Lu, Y.; Sun, W.; Gu, Z., Stimuli-responsive nanomaterials for therapeutic protein delivery. *J. Controlled Release* 2014, 194, 1-19.
31. Moon, J. J.; Huang, B.; Irvine, D. J., Engineering Nano- and Microparticles to Tune Immunity. *Adv. Mater.* 2012, 24 (28), 3724-3746.
32. Wang, C.; Sun, W.; Wright, G.; Wang, A.; Gu, Z., Inflammation-Triggered Cancer Immunotherapy by Programmed Delivery of CpG and Anti-PD1 Antibody. *Adv. Mater.* 2016.
33. Tai, W.; Mo, R.; Di, J.; Subramanian, V.; Gu, X.; Buse, J. B.; Gu, Z., Bio-Inspired Synthetic Nanovesicles for Glucose-Responsive Release of Insulin. *Biomacromolecules* 2014, 15 (10), 3495-3502.
34. Lu, Y.; Hu, Q.; Lin, Y.; Pacardo, D. B.; Wang, C.; Sun, W.; Ligler, F. S.; Dickey, M. D.; Gu, Z., Transformable liquid-metal nanomedicine. *Nat. Commun.* 2015, 6, 10066.
35. Wang, C.; Ye, Y.; Hochu, G. M.; Sadeghifar, H.; Gu, Z., Enhanced Cancer Immunotherapy by Microneedle Patch-Assisted Delivery of Anti-PD1 Antibody. *Nano Lett.* 2016, 16 (4), 2334-2340.
36. Mitragotri, S.; Anderson, D. G.; Chen, X.; Chow, E. K.; Ho, D.; Kabanov, A. V.; Karp, J. M.; Kataoka, K.; Mirkin, C. A.; Petrosko, S. H.; Shi, J.; Stevens, M. M.; Sun, S.; Teoh, S.; Venkatraman, S. S.; Xia, Y.; Wang, S.; Gu, Z.; Xu, C., Accelerating the Translation of Nanomaterials in Biomedicine. *ACS Nano* 2015, 9 (7), 6644-6654.
37. Peer, D.; Karp, J. M.; Hong, S.; Farokhzad, O. C.; Margalit, R.; Langer, R., Nanocarriers as an emerging platform for cancer therapy. *Nat. Nanotechnol.* 2007, 2 (12), 751-760.
38. DeMuth, P. C.; Li, A. V.; Abbink, P.; Liu, J.; Li, H.; Stanley, K. A.; Smith, K. M.; Lavine, C. L.; Seaman, M. S.; Kramer, J. A.; Miller, A. D.; Abraham, W.; Suh, H.; Elkhader, J.; Hammond, P. T.; Barouch, D. H.; Irvine, D. J., Vaccine delivery with microneedle skin patches in nonhuman primates. *Nat. Biotechnol.* 2013, 31 (12), 1082-1085.
39. Li, W. A.; Mooney, D. J., Materials based tumor immunotherapy vaccines. *Curr. Opin. Immunol.* 2013, 25 (2), 238-245.
40. Hu, Q.; Sun, W.; Lu, Y.; Bomba, H. N.; Ye, Y.; Jiang, T.; Isaacson, A. J.; Gu, Z., Tumor Microenvironment-Mediated Construction and Deconstruction of Extracellular Drug-Delivery Depots. *Nano Lett.* 2016, 16 (2), 1118-1126.
41. Mai, Y.; Eisenberg, A., Self-assembly of block copolymers. *Chem. Soc. Rev.* 2012, 41 (18), 5969.
42. Hervé, C.; Beyne, P.; Jamault, H.; Delacoux, E., Determination of tryptophan and its kynurenine pathway metabolites in human serum by high-performance liquid chromatography with simultaneous ultraviolet and fluorimetric detection. *J. Chromatogr. B Biomed. Sci. Appl.* 1996, 675 (1), 157-161.
43. Hwang, S. L.; Chung, N. P.-Y.; Chan, J. K.-Y.; Lin, C.-L. S., Indoleamine 2, 3-dioxygenase (IDO) is essential for dendritic cell activation and chemotactic responsiveness to chemokines. *Cell Res.* 2005, 15 (3), 167-175.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The invention claimed is:

1. A controlled-release pharmaceutical dosage form comprising:
a CpG oligodeoxynucleotide nano-cocoon, wherein the nano-cocoon comprises an immunotherapeutic agent and inflammation-responsive nanoparticles, wherein the nanoparticles encapsulate a restriction enzyme, wherein the inflammation-responsive nanoparticles comprise triglycerol monostearate (TGMS), and wherein the restriction enzyme is HhaI, and wherein the immunotherapeutic agent is selected from an anti-PD1 antibody, an anti-PDL1 antibody, an anti-CTLA4 antibody, or a combination thereof.

2. The dosage form of claim 1, wherein the immunotherapeutic agent is an anti-PD1 antibody.

3. The dosage form of claim 2, wherein the anti-PD1 antibody is nivolumab.

4. The dosage form of claim 2, wherein the anti-PD1 antibody is pembrolizumab.

5. The dosage form of claim 1, wherein the immunotherapeutic agent is an anti-CTLA4 antibody.

6. The dosage form of claim 5, wherein the anti-CTLA4 antibody is ipilimumab.

7. The dosage form of claim 1, wherein the immunotherapeutic agent is an anti-PD1 antibody in combination with an anti-CTLA4 antibody.

* * * * *

UNITED STATES PATENT AND TRADEMARK OFFICE
CERTIFICATE OF CORRECTION

PATENT NO. : 11,110,168 B2
APPLICATION NO. : 16/085015
DATED : September 7, 2021
INVENTOR(S) : Zhen Gu Page 1 of 1

It is certified that error appears in the above-identified patent and that said Letters Patent is hereby corrected as shown below:

In the Specification

In Column 1, Line 15, insert:
--STATEMENT REGARDING FEDERALLY SPONSORED RESEARCH
This invention was made with government support under grant number TR001111 awarded by the National Institutes of Health. The government has certain rights in the invention.--

Signed and Sealed this
Twenty-eighth Day of February, 2023

Katherine Kelly Vidal
*Director of the United States Patent and Trademark Office*